United States Patent
Zhan et al.

(10) Patent No.: US 12,030,877 B2
(45) Date of Patent: Jul. 9, 2024

(54) PROSTAGLANDIN E SYNTHASE INHIBITORS AND METHODS FOR UTILIZING THE SAME

(71) Applicant: University of Kentucky Research Foundation, Lexington, KY (US)

(72) Inventors: Chang-Guo Zhan, Lexington, KY (US); Fang Zheng, Lexington, KY (US); Kai Ding, Lexington, KY (US); Ziyuan Zhou, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 37 days.

(21) Appl. No.: 17/538,442

(22) Filed: Nov. 30, 2021

(65) Prior Publication Data

US 2022/0081432 A1    Mar. 17, 2022

Related U.S. Application Data

(62) Division of application No. 16/305,386, filed as application No. PCT/US2017/039785 on Jun. 28, 2017, now Pat. No. 11,325,901.

(60) Provisional application No. 62/355,739, filed on Jun. 28, 2016.

(51) Int. Cl.
| | | |
|---|---|---|
| C07D 417/06 | (2006.01) | |
| C07C 205/42 | (2006.01) | |
| C07C 255/41 | (2006.01) | |
| C07D 207/452 | (2006.01) | |
| C07D 231/12 | (2006.01) | |
| C07D 251/20 | (2006.01) | |
| C07D 277/34 | (2006.01) | |
| C07D 403/06 | (2006.01) | |
| C07D 417/04 | (2006.01) | |

(52) U.S. Cl.
CPC .......... *C07D 417/06* (2013.01); *C07C 205/42* (2013.01); *C07C 255/41* (2013.01); *C07D 207/452* (2013.01); *C07D 231/12* (2013.01); *C07D 251/20* (2013.01); *C07D 277/34* (2013.01); *C07D 403/06* (2013.01); *C07D 417/04* (2013.01)

(58) Field of Classification Search
CPC . C07C 205/42; C07C 255/41; C07D 207/452; C07D 231/12; C07D 251/20; C07D 277/34; C07D 403/06; C07D 417/04; C07D 417/06
See application file for complete search history.

(56) References Cited

U.S. PATENT DOCUMENTS

| | | | | |
|---|---|---|---|---|
| 6,372,742 B1 * | 4/2002 | Chin | ............... | A61K 31/426 514/369 |
| 7,879,893 B2 * | 2/2011 | Olsen | ............... | C07D 403/04 548/253 |
| 2009/0123563 A1 | 5/2009 | Kaarsholm et al. | | |
| 2012/0130059 A1 | 5/2012 | Beria et al. | | |
| 2016/0166549 A1 * | 6/2016 | Melnick | ............... | A61K 31/53 514/369 |

FOREIGN PATENT DOCUMENTS

| | | | | |
|---|---|---|---|---|
| AU | 8767401 | * | 1/1987 | .......... C07D 417/04 |
| EP | 0245825 | | 11/1987 | |
| EP | 0245825 A1 | | 11/1987 | |
| WO | 2005021508 | | 3/2005 | |
| WO | WO2005/021508 A1 | | 3/2005 | |
| WO | 2007120842 | | 10/2007 | |
| WO | WO2007/120842 A2 | | 10/2007 | |
| WO | 2011094708 | | 8/2011 | |
| WO | WO2011/094708 A2 | | 8/2011 | |
| WO | 2014047232 | | 3/2014 | |
| WO | WO2014/047232 A2 | | 3/2014 | |
| WO | WO2014/117676 A1 | | 8/2014 | |
| WO | 2014117676 | | 8/2015 | |
| WO | 2016032127 | | 3/2016 | |

OTHER PUBLICATIONS

PubChem, Compound Summary for SID 238838036, Available Date: Feb. 13, 2015 [retrieved on Aug. 14, 2017]. Retrieved from the Internet: <URL: https://pubchem.ncbi.nlm.nih.gov/substance/238838036.
PubChem, Compound Summary for SID 105565194, Available Date: Feb. 22, 2011 [retrieved on Aug. 14, 2017]. Retrieved from the Internet: <URL: https://pubchem.ncbInim.nih.gov/substance/105565194.
PubChem, Compound Summary for SID 275735825, Available Date: Dec. 26, 2015 [retrieved on Aug. 14, 2017]. Retrieved from the Internet: < URL: https://pubchem.ncbi.nlm.nih.gov/substance/275735825.
Serhan, C. N.; Levy, B. Proc. Natl. Acad. Sci. U. S. A. 2003, 100, 8609.
Kudo, I.; Murakami, M. J. Biochem. Mol. Biol. 2005, 38, 633.
Fahmi, H. Current Opinion in Rheumatology 2004, 16, 623.
Park, J. Y.; Pillinger, M. H.; Abramson, S. B. Clinical Immunology 2006, 119, 229.
Murakami, M.; Nakatani, Y.; Tanioka, T.; Kudo, I. Prostaglandins Other Lipid Mediators 2002, 68-9, 383.

(Continued)

*Primary Examiner* — Erich A Leeser

(74) *Attorney, Agent, or Firm* — Stites & Harbison PLLC; Gary N. Stewart; Mandy Wilson Decker

(57) ABSTRACT

Compounds and compositions are provided that can inhibit microsomal prostaglandin E synthase-1 (mPGES-1). The compounds and compositions can reduce inflammation in a subject, such as inflammation caused by an inflammation disorder or symptoms thereof. Pharmaceutical compositions comprising the compound are also provided. Furthermore, methods are provided for reducing inflammation and/or inhibiting mPGES-1. The methods can comprise administering an effective amount of the composition to a subject.

10 Claims, 4 Drawing Sheets

(56) References Cited

OTHER PUBLICATIONS

Murakami, M.; Naraba, H.; Tanioka, T.; Semmyo, N.; Nakatani, Y.; Kojima, F.; Ikeda, T.; Fueki, M.; Ueno, A.; Oh-ishi, S.; Kudo, I. J. Biol. Chem. 2000, 275, 32783.
Uematsu, S.; Matsumoto, M.; Takeda, K.; Akira, S. Journal of Immunology 2002, 168, 5811.
Kamei, D.; Murakami, M.; Nakatani, Y.; Ishikawa, Y.; Ishii, T.; Kudo, I. Journal of Biological Chemistry 2003, 278, 19396.
Kamei, D.; Yamakawa, K.; Takegoshi, Y.; Mikami-Nakanishi, M.; Nakatani, Y.; Oh-ishi, S.; Yasui, H.; Azuma, Y.; Hirasawa, N.; Ohuchi, K.; Kawaguchi, H.; Ishikawa, Y.; Ishii, T.; Uematsu, S.; Akira, S.; Murakami, M.; Kudo, I. Journal of Biological Chemistry 2004, 279, 33684.
Ikeda-Matsuo, Y.; Ota, A.; Fukada, T.; Uematsu, S.; Akira, S.; Sasaki, Y. Proceedings of the National Academy of Sciences of the United States of America 2006, 103, 11790.
Murakami, M.; Kudo, I. Progress in Lipid Research 2004, 43, 3.
Claveau, D.; Sirinyan, M.; Guay, J.; Gordon, R.; Chan, C. C.; Bureau, Y.; Riendeau, D.; Mancini, J. A. Journal of Immunology 2003, 170, 4738.
Oshima, H.; Oshima, M.; Inaba, K.; Taketo, M. M. EMBO Journal 2004, 23, 1669.
Friesen, R. W.; Mancini, J. A. Journal of Medicinal Chemistry 2008, 51, 4059.
Samuelsson, B.; Morgenstern, R.; Jakobsson, P. J. Pharmacological Reviews 2007, 59, 207.
Scholich, K.; Geisslinger, G. Trends in Pharmacological Sciences 2006, 27, 399.
Cheng, Y.; Wang, M.; Yu, Y.; Lawson, J.; Funk, C. D.; FitzGerald, G. A. Journal of Clinical Investigation 2006, 116, 1391.
Engblom, D.; Saha, S.; Engstrom, L.; Westman, M.; Audoly, L. P.; Jakobsson, P. J.; Blomqvist, A. Nature Neuroscience 2003, 6, 1137.
Trebino, C. E.; Stock, J. L.; Gibbons, C. P.; Naiman, B. M.; Wachtmann, T. S.; Umland, J. P.; Pandher, K.; Lapointe, J. M.; Saha, S.; Roach, M. L.; Carter, D.; Thomas, N. A.; Durtschi, B. A.; McNeish, J. D.; Hambor, J. E.; Jakobsson, P. J.; Carty, T. J.; Perez, J. R.; Audoly, L. P. Proceedings of the National Academy of Sciences of the United States of America 2003, 100, 9044.
Thoren, S.; Jakobsson, P. J. Eur. J. Biochem. 2000, 267, 6428.
Mancini, J. A.; Blood, K.; Guay, J.; Gordon, R.; Claveau, D.; Chan, C. C.; Riendeau, D. J. Biol. Chem. 2001, 276, 4469.
Riendeau, D.; Aspiotis, R.; Ethier, D.; Gareau, Y.; Grimm, E. L.; Guay, J.; Guiral, S.; Juteau, H.; Mancini, J. A.; Methot, N.; Rubin, J.; Friesen, R. W. Bioorg. Med. Chem. Lett. 2005, 15, 3352.
De Simone, R.; Chini, M. G.; Bruno, I.; Riccio, R.; Mueller, D.; Werz, O.; Bifulco, G. Journal of Medicinal Chemistry 2011, 54, 1565.
Quraishi, O.; Mancini, J. A.; Riendeau, D. Biochem. Pharmacol. 2002, 63, 1183.
Lu, J.; Wu, L.; Jiang, J.; Zhang, X., Helical Nanostructures of an Optically Active Metal-Free Porphyrin with Four Optically Active Binaphthyl Moieties: Effect of Metal-Ligand Coordination on the Morphology. European Journal of Inorganic Chemistry 2010, 2010 (25), 4000-4008.
Saari, W. S.; Schwering, J. E.; Lyle, P. A.; Smith, S. J.; Engelhardt, E. L., Cyclization-activated prodrugs. Basic carbamates of 4-hydroxyanisole. Journal of medicinal chemistry 1990, 33 (1), 97-101.
Baron, R.; Huang, C. H.; Bassani, D. M.; Onopriyenko, A.; Zayats, M.; Willner, I., Hydrogen-bonded CdS nanoparticle assemblies on electrodes for photoelectrochemical applications. Angewandte Chemie 2005, 44 (26), 4010-5.
Hidalgo-Figueroa, S.; Ramirez-Espinosa, J. J.; Estrada-Soto, S.; Almanza-Perez, J. C.; Roman-Ramos, R.; Alarcon-Aguilar, F. J.; Hernandez-Rosado, J. V.; Moreno-Diaz, H.; Diaz-Coutino, D.; Navarrete-Vazquez, G., Discovery of thiazolidine-2,4-dione/ biphenylcarbonitrile hybrid as dual PPAR alpha/gamma modulator with antidiabetic effect: in vitro, in silico and in vivo approaches. Chemical biology & drug design 2013, 81 (4), 474-83.
Yan, Q.; Cao, R.; Yi, W.; Chen, Z.; Wen, H.; Ma, L.; Song, H., Inhibitory effects of 5-benzylidene barbiturate derivatives on mushroom tyrosinase and their antibacterial activities. European journal of medicinal chemistry 2009, 44 (10), 4235-43.
Komiya, M.; Asano, S.; Koike, N.; Koga, E.; Igarashi, J.; Nakatani, S.; Isobe, Y., Structure and activity relationship of 2-(substituted benzoyl)-hydroxyindoles as novel CaMKII inhibitors. Bioorganic & medicinal chemistry letters 2011, 21 (5), 1456-8.
Chen, H.; Tsalkova, T.; Chepurny, O. G.; Mei, F. C.; Holz, G. G.; Cheng, X.; Zhou, J., Identification and characterization of small molecules as potent and specific EPAC2 antagonists. Journal of medicinal chemistry 2013, 56 (3), 952-62.
Murugan, R.; Anbazhagan, S.; Lingeshwaran; Sriman Narayanan, S., Synthesis and in vivo antidiabetic activity of novel dispiropyrrolidines through [3+2] cycloaddition reactions with thiazolidinedione and rhodanine derivatives. European journal of medicinal chemistry 2009, 44 (8), 3272-9.
Shibinskaya, M. O.; Lyakhov, S. A.; Mazepa, A. V.; Andronati, S. A.; Turov, A. V.; Zholobak, N. M.; Spivak, N. Y., Synthesis, cytotoxicity, antiviral activity and interferon inducing ability of 6-(2-aminoethyl)-6H-indolo[2,3-b]quinoxalines. European journal of medicinal chemistry 2010, 45 (3), 1237-43.
Yamamoto, Y.; Yohda, M.; Shirai, T.; Ito, H.; Miyaura, N., Me-BIPAM for the synthesis of optically active 3-aryl-3-hydroxy-2-oxindoles by ruthenium-catalyzed addition of arylboronic acids to isatins. Chemistry, an Asian journal 2012, 7 (10), 2446-9.
Kaila, N.; Janz, K.; Huang, A.; Moretto, A.; DeBernardo, S.; Bedard, P. W.; Tam, S.; Clerin, V.; Keith, J. C., Jr.; Tsao, D. H.; Sushkova, N.; Shaw, G. D.; Camphausen, R. T.; Schaub, R. G.; Wang, Q., 2-(4-Chlorobenzyl)-3-hydroxy-7,8,9,10-tetrahydrobenzo[H]quinoline-4-carboxylic acid (PSI-697): identification of a clinical candidate from the quinoline salicylic acid series of P-selectin antagonists. Journal of medicinal chemistry 2007, 50 (1), 40-64.
Yamazaki, K.; Kaneko, Y.; Suwa, K.; Ebara, S.; Nakazawa, K.; Yasuno, K., Synthesis of potent and selective inhibitors of Candida albicans N-myristoyltransferase based on the benzothiazole structure. Bioorganic & medicinal chemistry 2005, 13 (7), 2509-22.
Xie, J.; Seto, C. T., A two stage click-based library of protein tyrosine phosphatase inhibitors. Bioorganic & medicinal chemistry 2007, 15 (1), 458-73.
Cumpstey, I.; Carlsson, S.; Leffler, H.; Nilsson, U. J., Synthesis of a phenyl thio-beta-D-galactopyranoside library from 1,5-difluoro-2,4-dinitrobenzene: discovery of efficient and selective monosaccharide inhibitors of galectin-7. Organic & biomolecular chemistry 2005, 3 (10), 1922-32.
Shete, D.K., et al., Comparative efficiency of metal phosphates as a protomer in multi-component condensation reaction. Pharm. Lett., 2010. 2(3): p. 59-65.
De Vasconcelos, A., et al., Antioxidant capacity and environmentally friendly synthesis of dihydro-(2H)-pyrimidinones promoted by naturally occurring organic acids. J. Biochem. Mol. Toxicol., 2012. 26(4): p. 155-161.
Rathelot, P., et al., 1,3-Diphenylpyrazoles: synthesis and antiparasitic activities of azomethine derivatives. European Journal of Medicinal Chemistry, 2002. 37(8): p. 671-679.
Stella, A., et al., Synthesis of a 2,4,6-trisubstituted 5-cyano-pyrimidine library and evaluation of its immunosuppressive activity in a Mixed Lymphocyte Reaction assay. Bioorg. Med. Chem., 2013. 21(5): p. 1209-1218.
Sasaki Yuka, et al., "Role of microsomal prostaglandin E synthase-1 (mPGES-1)-derived prostaglandin E2in colon carcinogenesis," Prostaglandins and Other Lipid Mediators, vol. 121 , pp. 42-45.
Dallaporta, M. et al., "Towards the management of Inflammation: Recent Developments of mPGES-1 Inhibitors," Recent Patents on CNS Drug Discovery, vol. 5, 2010, pp. 70-80.
Masako Nakanishi, et al., "m PGES-1 as a target for cancer suppression," Biochimie, vol. 92, No. 6, Jun. 1, 2010, pp. 660-664.
Hui-Hua Chang, et al., "Identification and development of m PGES-1 inhibitors: where we are at?," Future Medicinal Chemistry, vol. 3, No. 15, Nov. 1, 2011 pp. 1909-1934.
Second Office Action for Chinese Patent Application No. 201780040636.0 issued May 23, 2022 (Untranslated).

(56) References Cited

OTHER PUBLICATIONS

Second Office Action for Chinese Patent Application No. 201780040636.0 issued May 23, 2022 (Translated).
Lecca, et al., "Neuroprotective and anti-inflammatory properties of a novel non-thiazolidinedione PPARγ agonist in vitro and in MPTP-treated mice," Neuroscience (Amsterdam, Netherlands), vol. 302, 23-35 (Apr. 20, 2015).
Maurer, et al., "Inhibitors of the NAD+-Dependent Protein Desuccinylase and Demalonylase Sirt5", Benjamin Maurer, et al., ACS Medicinal Chemistry Letters, vol. 3, No. 12, 1050-1053 (Oct. 6, 2012).
Decision of Rejection for Chinese Patent Application No. 201780040636.0 issued Jul. 29, 2022 (Untranslated).
Decision of Rejection for Chinese Patent Application No. 201780040636.0 issued Jul. 29, 2022 (Translated).
First Examination Report for European Patent Application No. 17821160.3-1110 issued May 17, 2021.
International Search Report for International Application No. PCT/US2017/039785 issued Dec. 4, 2017.
PubChem, Compound Summary for SID 238838036, Available Date: Feb. 13, 2015 available at https://pubchem.ncbi.nlm.nih.gov/substance/238838036.
PubChem, Compound Summary for SID 105565194, Available Date: Feb. 13, 2015 available at https://pubchem.ncbi.nlm.nih.gov/substance/105565194.
PubChem, Compound Summary for SID 275735825, Available Date: Dec. 26, 2015 available at https://pubchem.ncbi.nlm.nih.gov/substance/275735825.
Dallaporta, M. et al., "Towards the management of Inflammataion: Recent Developments of mPGES-1 Inhibitors," Recent Patents on CNS Drug Discovery,vol. 5, 2010, pp. 70-80.
International Preliminary Report on Patentability for International Application No. PCT/US2017/039785 issued Dec. 4, 2017.
Second Examination Report for European Patent Application No. 17821160.3-1110 issued Jun. 7, 2022.
Extended European Search Report for 17821160.3-1110 issued on Mar. 16, 2020.
Examination Report for European Application No. 17821160.3-1110 issued Dec. 13, 2022.
Office Action for Chinese Patent Application No. 201780040636 issued Dec. 13, 2021 (Untranslated and Including list of STN-Registry Database compounds).
Office Action for Chinese Patent Application No. 201780040636 issued Dec. 13, 2021 (Machine Translated).
American Chemical Society, Registration No. 866817-23-4, Nov. 6, 2005 (cited in Office Action for Chinese Patent Application No. 201780040636 and included in listing of STN-Registry Database compounds provided therewith).
American Chemical Society, Registration No. 524704-24-3, Jun. 3, 2003 (cited in Office Action for Chinese Patent Application No. 201780040636 and included in listing of STN-Registry Database compounds provided therewith).
American Chemical Society, Registration No. 357648-58-9, Sep. 20, 2001 (cited in Office Action for Chinese Patent Application No. 201780040636 and included in listing of STN-Registry Database compounds provided therewith).
American Chemical Society, Registration No. 357648-54-5, Sep. 20, 2001 (cited in Office Action for Chinese Patent Application No. 201780040636 and included in listing of STN-Registry Database compounds provided therewith).
American Chemical Society, Registration No. 330561-81-4, Apr. 9, 2001 (cited in Office Action for Chinese Patent Application No. 201780040636 and included in listing of STN-Registry Database compounds provided therewith).
Fourth Examination Report for European Patent Application 17821160.3-1110 Issued Dec. 5, 2023.

* cited by examiner

Preparation of 2,4-thiazolidinedione N-acetic acid

Preparation of 1,5-disubstituted isation

Preparation of 1,5-disubstituted isation

Coupling of isatin and 2,4-thiazolidinedione moieties

PROSTAGLANDIN E SYNTHASE INHIBITORS AND METHODS FOR UTILIZING THE SAME

RELATED APPLICATIONS

This application is a division of U.S. patent application Ser. No. 16/305,386, filed Nov. 28, 2018, which is a national stage entry of PCT/US2017/039785, filed Jun. 28, 2017, which claims the benefit of U.S. Provisional Application Ser. No. 62/355,739, filed Jun. 28, 2016, the entire disclosure of each of which is incorporated herein by this reference.

TECHNICAL FIELD

The presently-disclosed subject matter relates to prostaglandin E synthase (PGES) inhibitors, and in particular, microsomal PGES-1 (mPGES-1) inhibitors. Embodiments of the presently-disclosed subject matter also relate to methods of utilizing mPGES-1 inhibitors to treat inflammatory disorders in a subject in need thereof.

BACKGROUND

Prostaglandin $E_2$ (PGE$_2$) is one of the most important prostanoids with diverse biological activity.[1] The biosynthetic pathway of PGE$_2$ has been well characterized and involves three sequential enzymatic actions.[2] The first step in this pathway, involves the release of arachidonic acid (AA) from the membrane, by the action of phospholipase $A_2$ (PLA$_2$).[2] This is followed by the conversion of AA to prostaglandin $H_2$ (PGH$_2$) by the action of cyclooxygenase COX-1 or COX-2.[2] Finally, PGH$_2$ is converted to PGE$_2$ by the action of terminal prostaglandin E synthase (PGES) enzymes,[3] particularly microsomal PGES-1 (mPGES-1).[4] It has been known that mPGES-1 couples with COX-2[5-6] and plays a key role in a number of disease conditions, including inflammation, arthritis, fever, pain, cancer, stroke, and bone disorders.[7-13] Human mPGES-1 has been recognized as a promising target of next-generation therapeutics for the above diseases.[14]

Currently available non-steroidal anti-inflammatory drugs (NSAIDs) inhibit either cyclooxygenase (COX)-1 or COX-2 or both.[15] These inhibitors have several deleterious side effects including ulcers, bleeding within the gastrointestinal tract, or increased risk of cardiovascular events.[16] The withdrawal of rofecoxib (Vioxx) due to side effects further highlights the need to develop improved, safer anti-inflammatory drugs.[15] The COX inhibitors prevent the production of all prostaglandins downstream of PGH$_2$, which results in a lot of problems. For example, blocking the production of prostaglandin-$I_2$ (PGI$_2$) has been reported to play a role in cardiovascular events.[17] Unlike COX inhibition, inhibition of terminal mPGES-1 will only block the production of PGE$_2$ without affecting the normal production of other prostaglandins including PGI$_2$. Reported knock-out studies identified mPGES-1 as a central switch in pyresis.[18] The mPGES-1 knock-out studies also revealed a decrease in inflammatory response in a collagen-induced arthritis model.[19] In contrast to COX-2, mPGES-1-deficient mice were reported to be viable, fertile and have normal phenotype.[19] Ischemic stroke induced in mPGES-1 null mice was reported to show significant reduction in the infarct size and volume.[10, 14] Thus, mPGES-1 inhibitors are expected to retain the anti-inflammatory effect as COX inhibitors without the side effects of COX inhibitors.

Although mPGES-1 inhibitors are expected to be potentially valuable therapeutic agents, few inhibitors of mPGES-1 were identified in experimental screening efforts. The COX-2 inhibitor NS-398, 5-Lipoxygenase activating protein (FLAP) inhibitor MK-886, and the active metabolite of another NSAID sulindac, were found to inhibit mPGES-1 with an IC$_{50}$ of 20, 1.6, and 80 µM, respectively.[20-21,22] Leukotriene C4 was reported to inhibit mPGES-1 with micromolar IC$_{50}$, probably by competing with glutathione (GSH).[20] In addition to small molecules,[23] several polyunsaturated fatty acids and stable analogs of PGE$_2$ were reported to inhibit mPGES-1.[24] Riendeau[22] recently reported a series of mPGES-1 inhibitors synthesized based on the scaffold of MK-886 (FLAP inhibitor). Unfortunately, all of these inhibitors are not sufficiently potent against mPGES-1 in the tested living cells.

Thus, there remains a need for novel compounds that more potently inhibit mPGES-1. There also remains a need for methods of treating inflammatory disorders that do not have the problems discussed above. However, known mPGES-1 inhibitors are not sufficiently potent, and known anti-inflammatory agents are associated with many adverse side effects, such as ulcers and gastrointestinal bleeding. Hence, novel compounds that more potently inhibit mPGES-1 activity and are thereby able to treat inflammatory disorders are highly desired.

SUMMARY

The presently-disclosed subject matter meets some or all of the above-identified needs, as will become evident to those of ordinary skill in the art after a study of information provided in this document.

This summary describes several embodiments of the presently-disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this summary or not. To avoid excessive repetition, this summary does not list or suggest all possible combinations of such features.

In some embodiments, the presently-disclosed subject matter includes a compound of the formula:

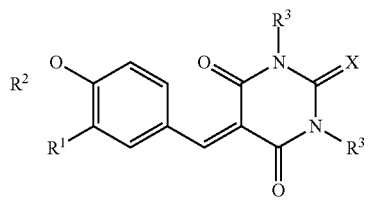

or pharmaceutically acceptable salts thereof; wherein $R^1$ is selected from the group consisting of H, halide, Me, OMe, OEt, NO$_2$, OH, and, together with the ring to which it is attached, a bicyclic ring system; wherein $R^2$ is alkyl; wherein $R^3$ is selected from the group consisting of H and Me; and wherein X is selected from the group consisting of O or S. In one embodiment, $R^1$ is selected from the group consisting of: H, Cl, Br, I, Me, OMe, OEt, NO$_2$, OH, and, taken together with the ring to which it is attached, a bicyclic ring system. In another embodiment, R² is selected from the group consisting of:
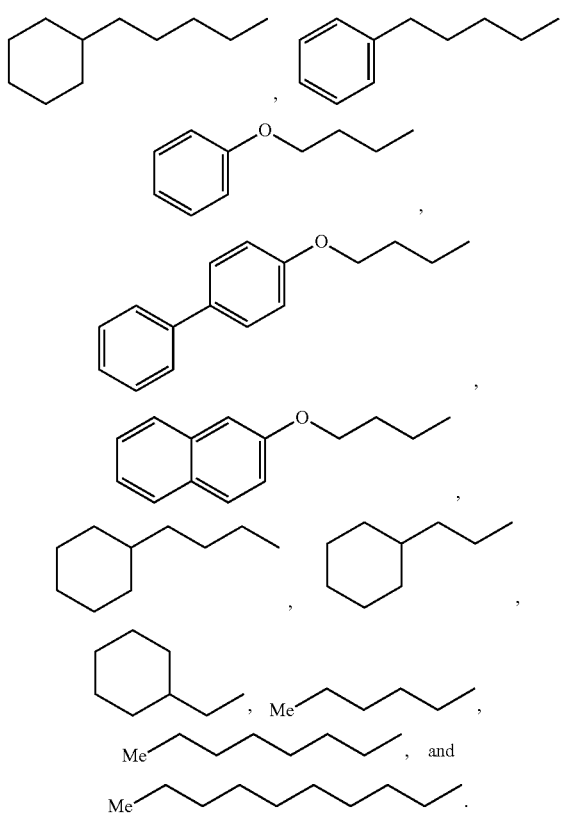
In a further embodiment, the compound includes the formula selected from the group consisting of:
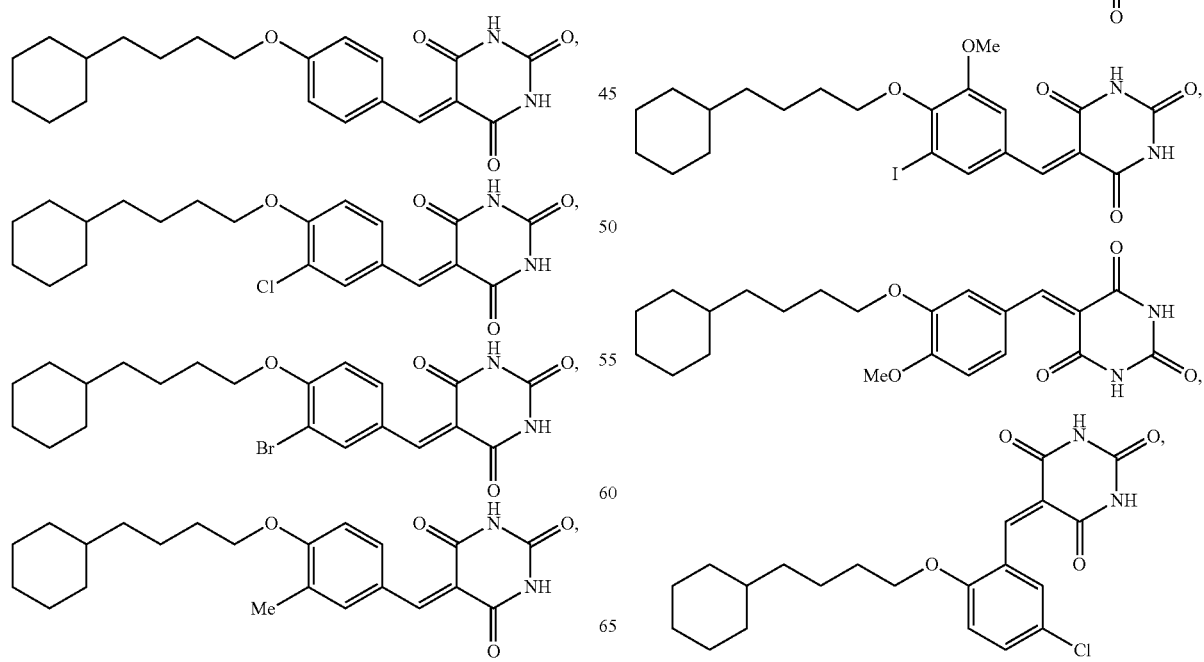
-continued
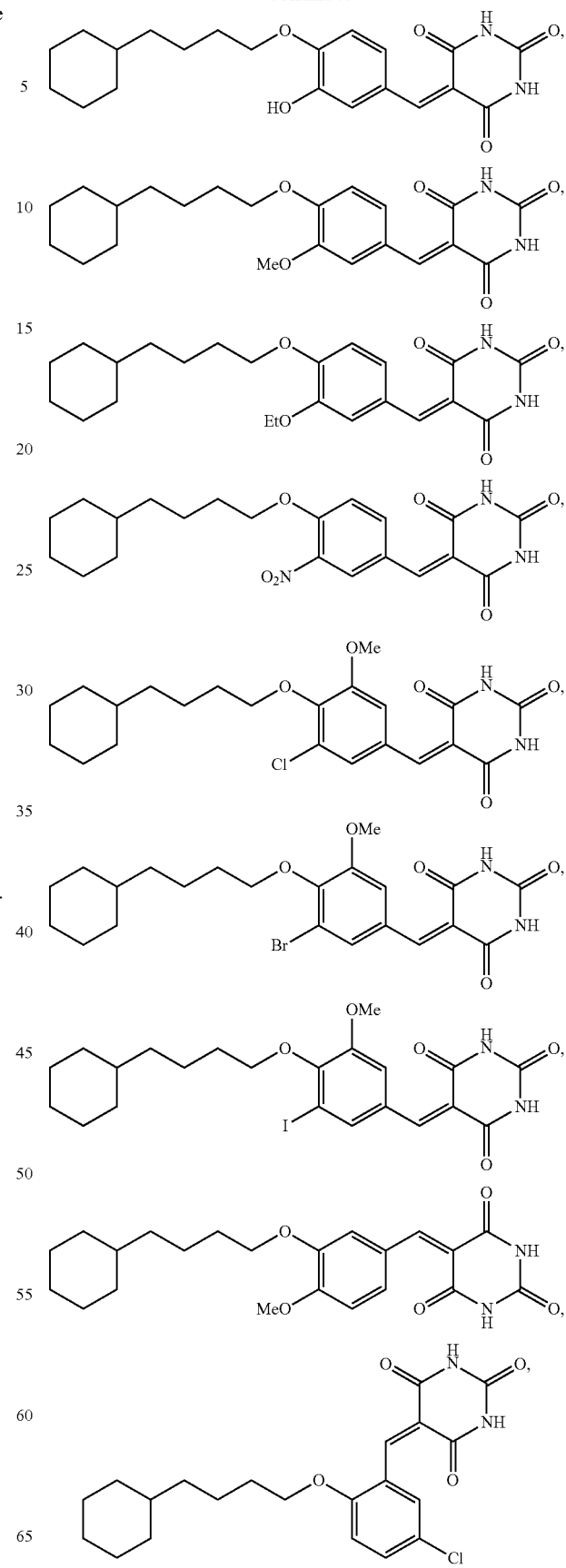

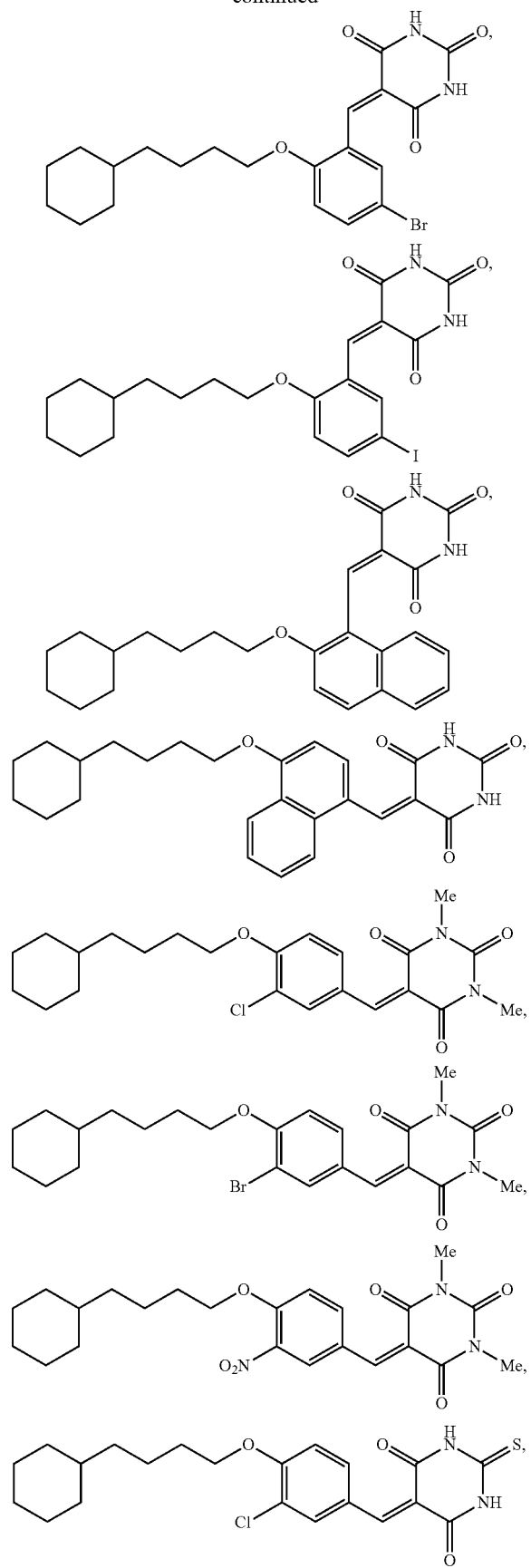
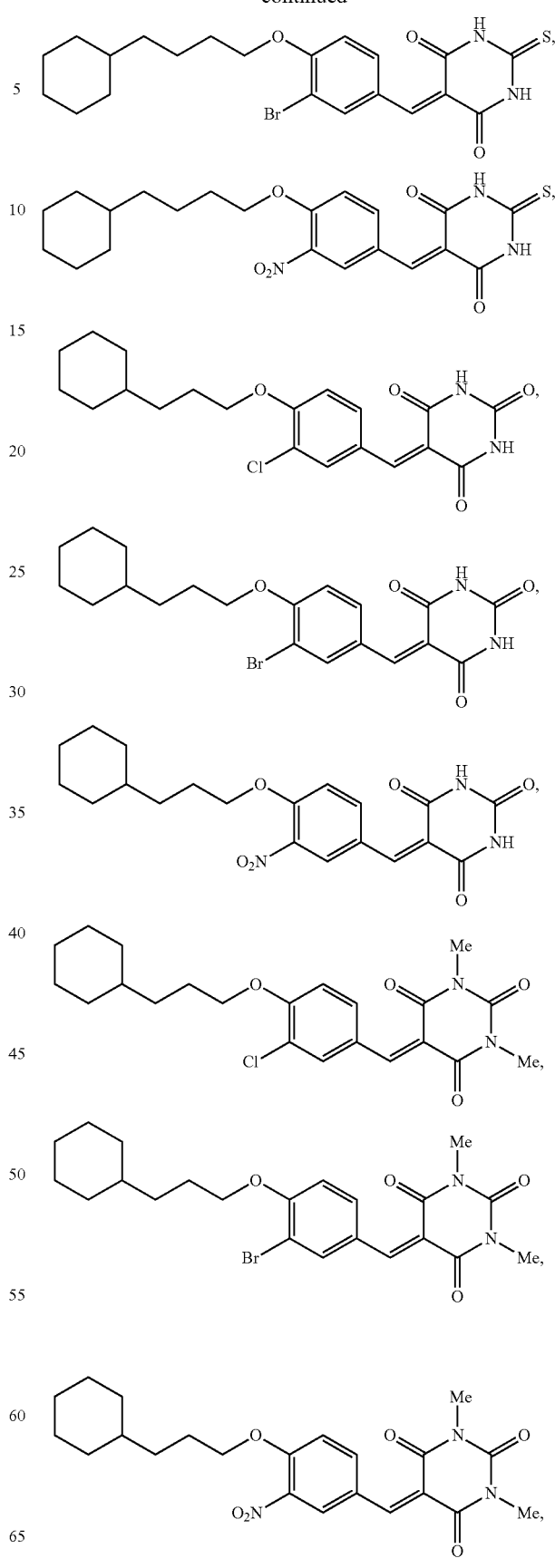

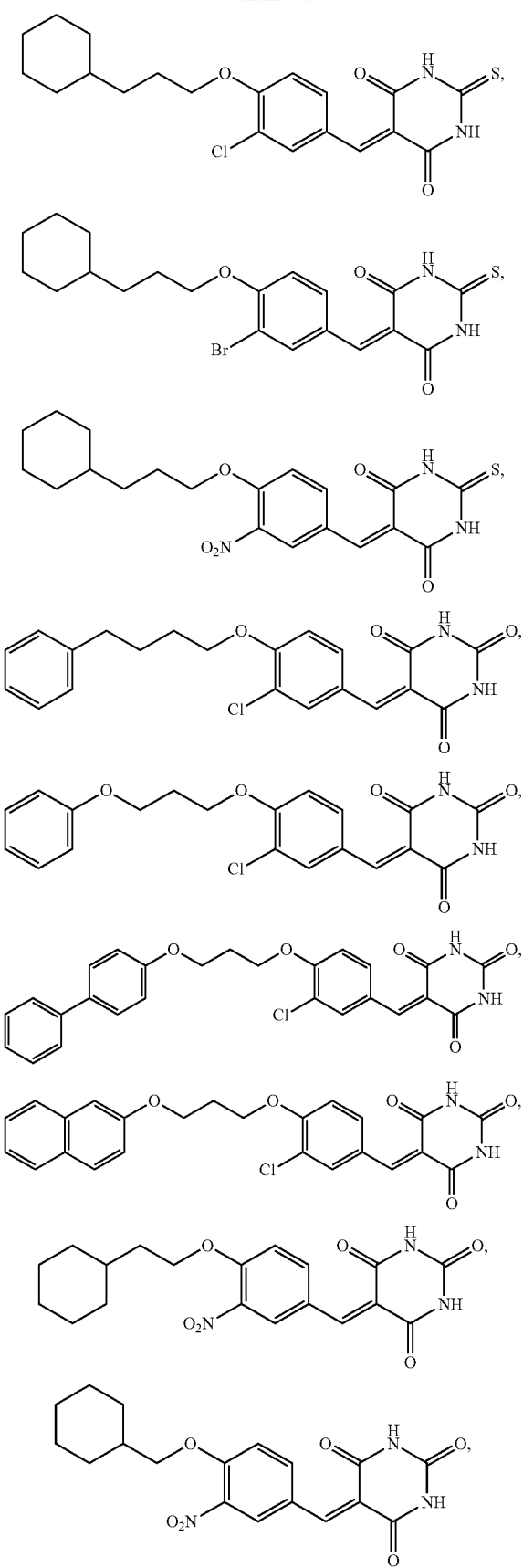

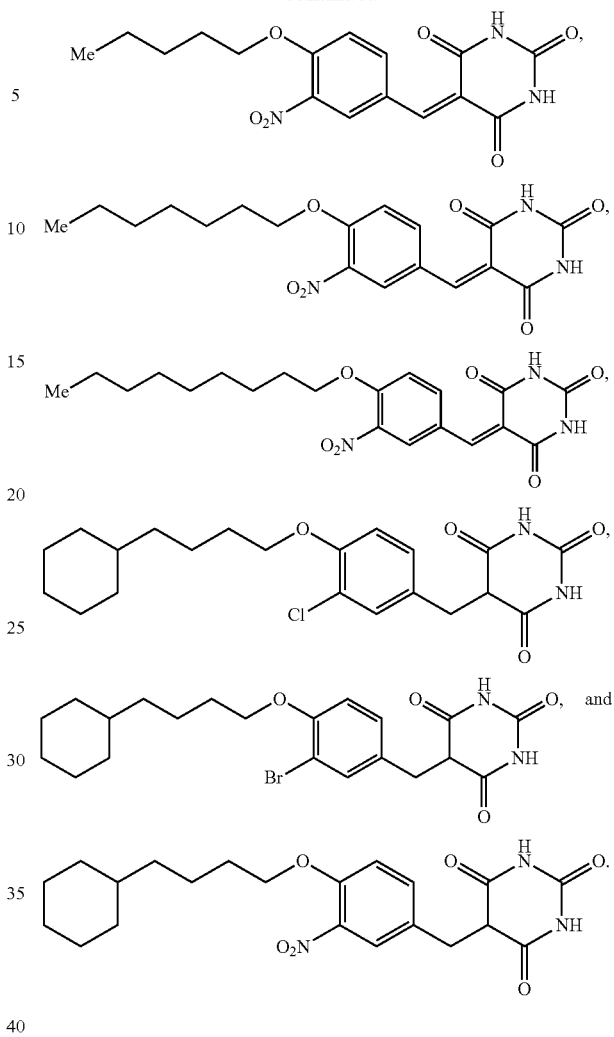

In some embodiments, the presently-disclosed subject matter includes a compound of the formula:

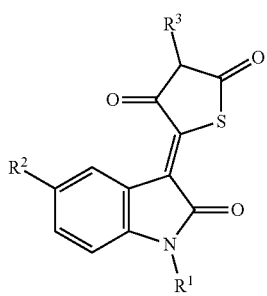

or pharmaceutically acceptable salts thereof, wherein $R^1$ is selected from the group consisting of H, an alkyl, an alkyl halide, an ether, and a carboxylic acid; wherein $R^2$ is selected from the group consisting of H, a halide, an alkyne, and an aromatic; and wherein $R^3$ is selected from the group consisting of H, a carboxyl, a carboxylic acid, and an alkyl. In one embodiment, $R^1$ is selected from the group consisting of:

H,
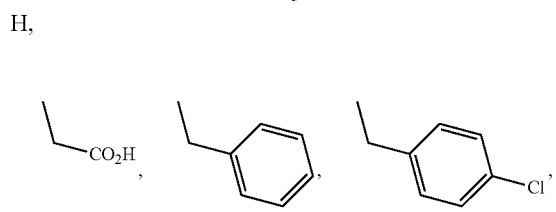
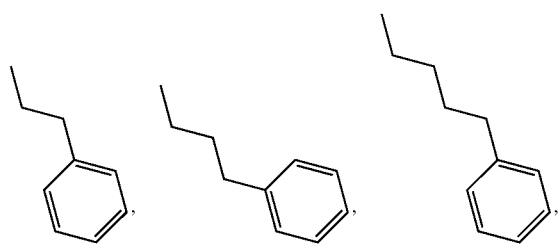
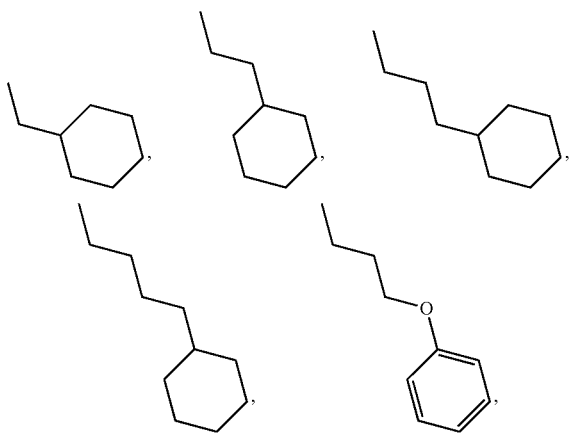
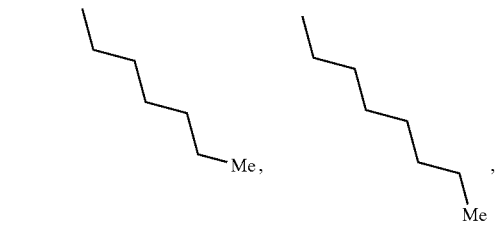
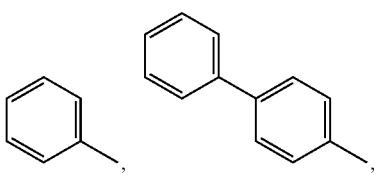
-continued
In another embodiment, $R^2$ is selected from the group consisting of:
H,
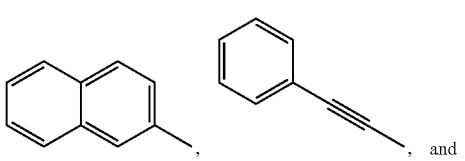
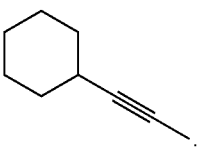
In a further embodiment, $R^3$ is selected from the group consisting of:
H,
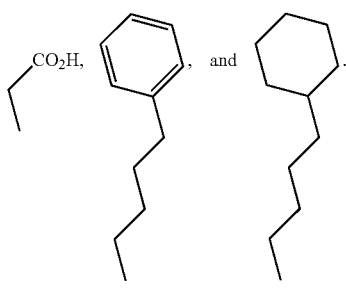

In some embodiments, the compound includes the formula selected from the group consisting of:
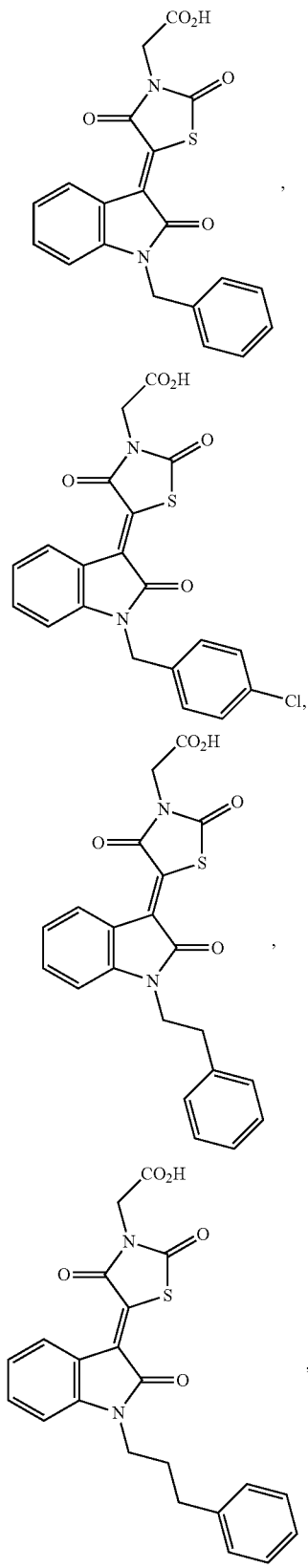
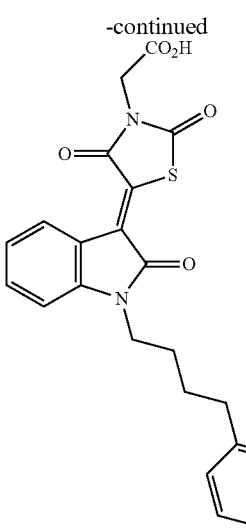

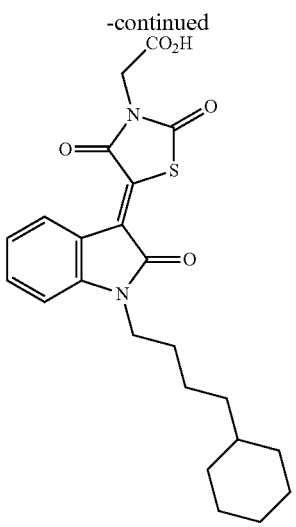
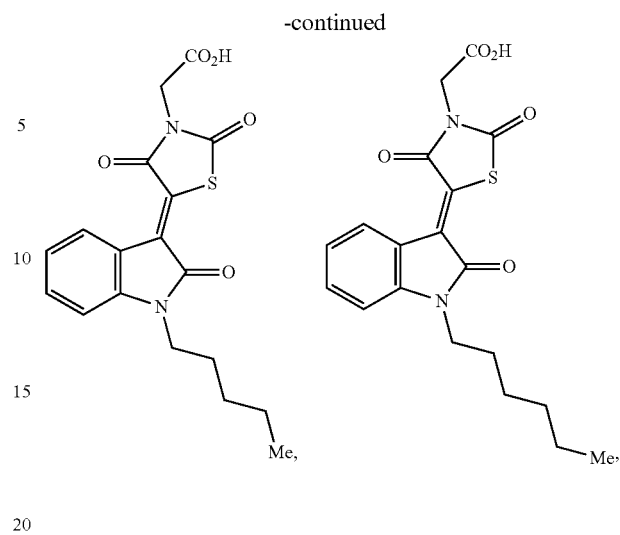
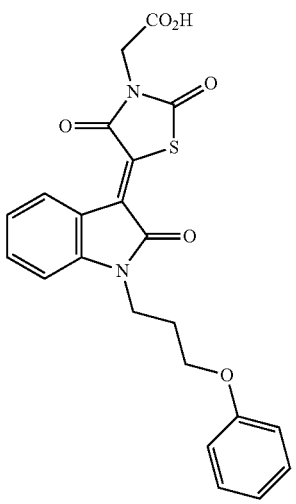
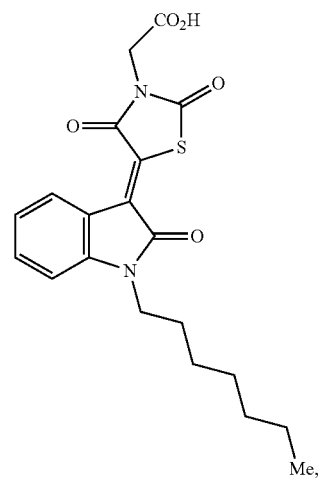
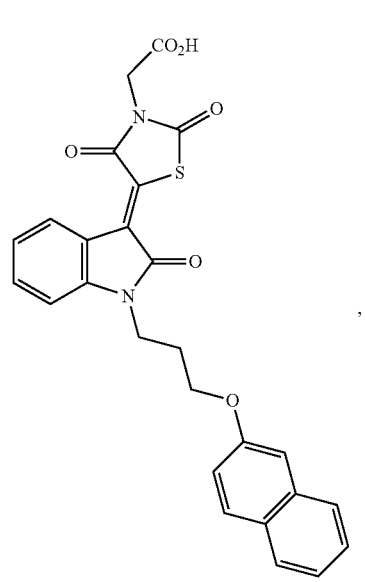
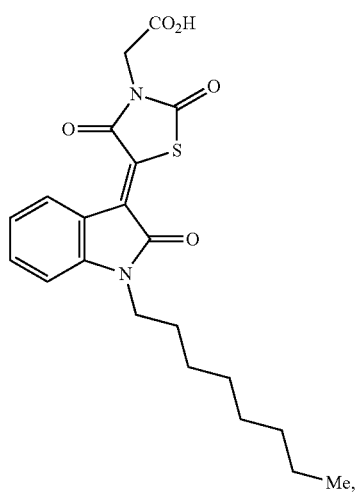

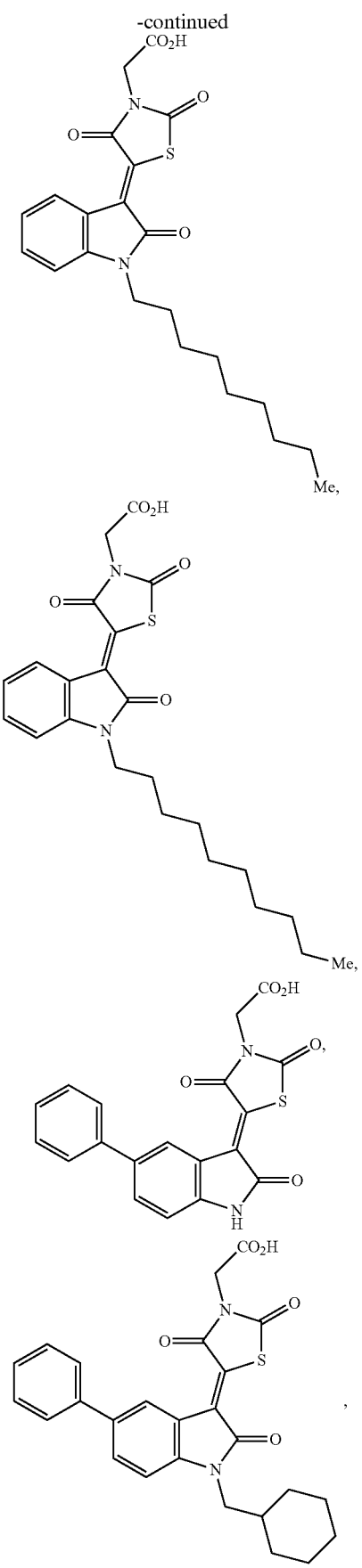
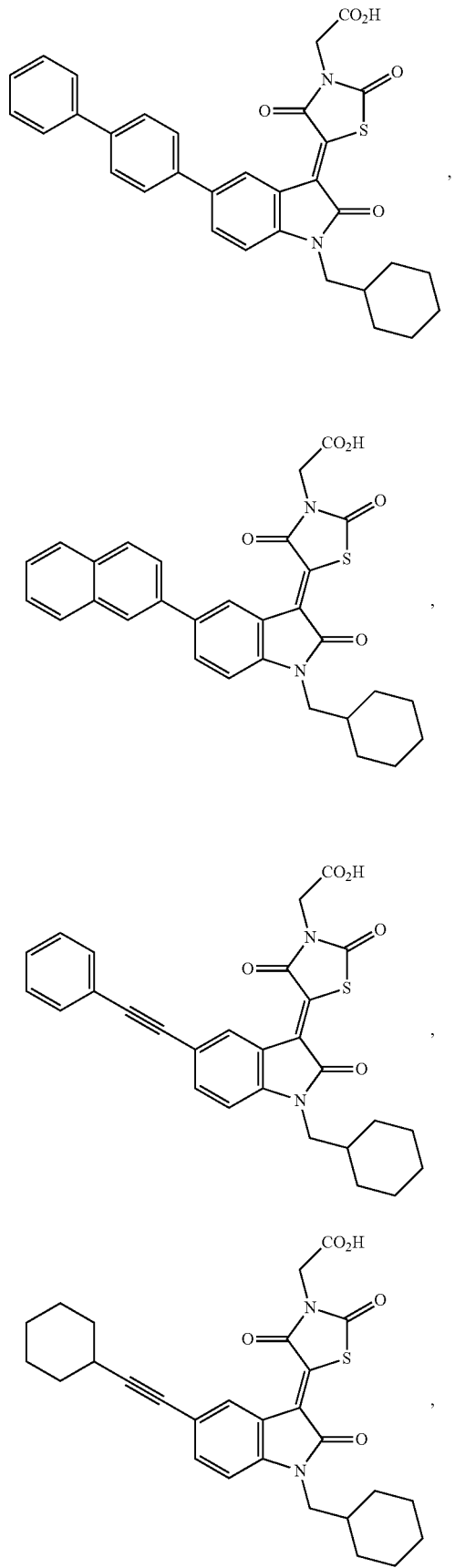

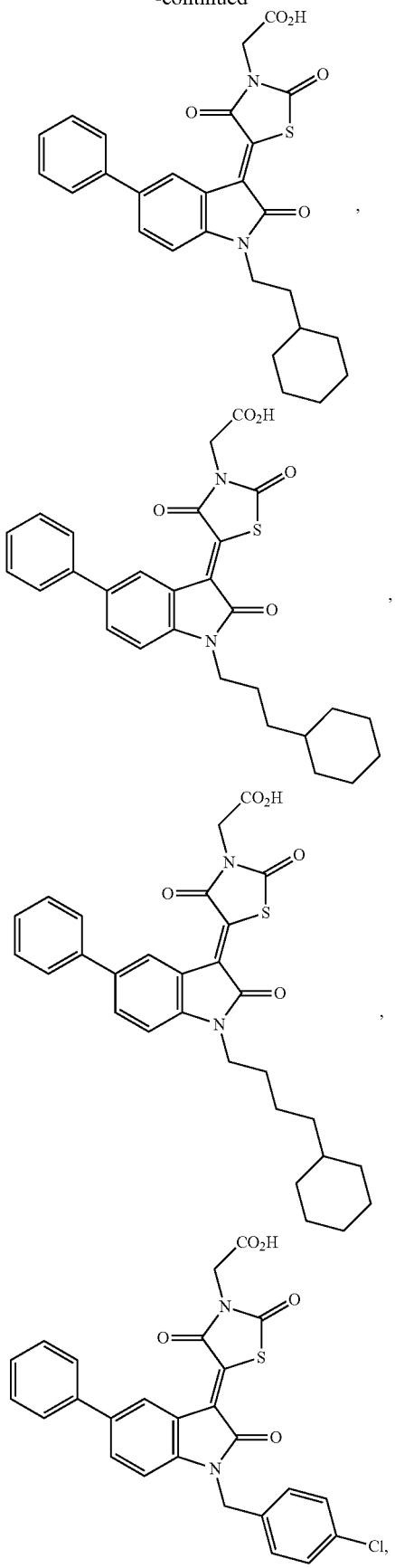
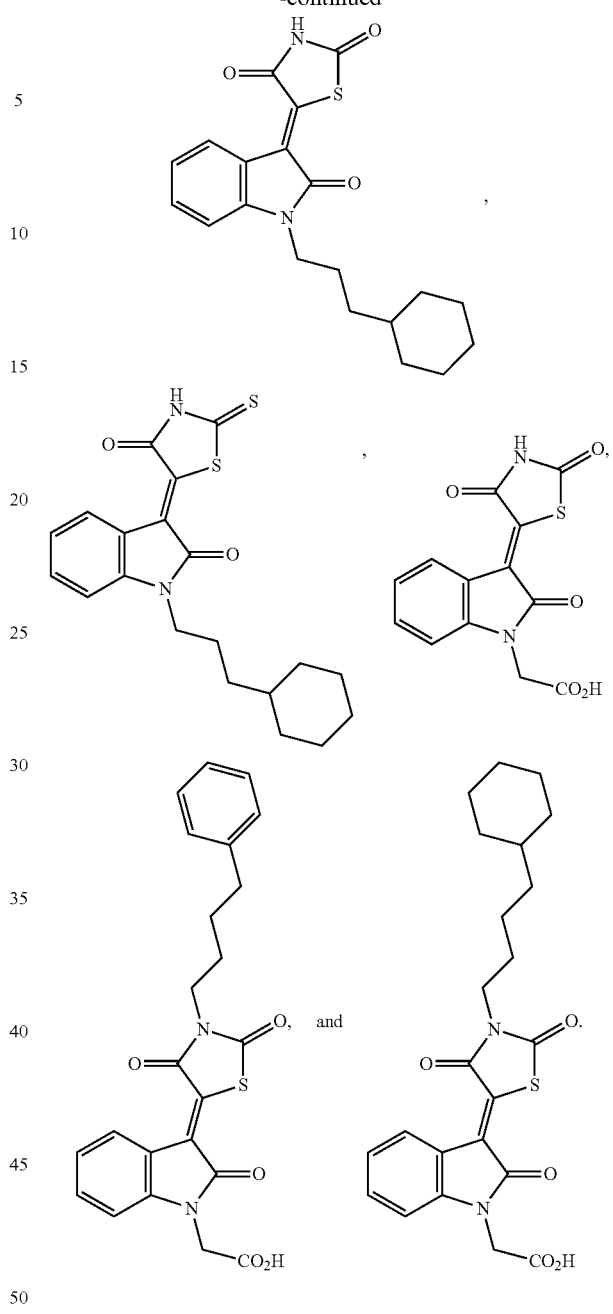
In some embodiments, the presently-disclosed subject matter includes a compound of the formula:
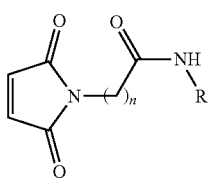
or pharmaceutically acceptable salts thereof, wherein R is selected from the group consisting of an alkyl and an alkoxy; and wherein n is from 1 to 6. In one embodiment, R is selected from the group consisting of:

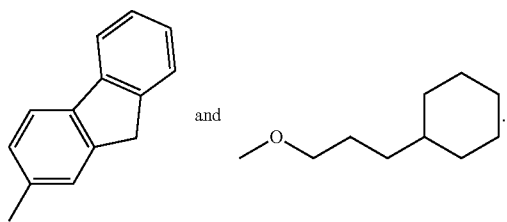

In another embodiment, the compound has the formula selected from the group consisting of:

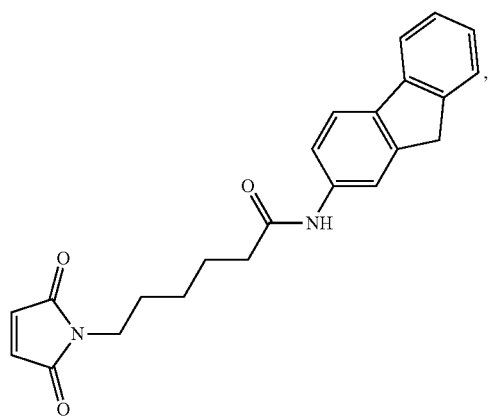

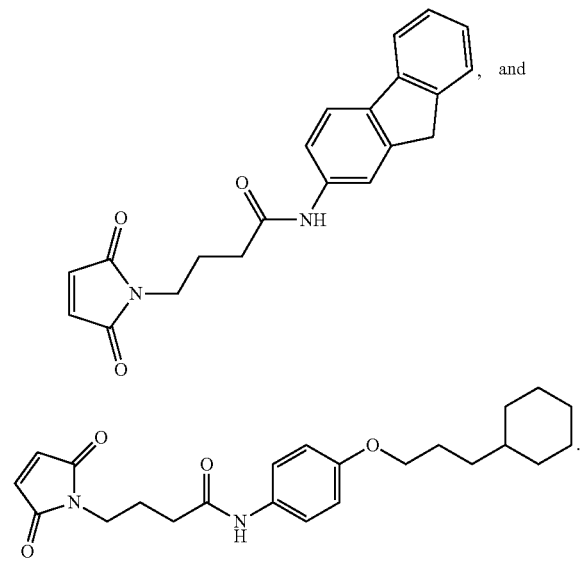

In some embodiments, the presently-disclosed subject matter includes a compound of the formula:

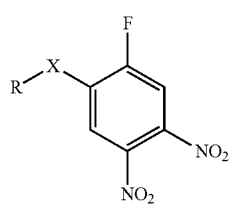

or pharmaceutically acceptable salts thereof, wherein R is a substituted phenyl; and wherein X is O. In one embodiment, the compound is of the formula:

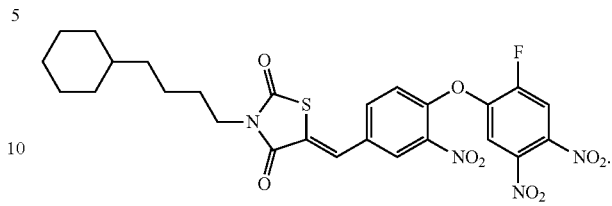

In some embodiments, the presently-disclosed subject matter includes a compound of the formula:

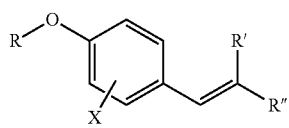

or pharmaceutically acceptable salts thereof, wherein R is selected from the group consisting of an aliphatic side chain and an alkyl; wherein X is selected from the group consisting of H, $NO_2$, Br, and OMe; and wherein R' and R" are independently selected from the group consisting of CN, COOH, COOEt, $CONH_2$, and $NO_2$. In one embodiment, the compound is of the formula:

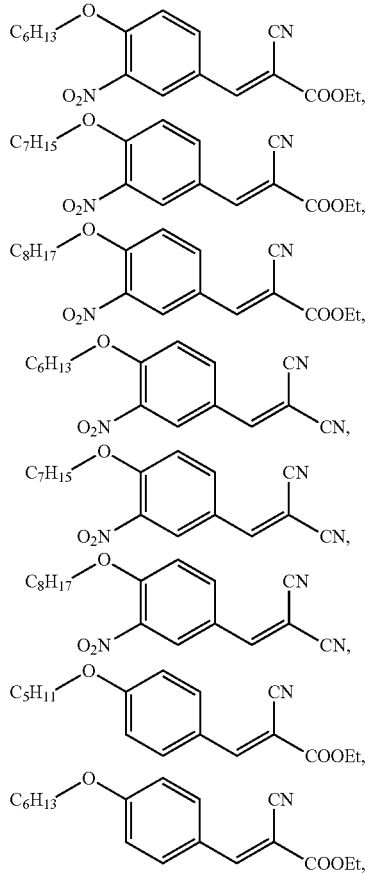

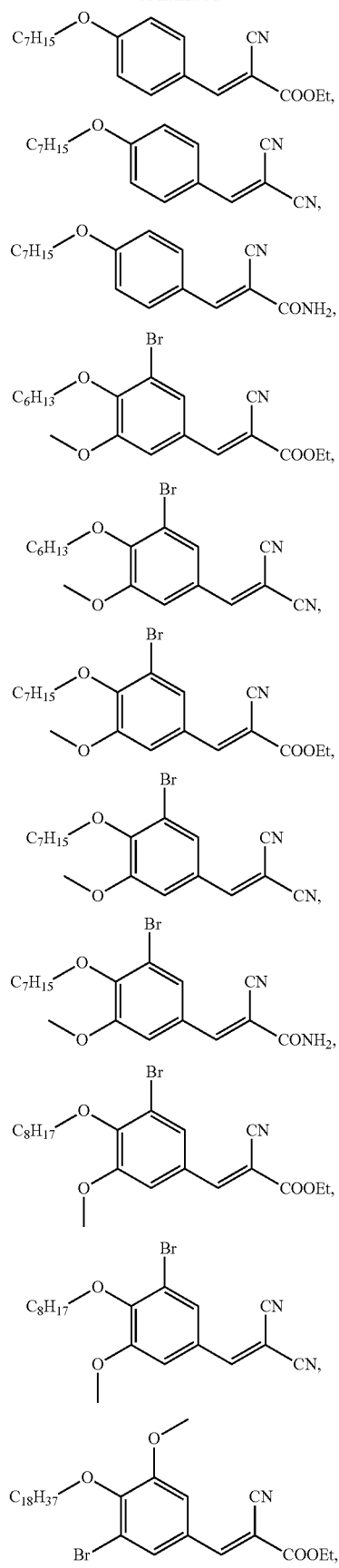
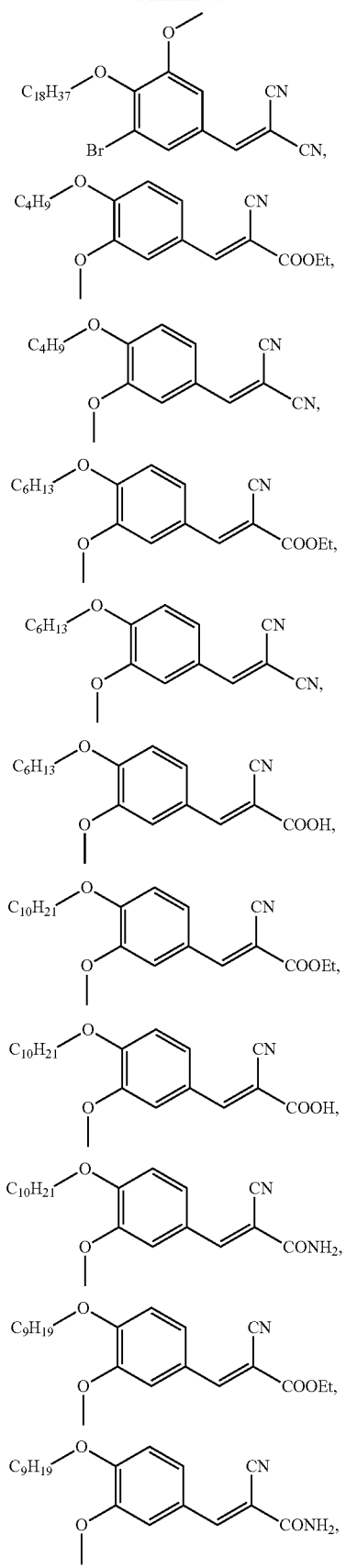

-continued

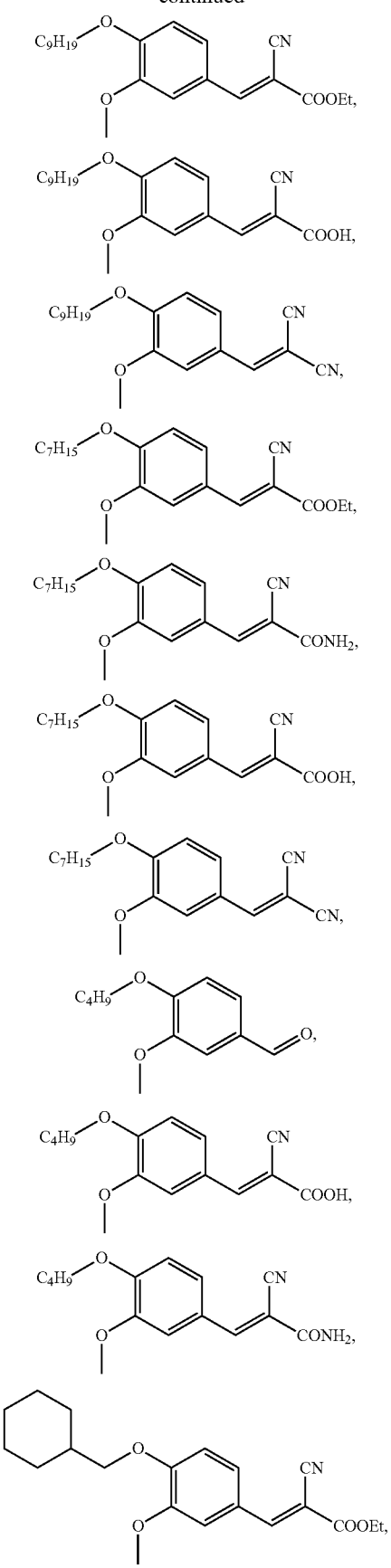

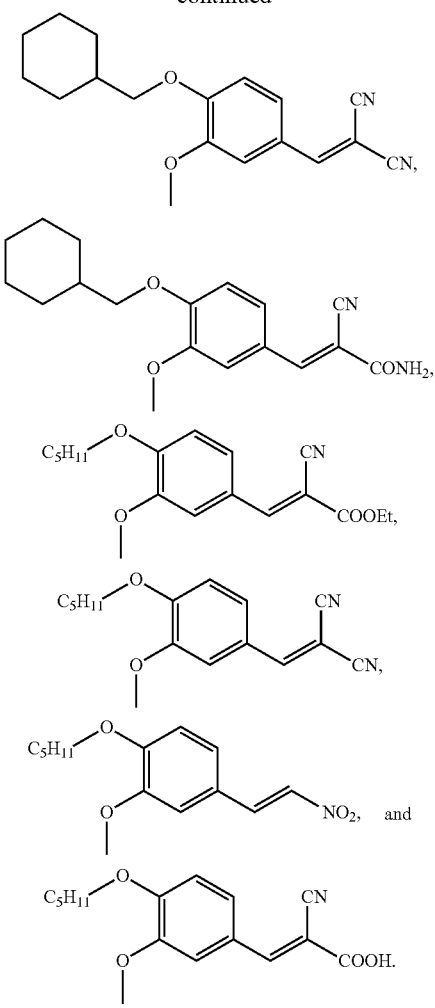

In some embodiments, the presently-disclosed subject matter includes a compound of the formula:

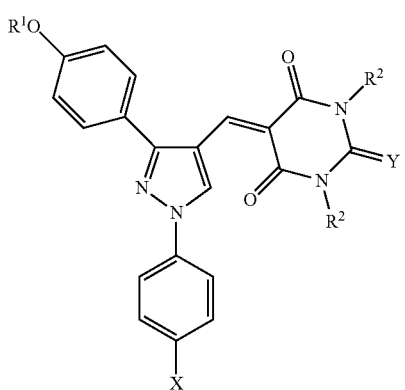

or pharmaceutically acceptable salts thereof, wherein $R^1$ is an alkyl; wherein each $R^2$ is independently selected from the group consisting of H and an alkyl; wherein X is selected from the group consisting of H and a halogen; and wherein Y is selected from the group consisting of S and O. In one embodiment, the compound is of the formula:

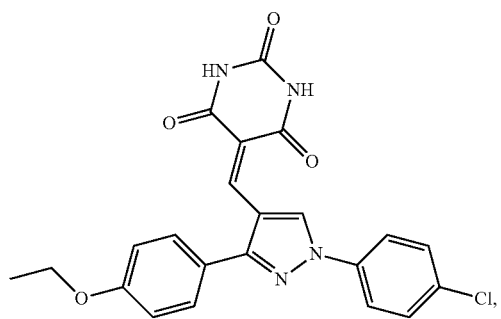
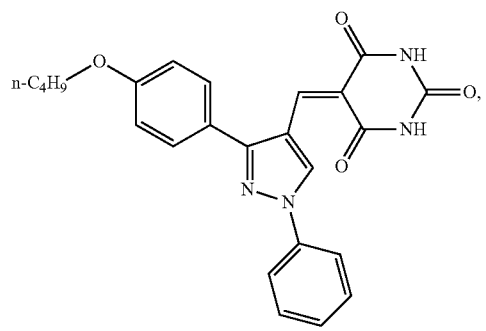
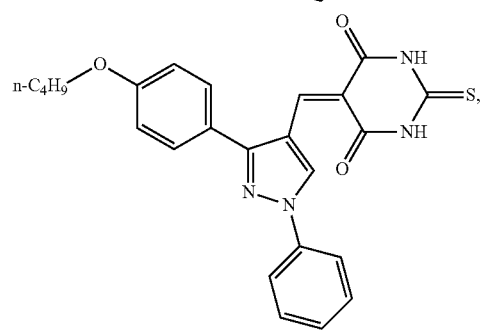
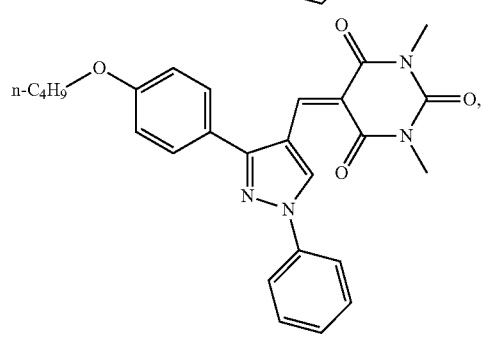
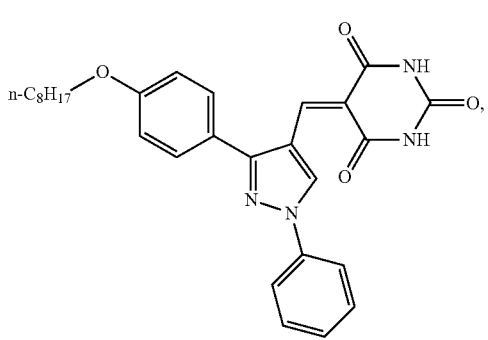
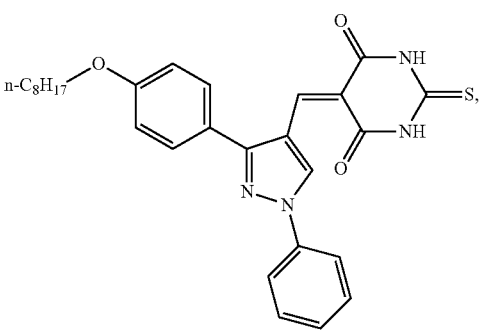
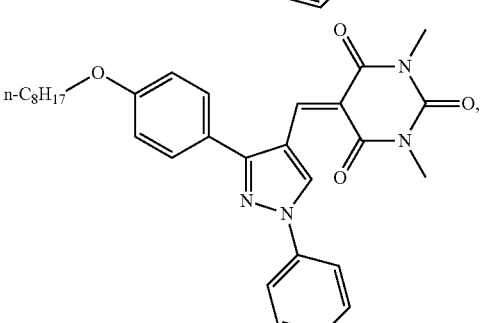
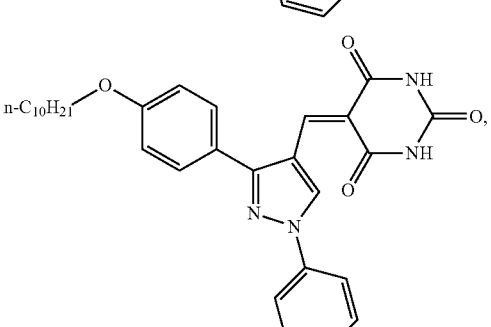
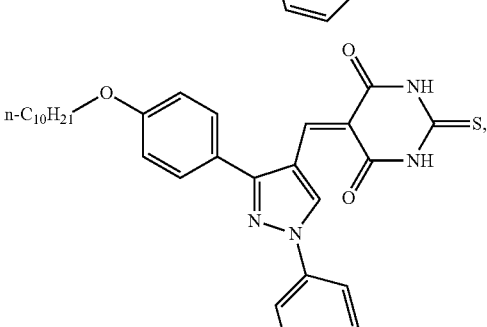
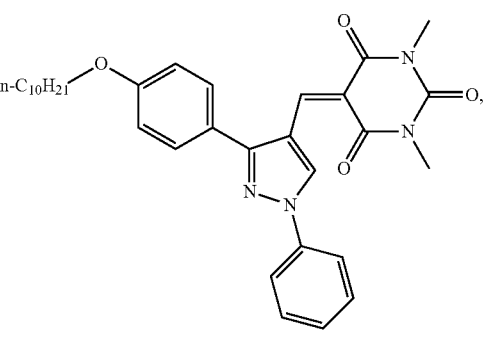

27
-continued
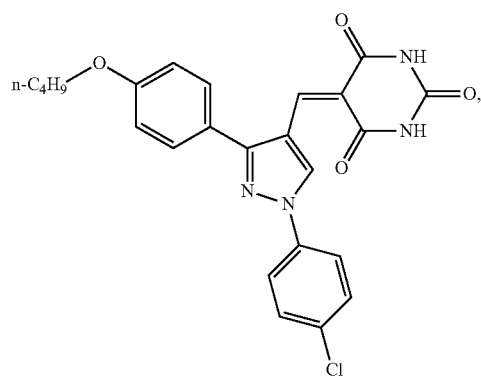
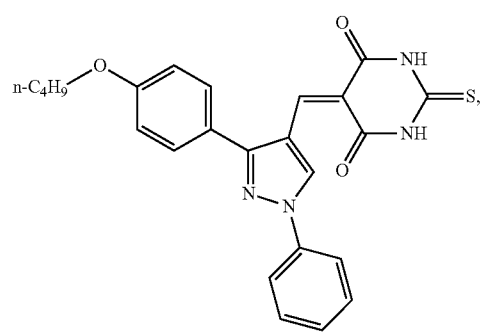
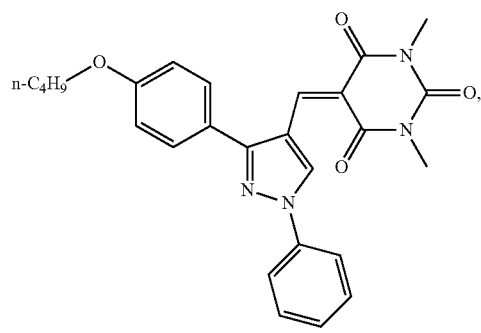
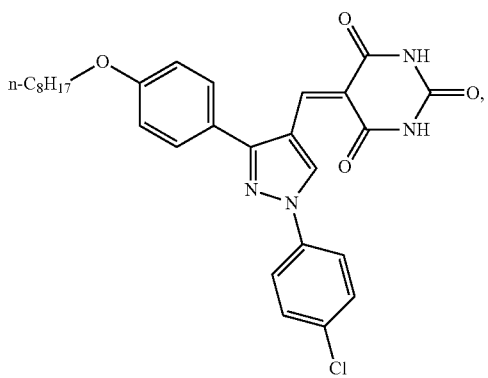
28
-continued
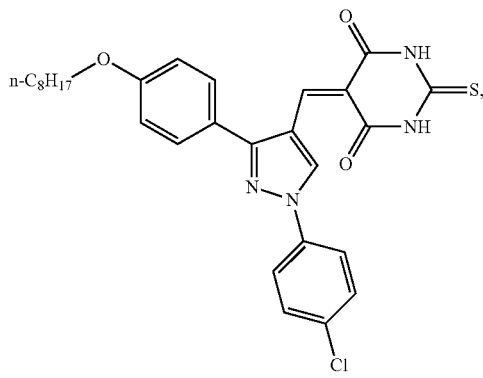
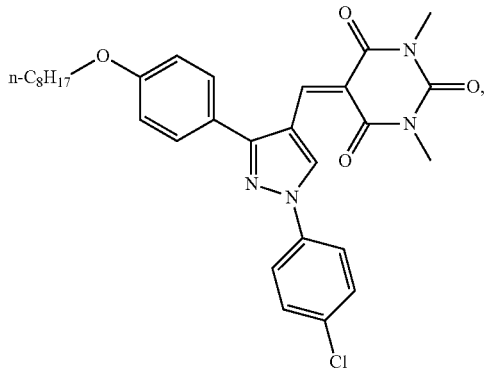
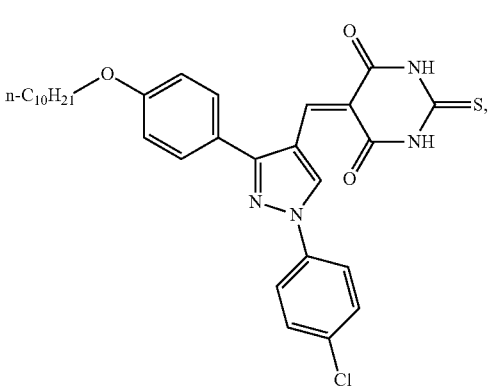

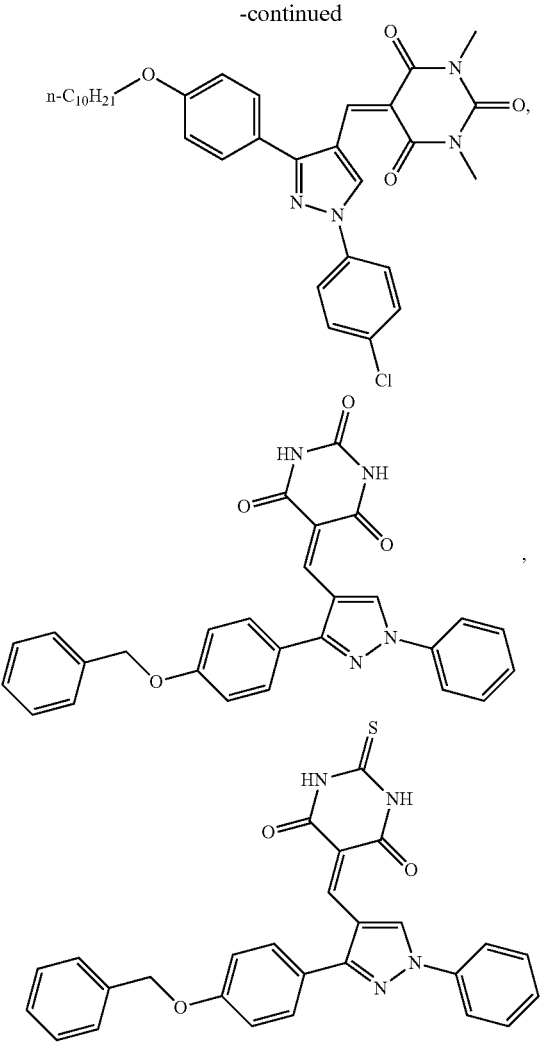

In some embodiments, the presently-disclosed subject matter includes a compound of the formula:

or pharmaceutically acceptable salts thereof, wherein R is selected from the group consisting of an aliphatic side chain and an alkyl; wherein X is selected from the group consisting of H and Cl; wherein Y is CN; wherein Z is selected from the group consisting of CN, COOH, and, together with Y, a heterocyclic group of the formula:

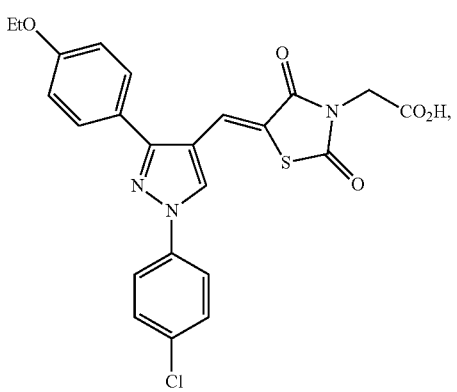

wherein $R^1$ is selected from the group consisting of O and S; and wherein $R^2$ is selected from the group consisting of H and $CH_2COOH$. In one embodiment, the compound is of the formula:

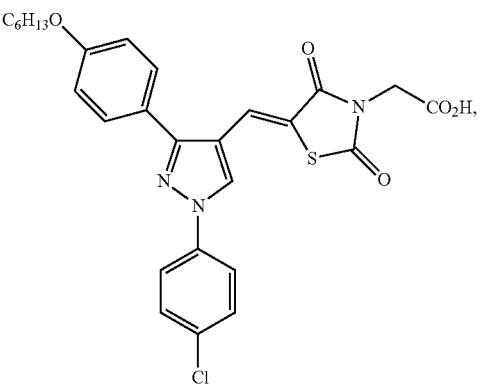

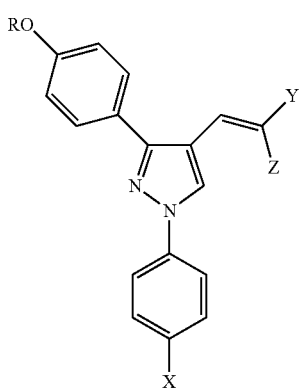

, and

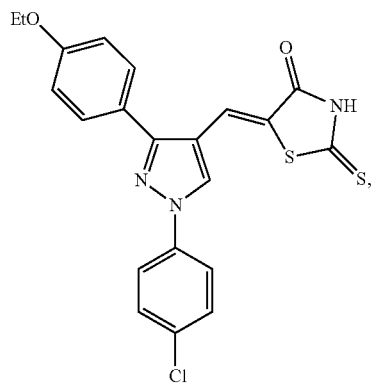

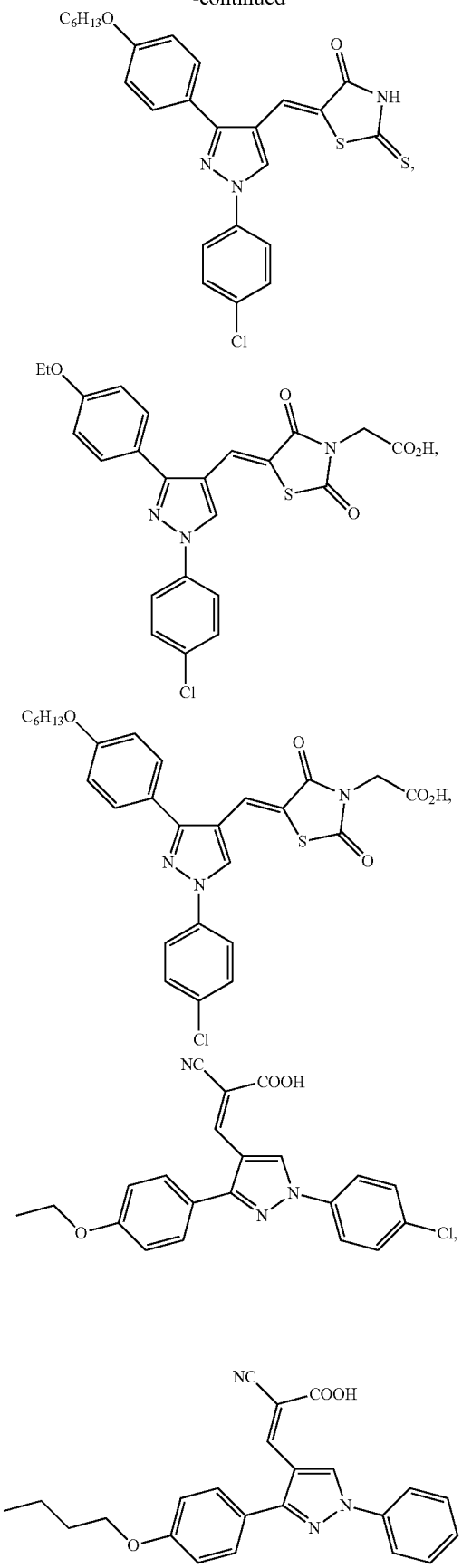
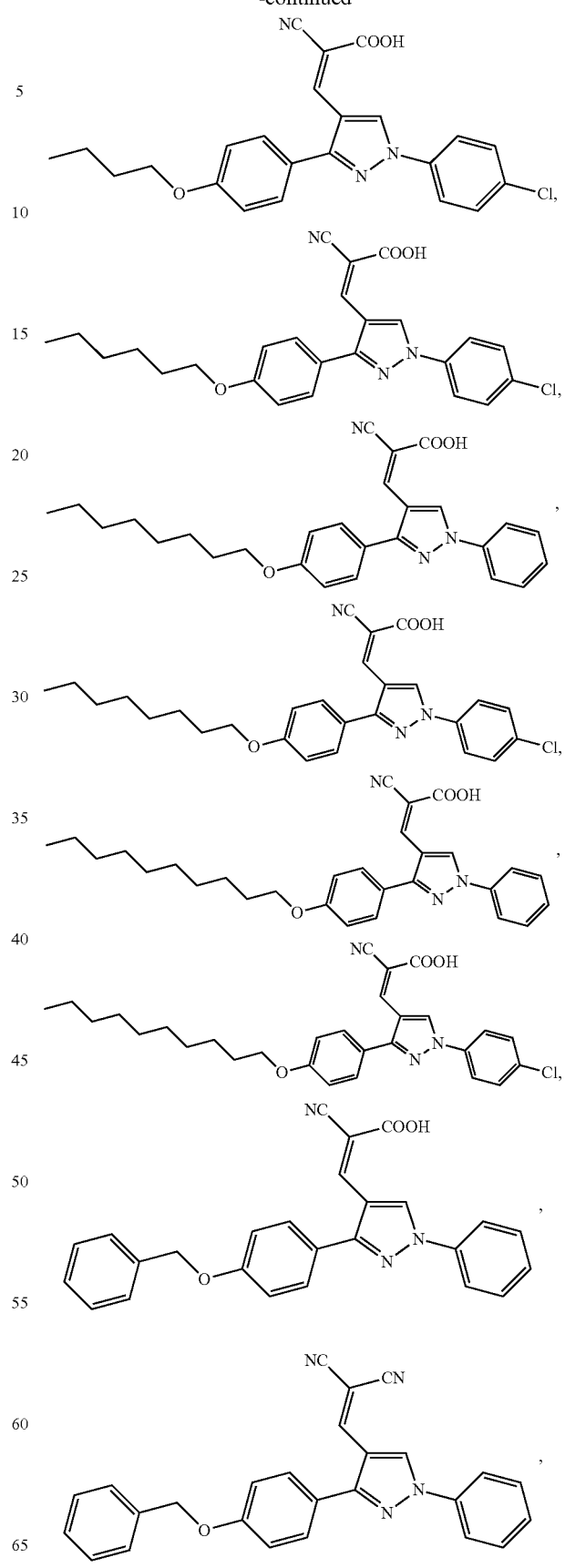

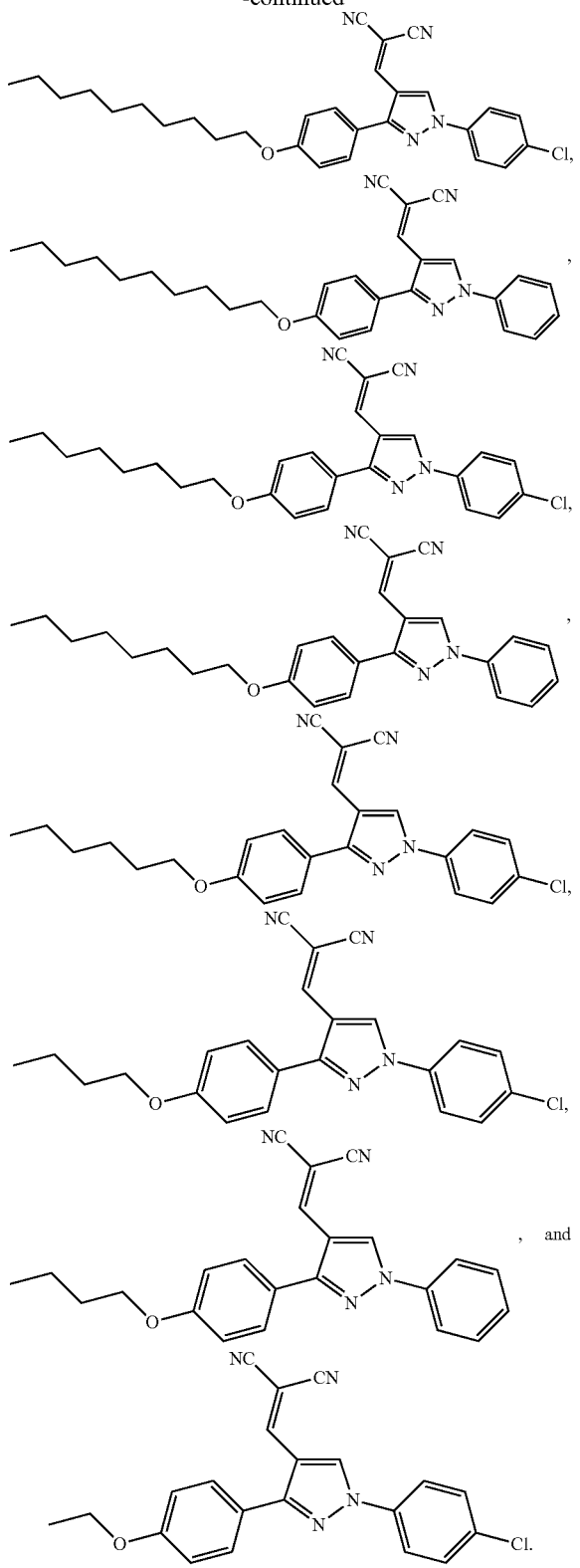

, and

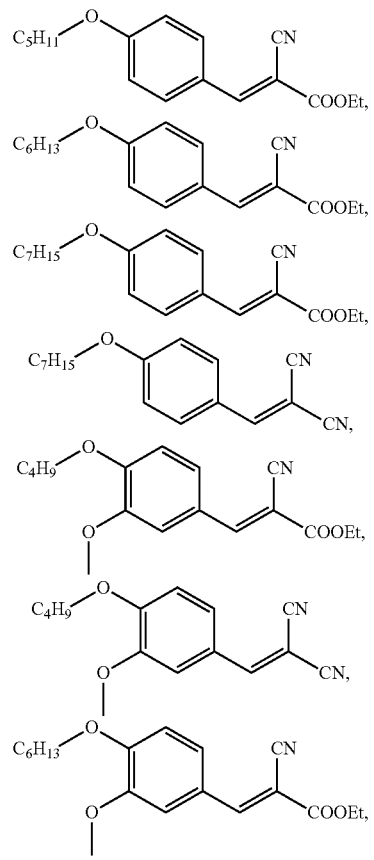

In some embodiments, the presently-disclosed subject matter includes a pharmaceutical composition comprising one of the compounds disclosed herein and a pharmaceutically-acceptable carrier. In one embodiment, the pharmaceutical composition further comprises a second compound or composition having mPGES-1 inhibition activity, having anti-inflammatory activity, being useful for treatment of an inflammation disorder, being useful for treatment of symptoms associated inflammation and/or an inflammation disorder, or combinations thereof.

In some embodiments, the presently-disclosed subject matter includes a kit comprising one of the compounds disclosed herein and a device useful for administration of the compound. In one embodiment, the kit further comprises a second compound or composition, or a treatment device having mPGES-1 inhibition activity, anti-inflammatory activity, being useful for treatment of an inflammation disorder, and/or being useful for treatment of symptoms associated inflammation and/or an inflammation disorder.

In some embodiments, the presently-disclosed subject matter includes a method of reducing inflammation in a subject, comprising administering to the subject an effective amount of one of the compound disclosed herein. In one embodiment, the subject includes an inflammation disorder or symptoms thereof. In another embodiment, the inflammation disorder is selected from the group consisting of inflammation, arthritis, fever, pain, cancer, stroke, bone disorders, and combinations thereof. In a further embodiment, the compound inhibits microsomal prostaglandin E synthase-1 (mPGES-1).

In some embodiments, the presently-disclosed subject matter includes a method of reducing inflammation in a subject, comprising administering to the subject an effective amount of a compound selected from the group consisting of.

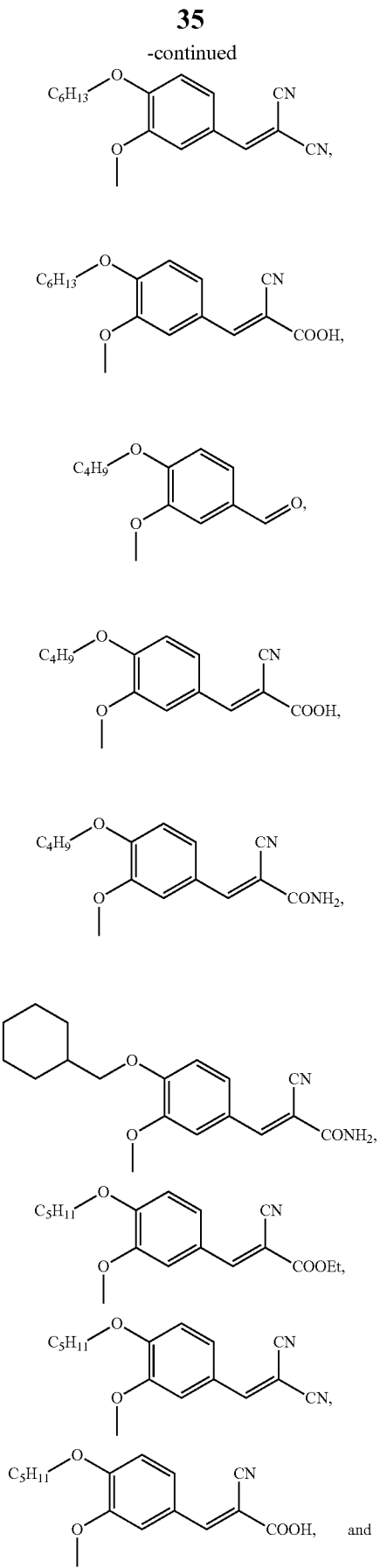

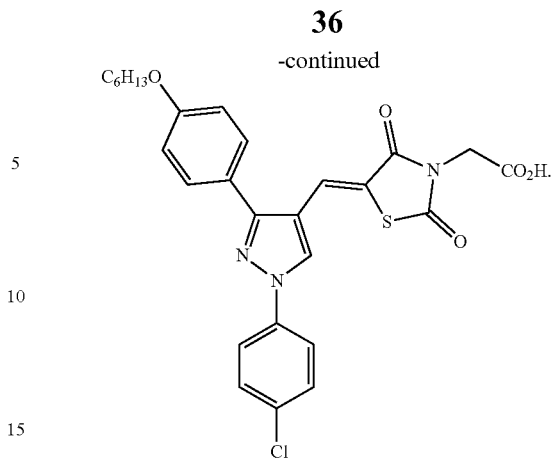

In one embodiment, the subject includes an inflammation disorder or symptoms thereof. In another embodiment, the inflammation disorder is selected from the group consisting of inflammation, arthritis, fever, pain, cancer, stroke, bone disorders, and combinations thereof. In a further embodiment, the compound inhibits microsomal prostaglandin E synthase-1 (mPGES-1).

Further features and advantages of the presently-disclosed subject matter will become evident to those of ordinary skill in the art after a study of the description, figures, and non-limiting examples in this document.

DESCRIPTION OF EXEMPLARY EMBODIMENTS

Figure 1:
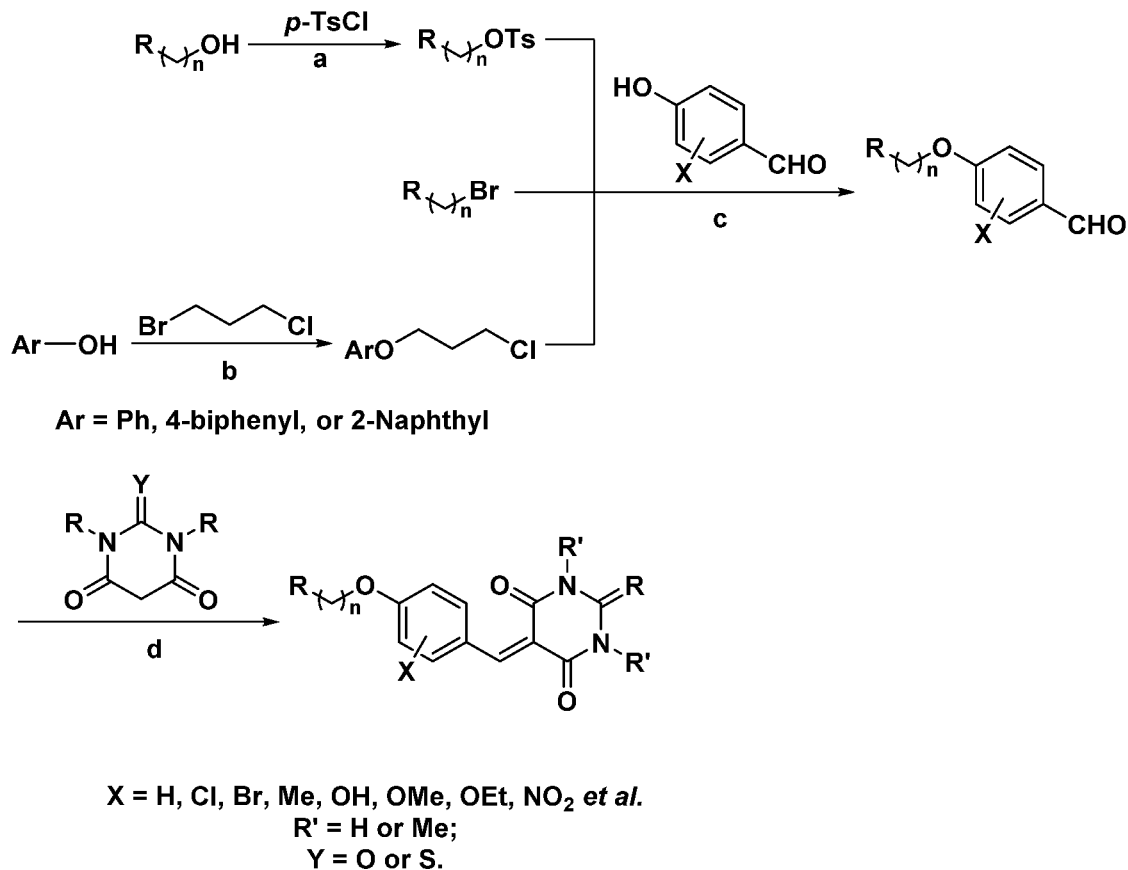
FIG. 1 shows a schematic view of the general synthesis of compounds having the structure of formula I, according to an embodiment of the disclosure. Reagents and conditions: (a) 50% KOH aq., DCM, 0° C.~rt; (b) $K_2CO_3$ (2.0 equiv.), Acetone, reflux; (c) $K_2CO_3$ (2.0 equiv.), DMF, 80° C.; (d) EtOH/$H_2O$ (4:1, v/v), reflux.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

The presently-disclosed subject matter meets some or all of the above-identified needs, as will become evident to those of ordinary skill in the art after a study of information provided in this document. To avoid excessive repetition, this Description does not list or suggest all possible combinations of such features.

The presently-disclosed subject matter includes a compound having a structure represented by the formula I:

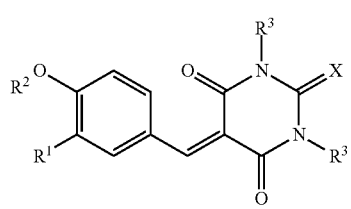

(I)

or pharmaceutically acceptable salts thereof, wherein R$^1$ includes H, halide, Me, OMe, OEt, NO$_2$, OH, or taken together with the ring to which it is attached, a bicyclic ring system as in the formula:

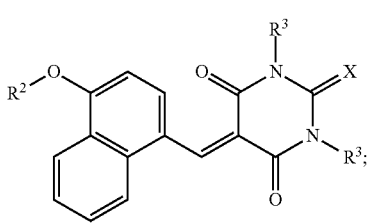

R$^2$ includes an alkyl; R$^3$ includes H or Me; and X includes O or S.

In some embodiments of the compound having the structure of formula I, R$^1$ includes H, Cl, Br, I, Me, OMe, OEt, NO$_2$, OH, or taken together with the ring to which it is attached, a bicyclic ring system.

In some embodiments of the compound having the structure of formula I, R$^2$ includes:

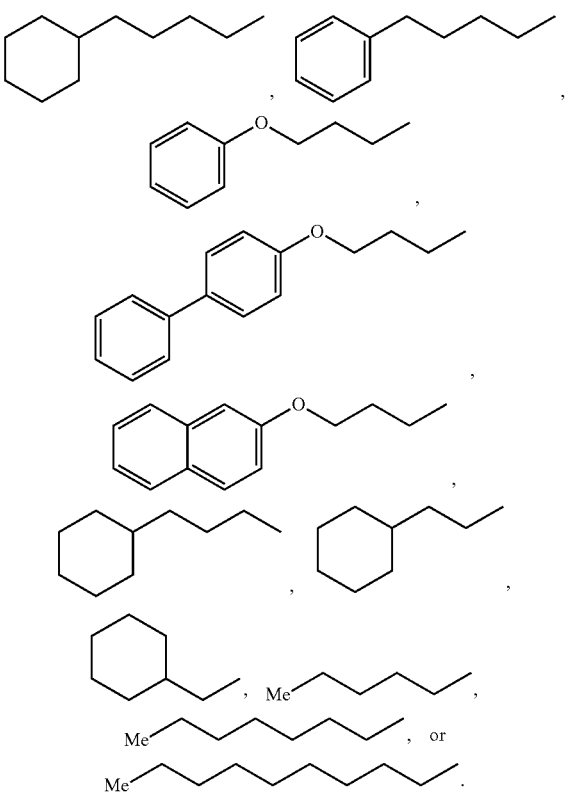

In some embodiments of the compound of formula I, the compound has the structure selected from the group consisting of:

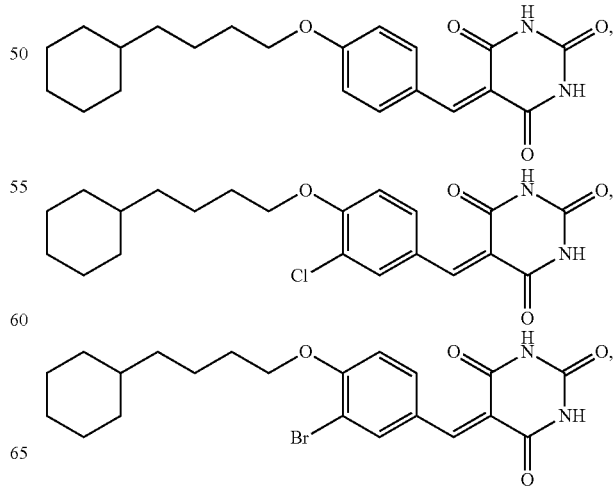

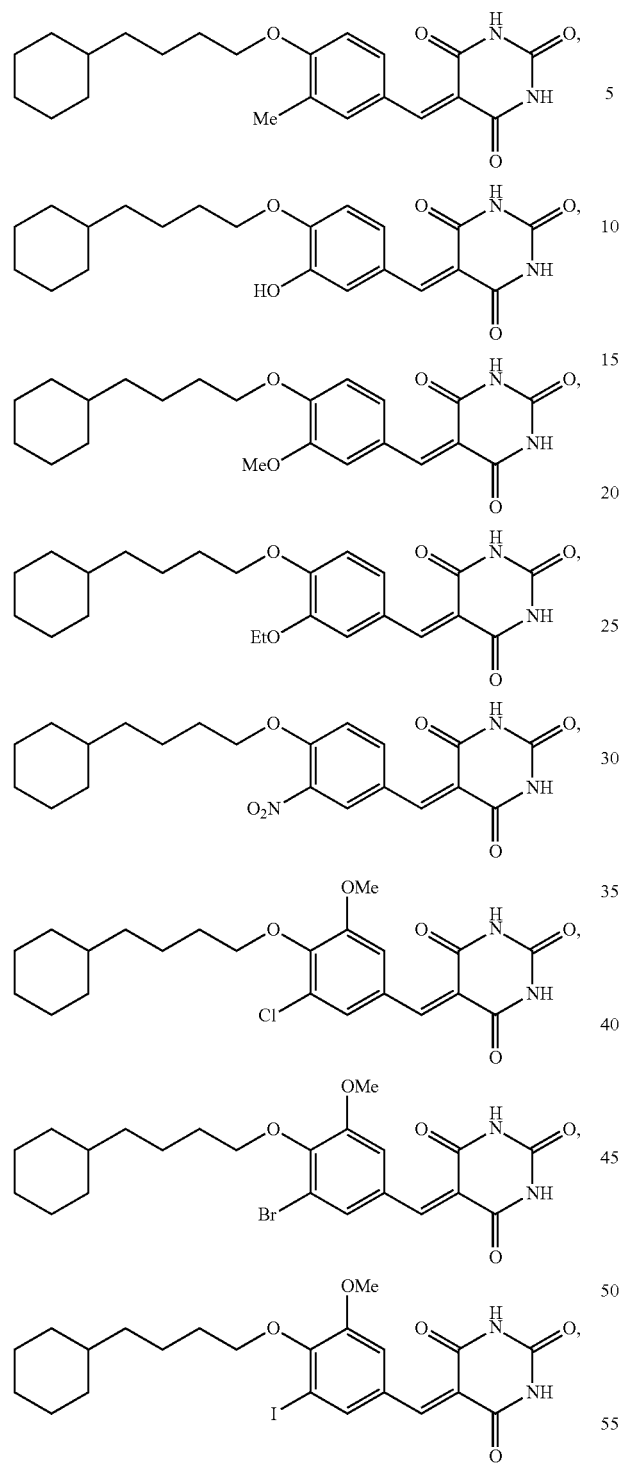
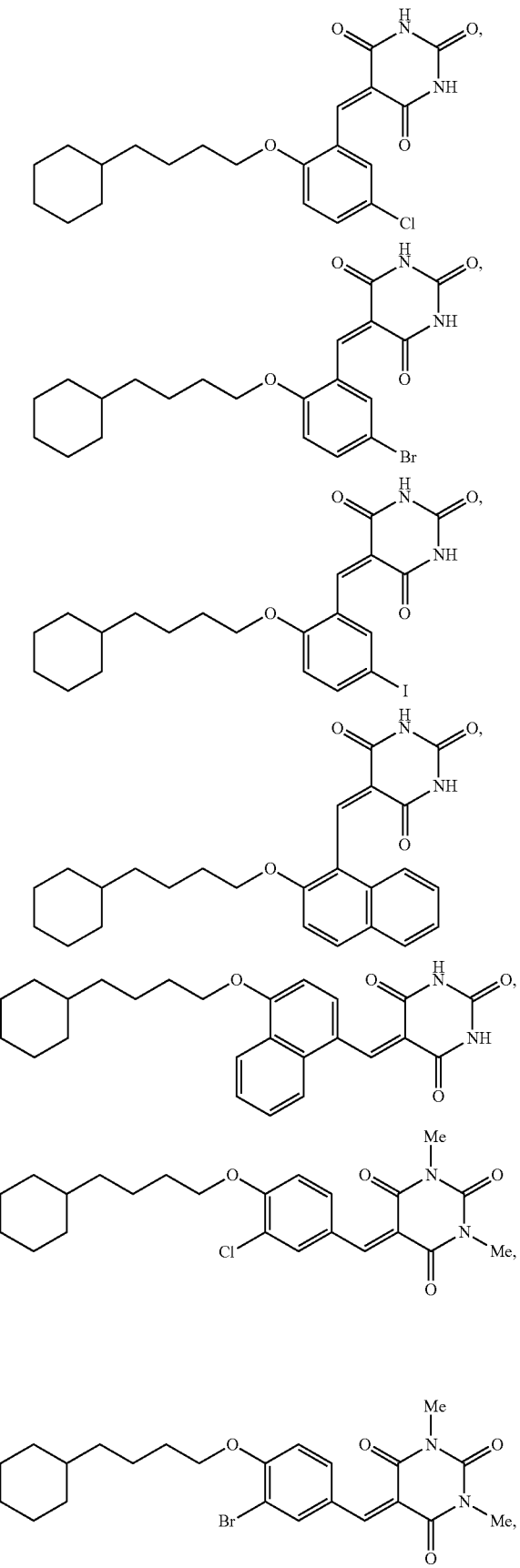

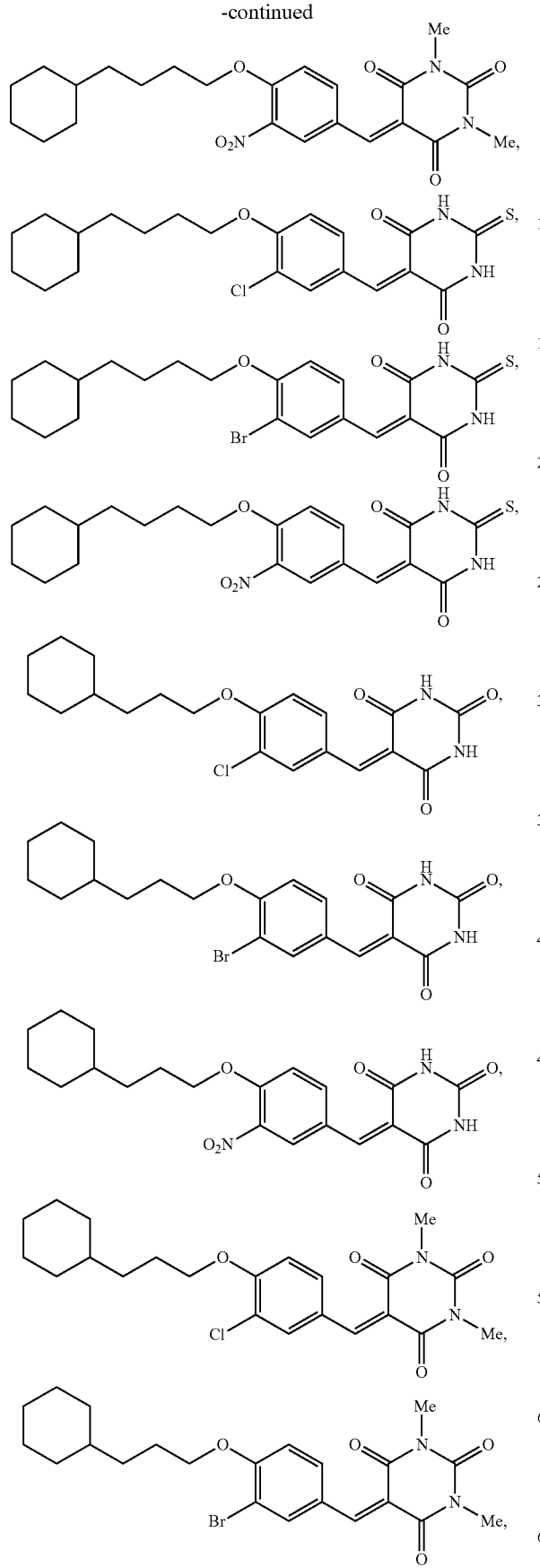
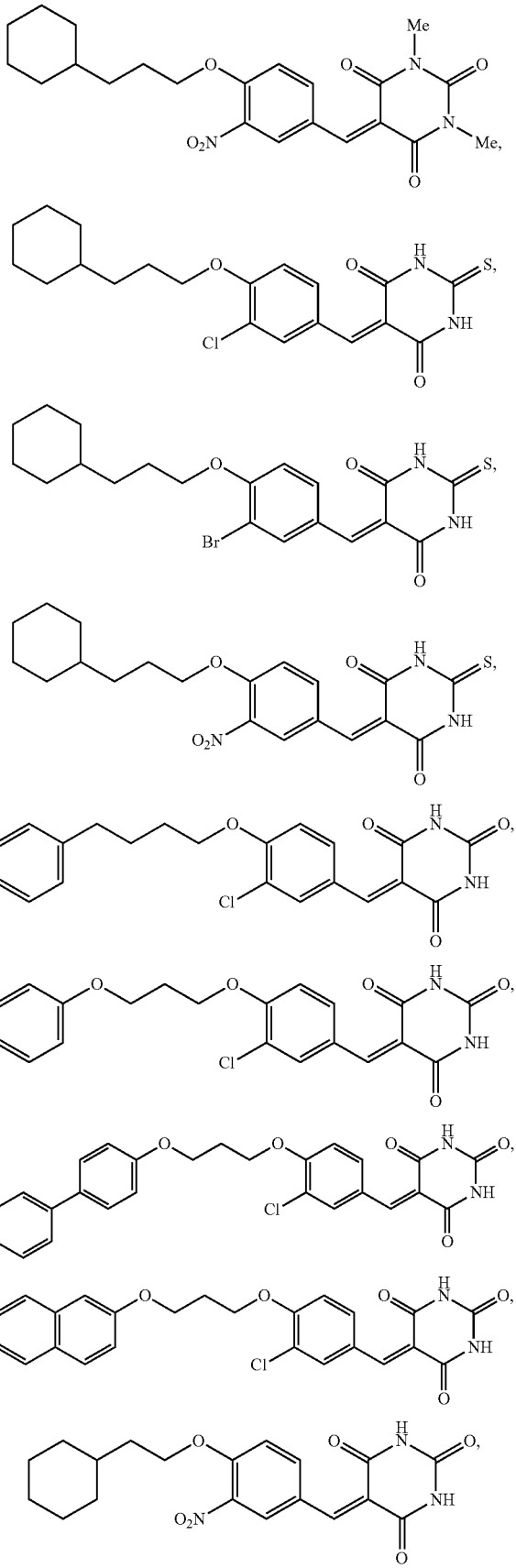

-continued

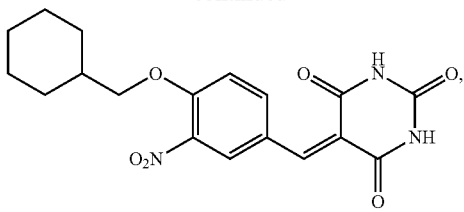

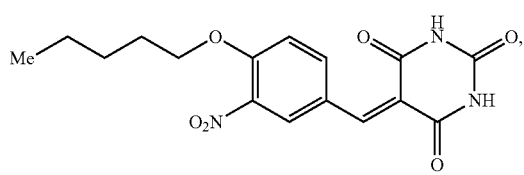

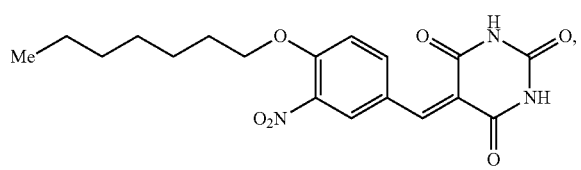

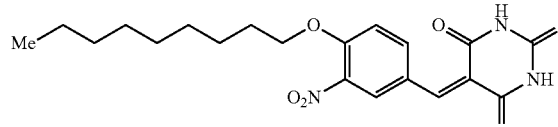

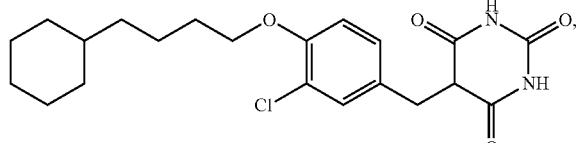

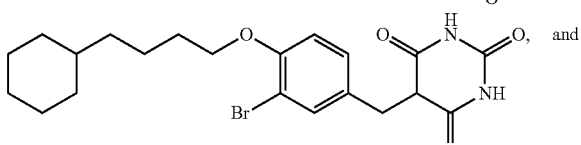

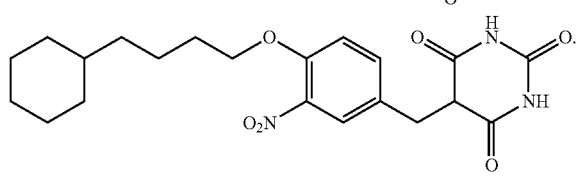

In some embodiments of the compound of formula I, the compound has the structure of

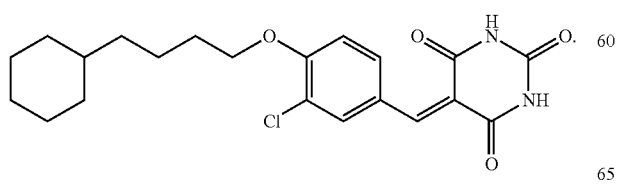

The presently-disclosed subject matter includes a compound having a structure represented by the formula:

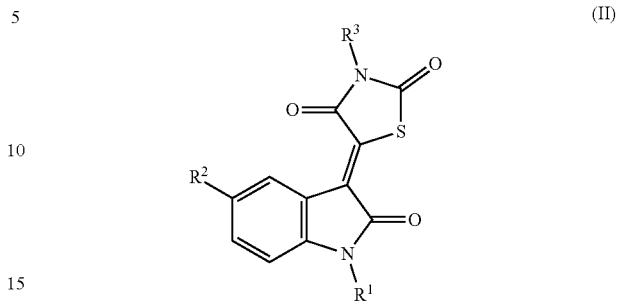

(II)

or pharmaceutically acceptable salts thereof, wherein $R^1$ includes H, an alkyl, an alkyl halide, an ether, or a carboxylic acid; $R^2$ includes H, a halide, an alkyne, or an aromatic; and $R^3$ includes H, a carboxyl (e.g., $CO_2H$), a carboxylic acid (e.g., $CH_2CO_2H$), or an alkyl.

In some embodiments of the compound having the structure of formula II, R is selected from the group consisting of: H,

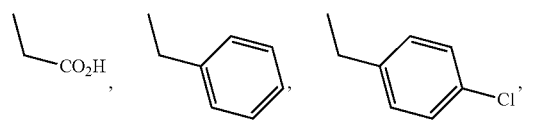

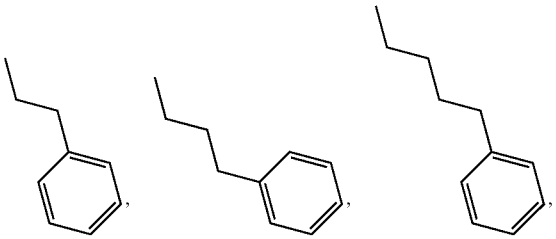

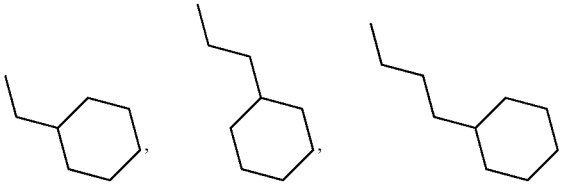

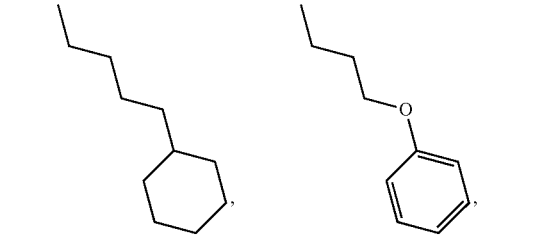

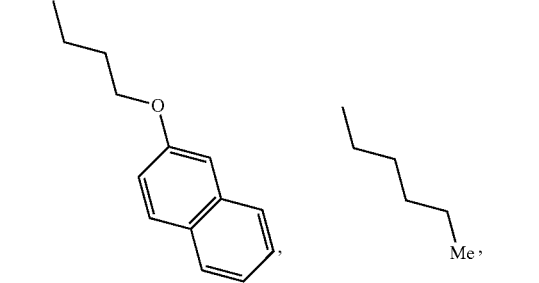

-continued

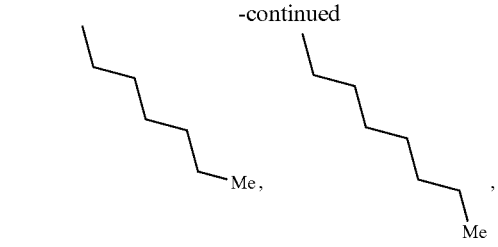

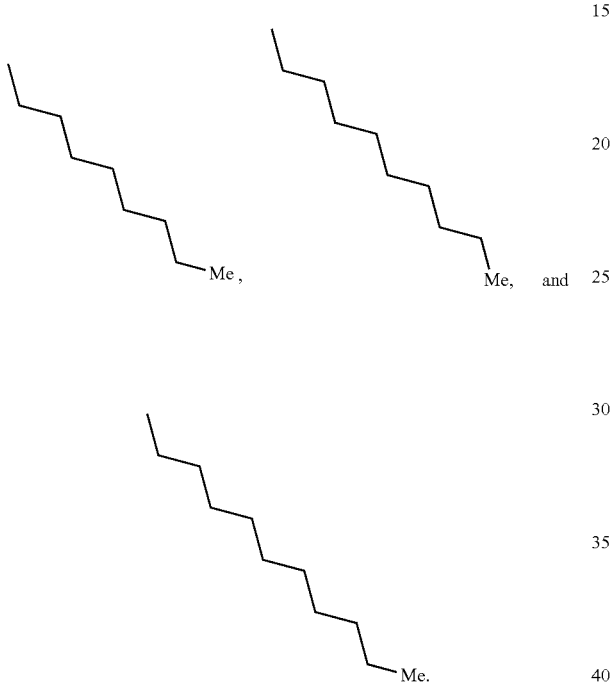

In some embodiments of the compound having the structure of formula II, R² is selected from the group consisting of:

H,

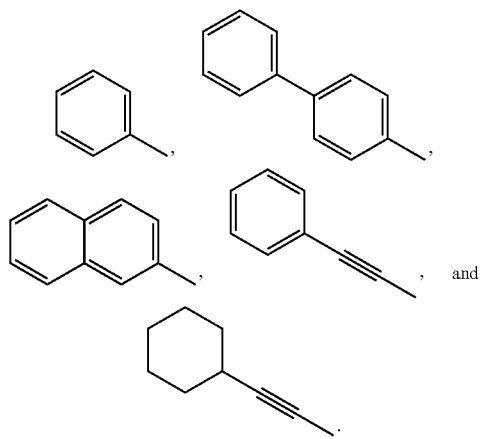

In some embodiments of the compound having the structure of formula II, R³ is selected from the group consisting of:

H,

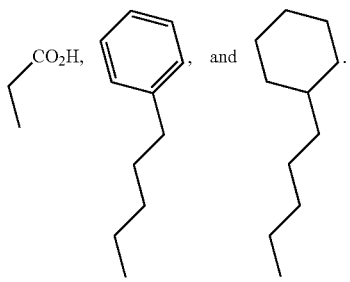

In some embodiments of the compound having the structure of formula II, the compound has the structure selected from the group consisting of:

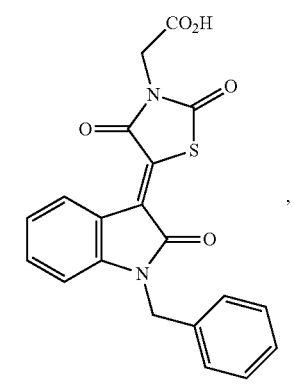

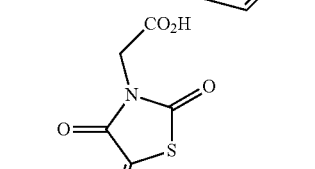

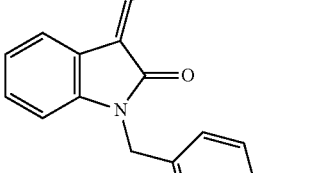

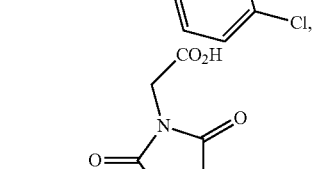

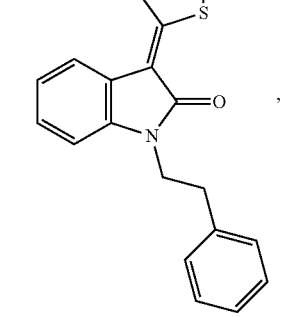

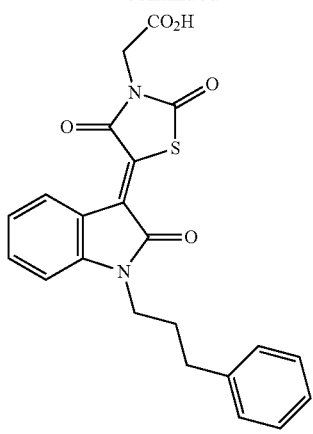
,
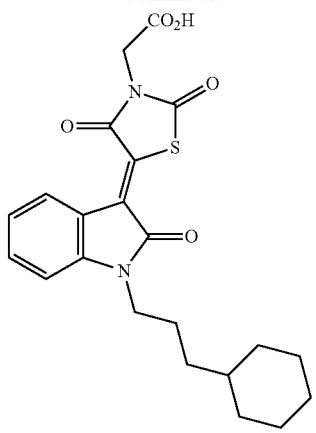
,
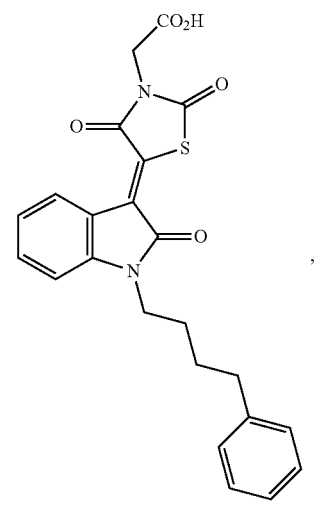
,
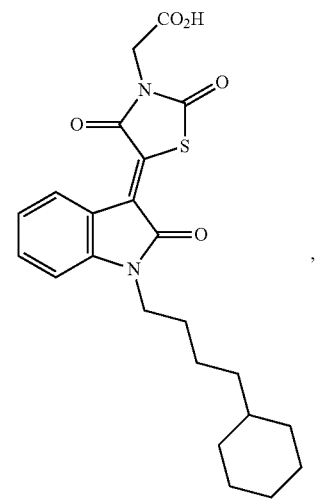
,
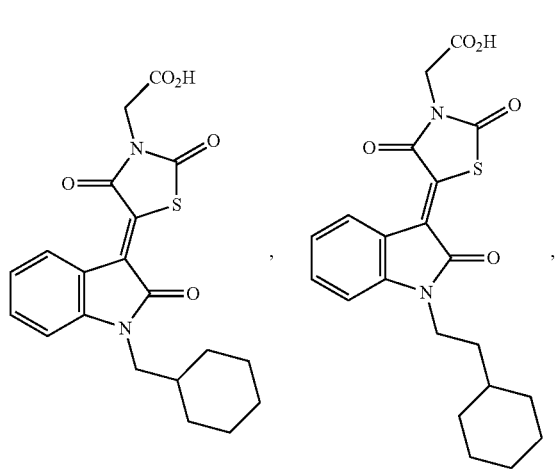
,
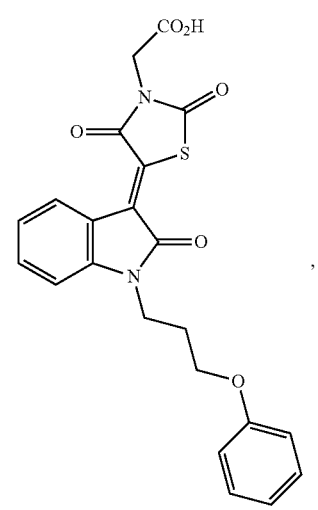
, -continued
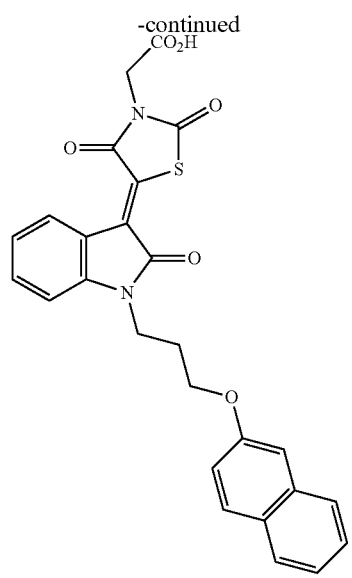
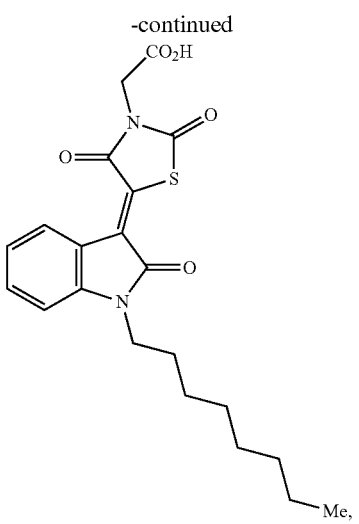
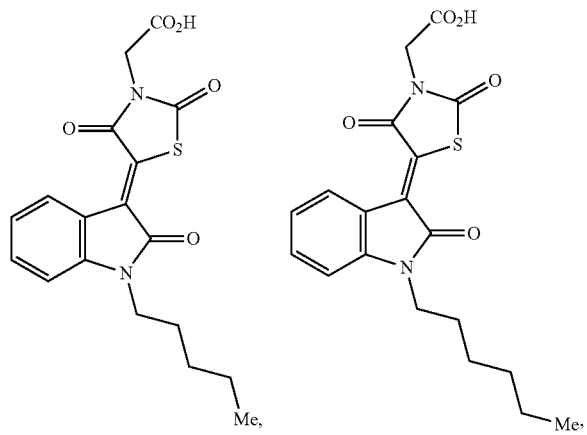
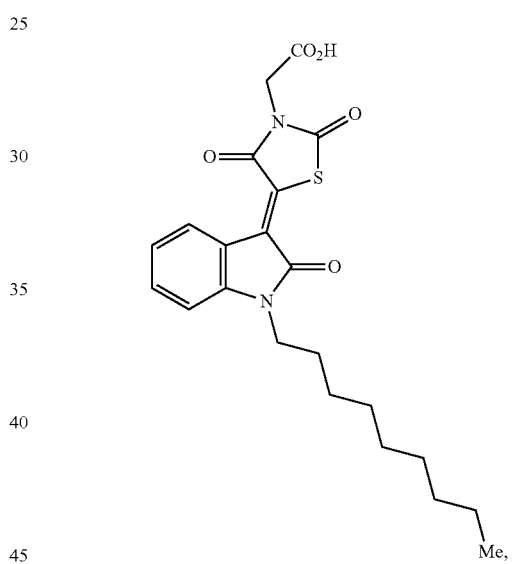
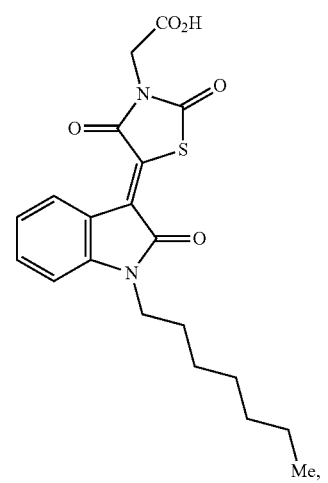
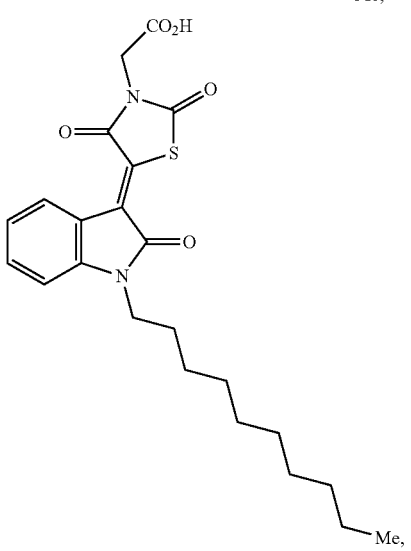

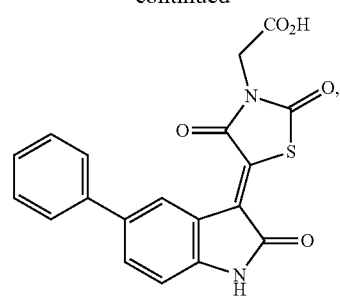
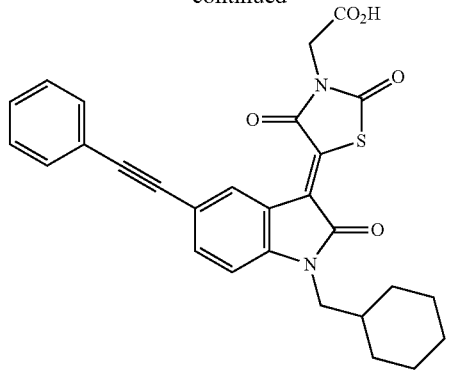

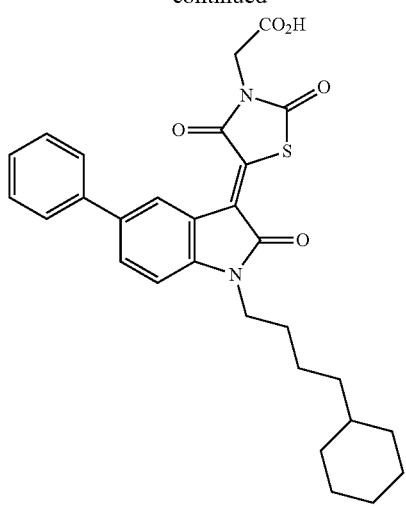
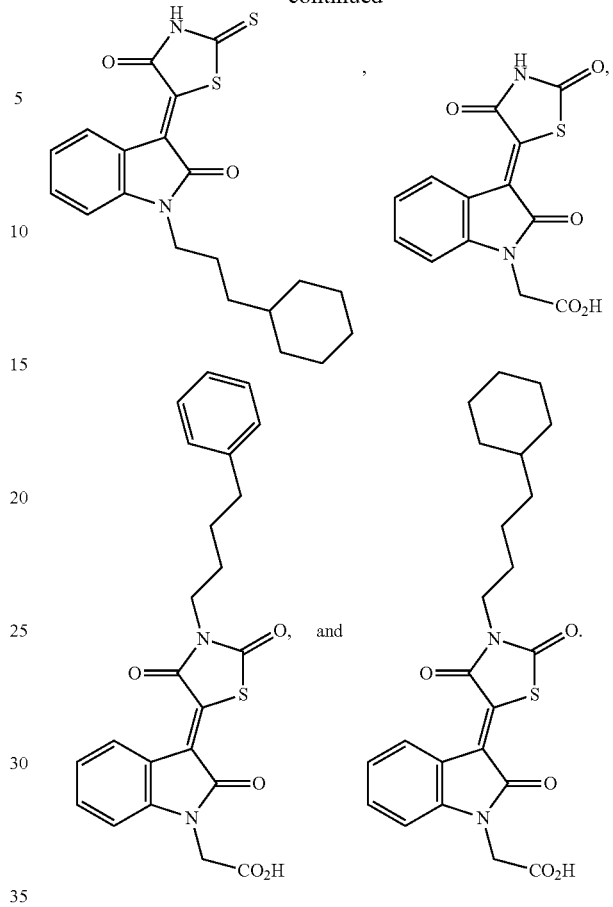
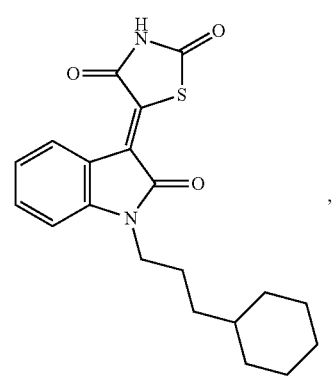
The presently-disclosed subject matter includes a compound having a structure represented by the formula:
$$\text{(III)}$$
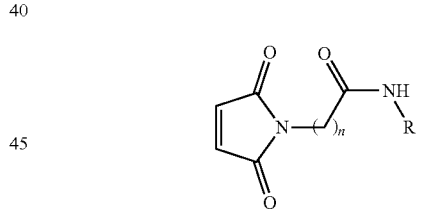
or pharmaceutically acceptable salts thereof, wherein R is an alkyl or alkoxy; and n is 1, 2, 3, 4, 5, or 6.
In some embodiments of the compound having the structure of formula III, R is selected from the group consisting of:
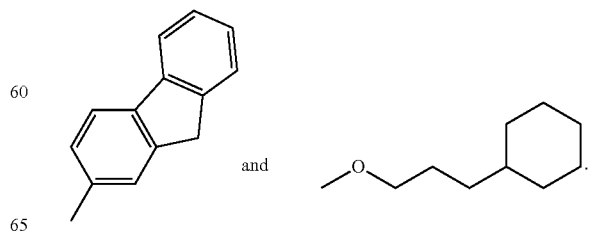

In some embodiments of the compound having the structure of formula III, the compound has the structure selected from the group consisting of:

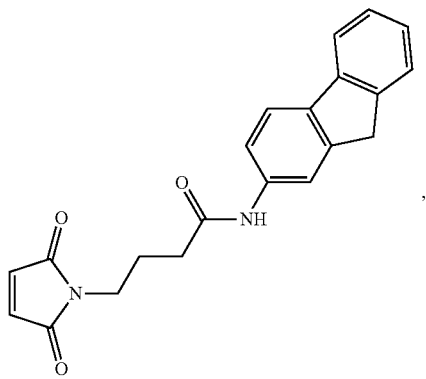

,

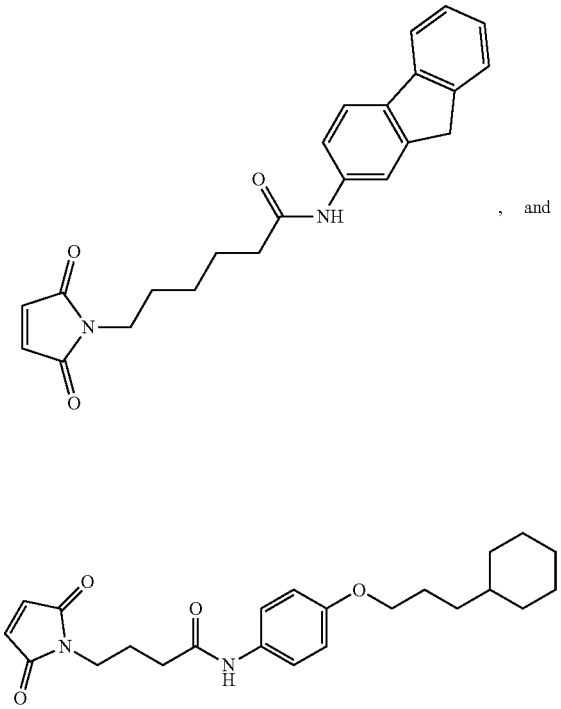

, and

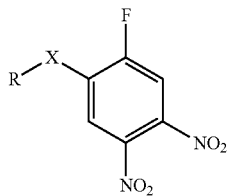

The presently-disclosed subject matter includes a compound having a structure represented by the formula:

(IV)

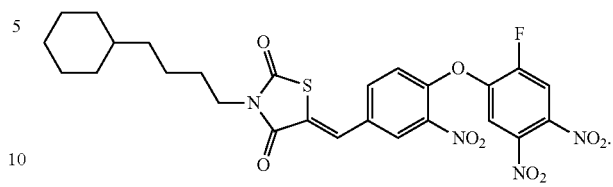

or pharmaceutically acceptable salts thereof, wherein R is selected from the group consisting of substituted phenyl; and X is O.

In some embodiments, the compound of formula IV has the structure of

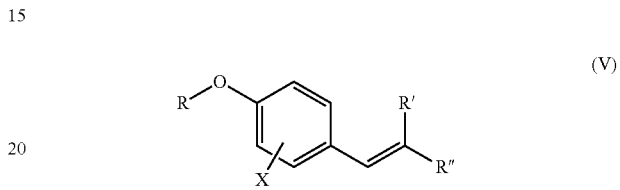

The presently-disclosed subject matter includes a compound having a structure represented by the formula:

(V)

$$R\text{—}O\text{—}\underset{X}{\text{Ar}}\text{—}CH\text{=}C(R')(R'')$$

or pharmaceutically acceptable salts thereof.

In some embodiments of the compound having the structure of formula V, R includes an aliphatic side chain or an alkyl; X is selected from the group consisting of H, $NO_2$, Br, or OMe; and R' and R'' are independently selected from the group consisting of CN, COOH, COOEt, $CONH_2$, and $NO_2$.

In some embodiments of the compound having the structure of formula V, the compound is selected from the group consisting of:

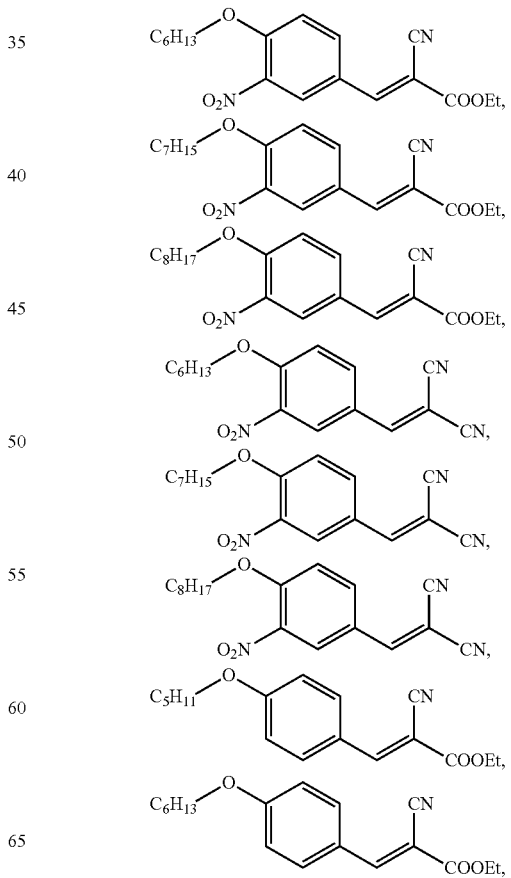

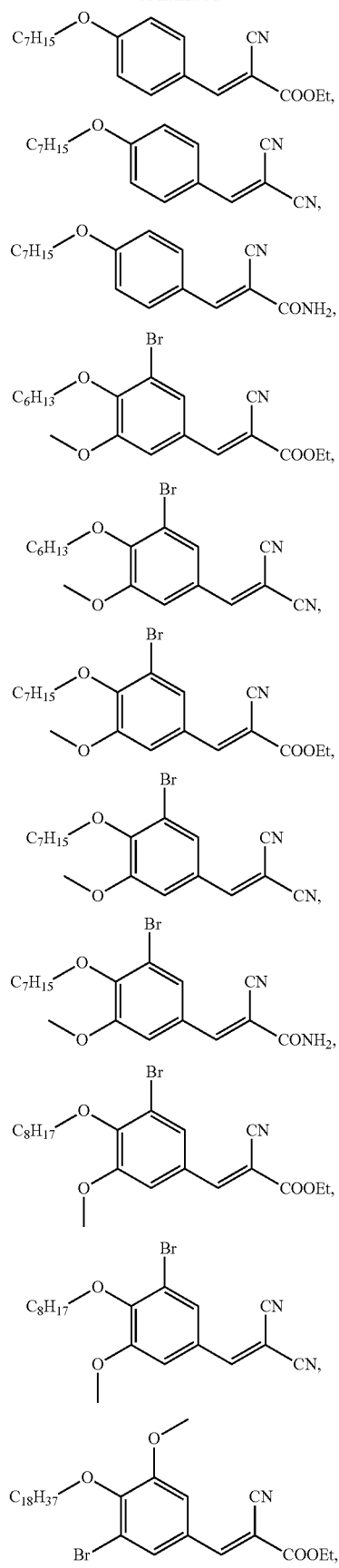
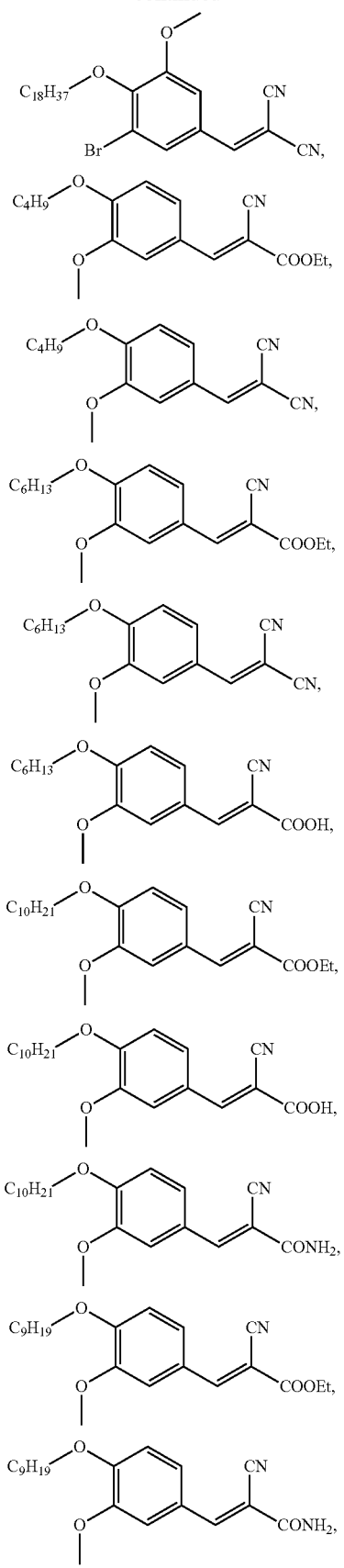

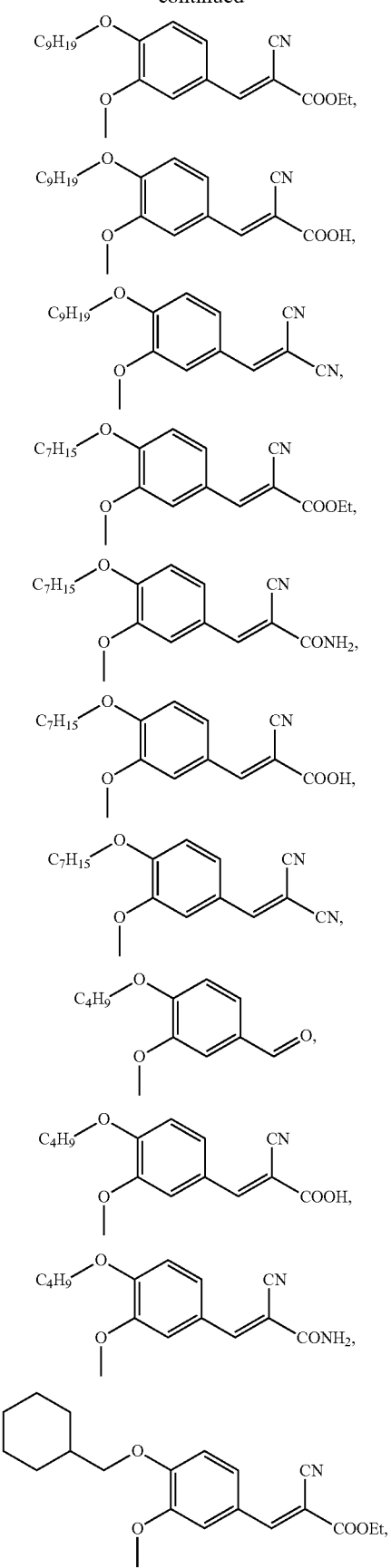
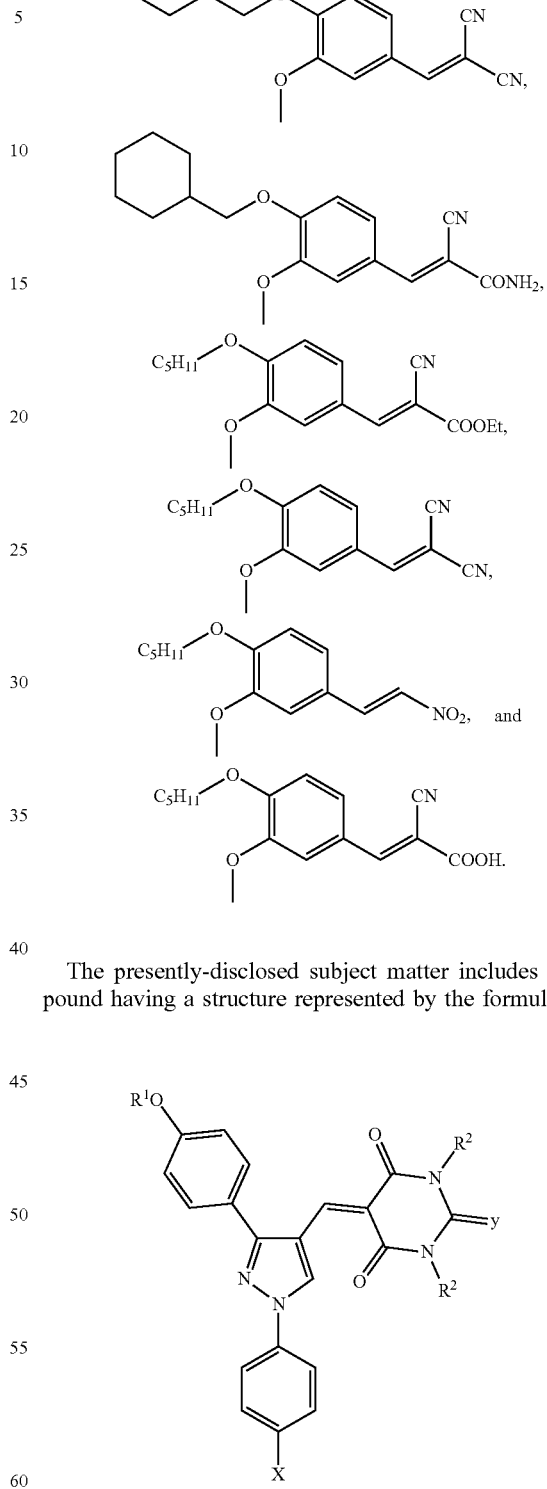
The presently-disclosed subject matter includes a compound having a structure represented by the formula:
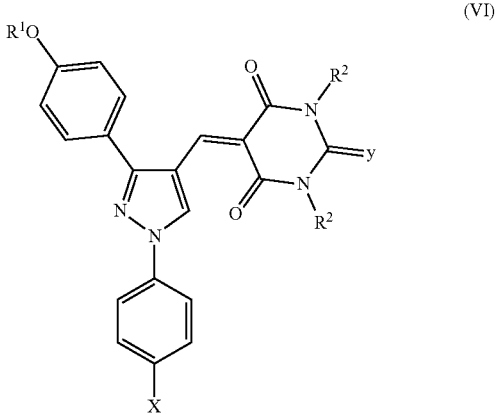
(VI)
or pharmaceutically acceptable salts thereof.
In some embodiments of the compound having the structure of formula VI, X includes H or a halogen such as Cl; $R^1$ includes an alkyl; each $R^2$ independently includes H or an alkyl; and Y includes S or O.

In some embodiments of the compound having the structure of formula VI, the compound has the structure selected from the group consisting of:
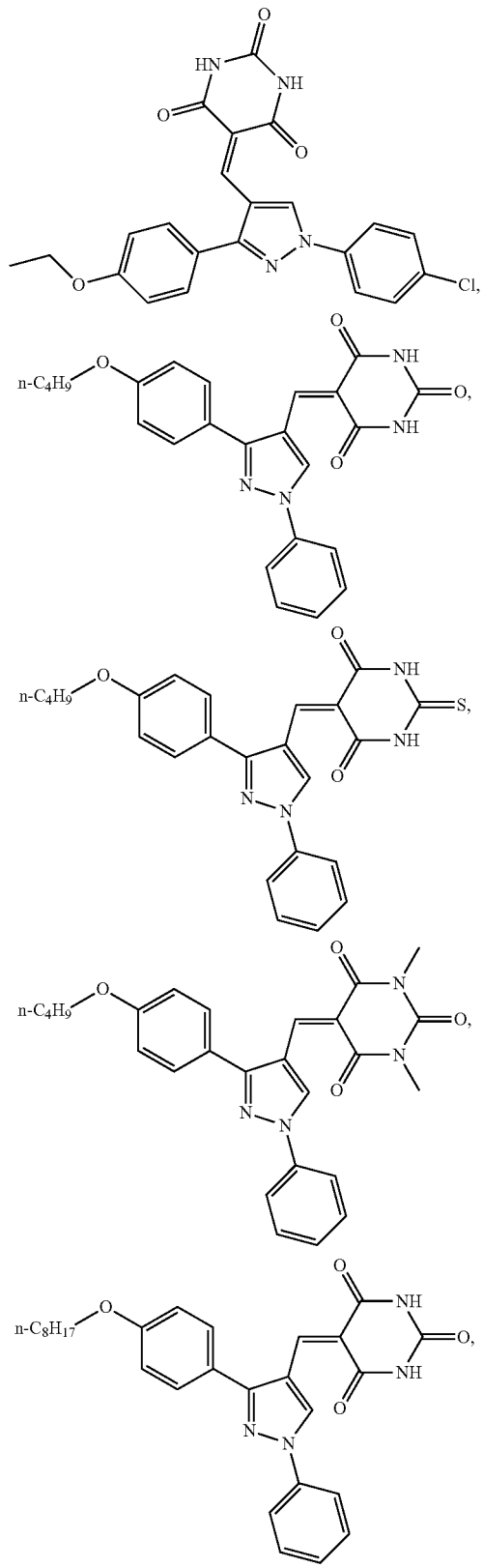
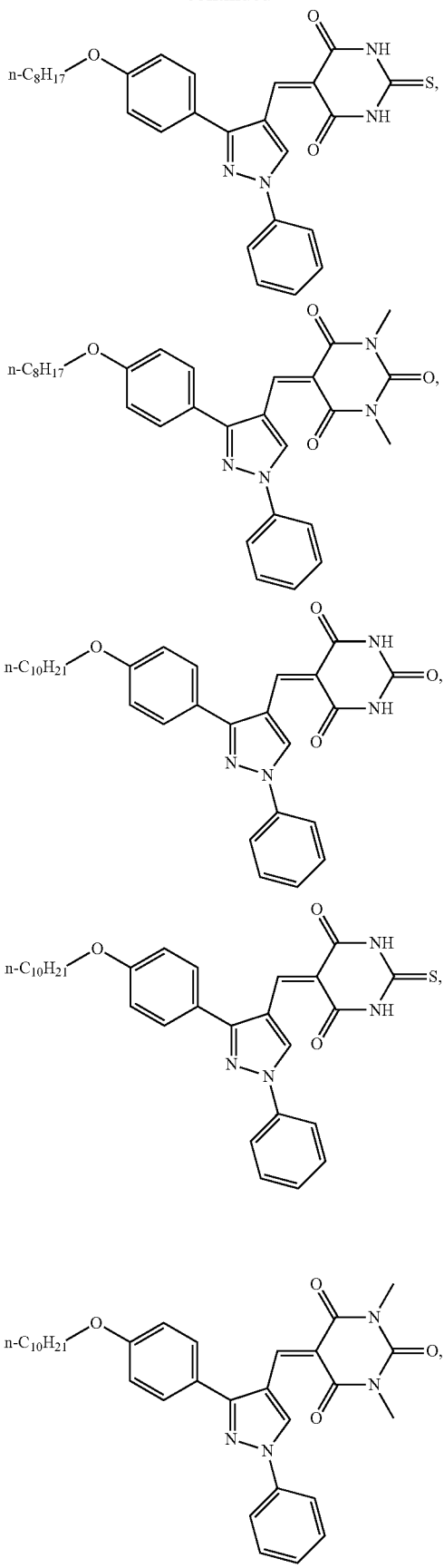

-continued
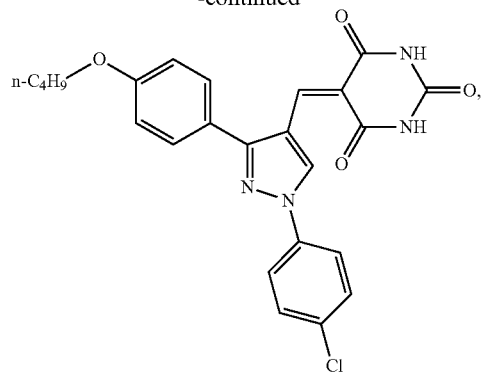
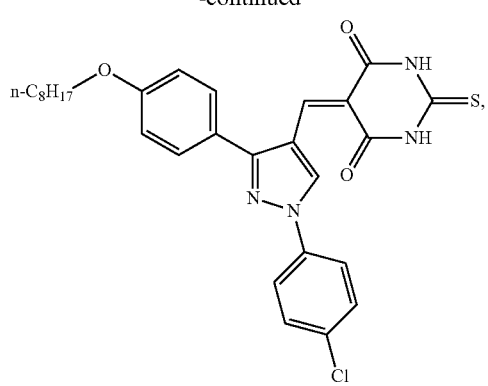
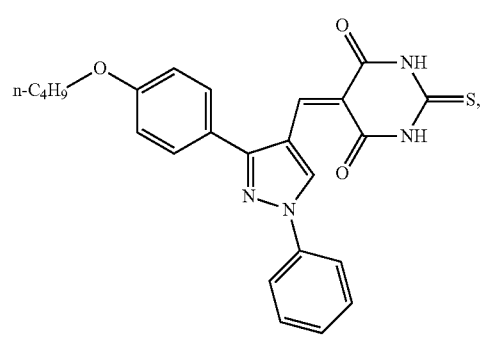
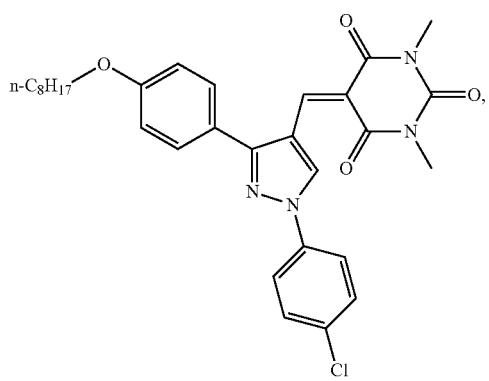
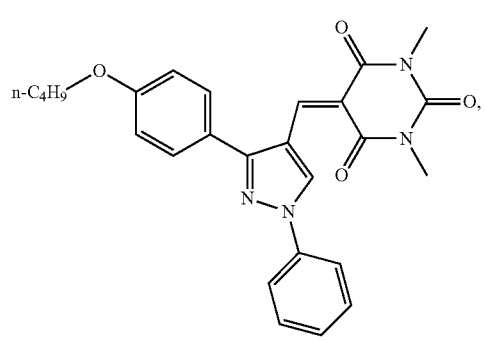
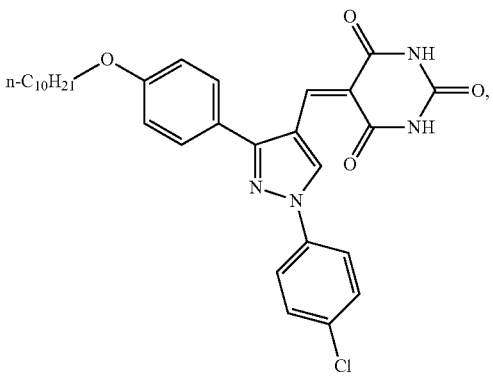
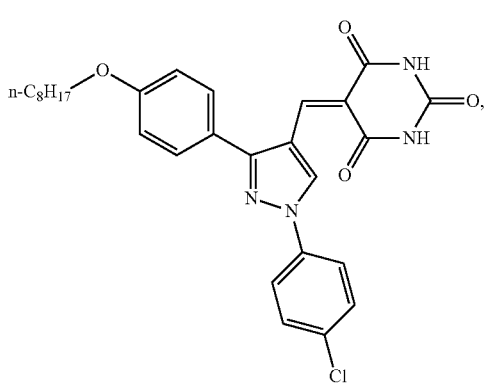
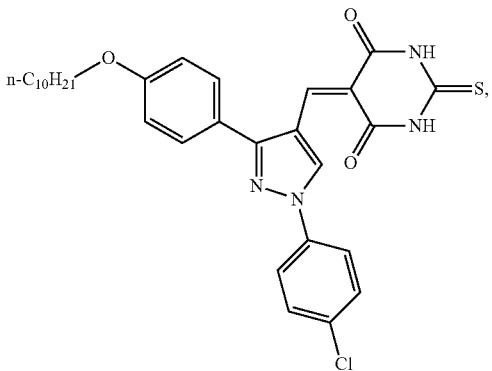

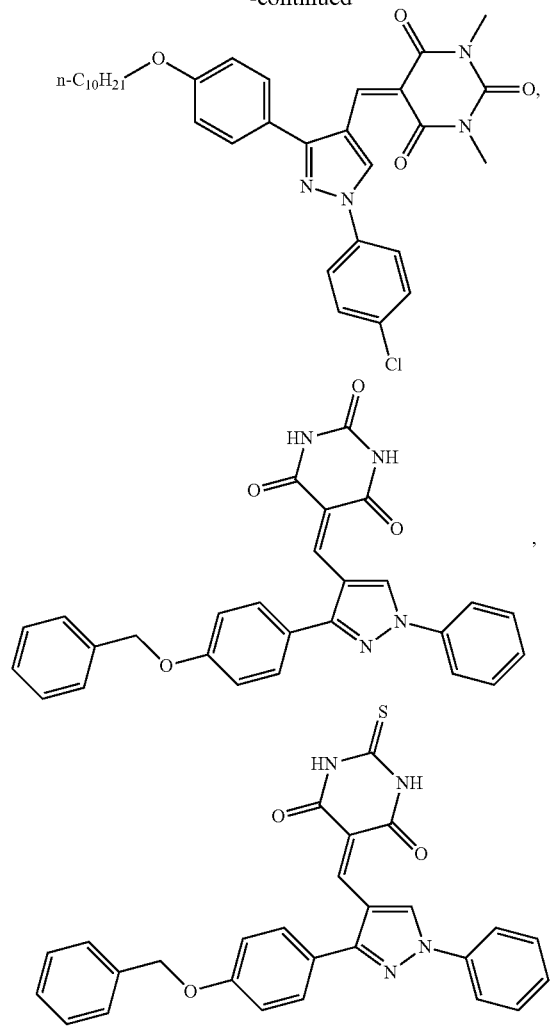

, and

The presently-disclosed subject matter further includes a compound having a structure represented by the formula:

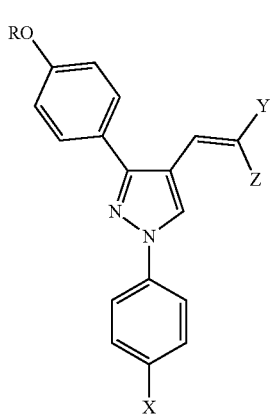

(VII)

or pharmaceutically acceptable salts thereof.

In some embodiments of the compound having the structure of formula VII, X includes H or Cl; Y includes CN; Z includes CN or COOH; and R includes an aliphatic side chain or an alkyl. In some embodiments of the compound having the structure of formula VII, Y and Z together form a heterocyclic group, such as, but not limited to, a five membered heterocyclic group. In one embodiment, for example, Y and Z together form a thiazolidine group having the structure:

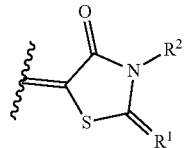

wherein $R^1$ includes O or S; and $R^2$ includes H or $CH_2COOH$.

In some embodiments of the compound having the structure of formula VII, the compound has the structure selected from the group consisting of:

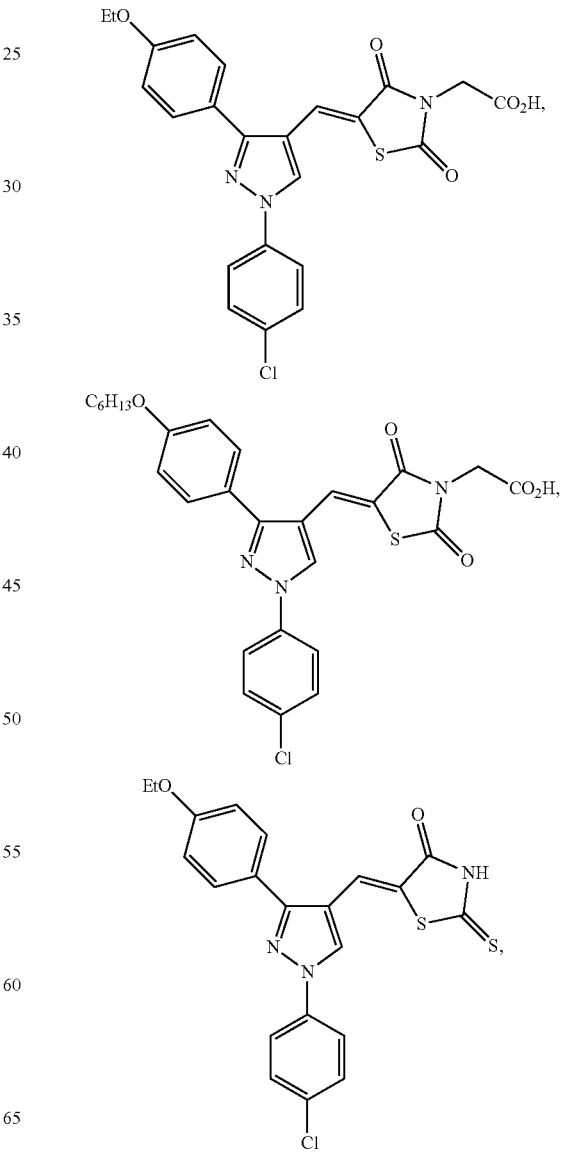

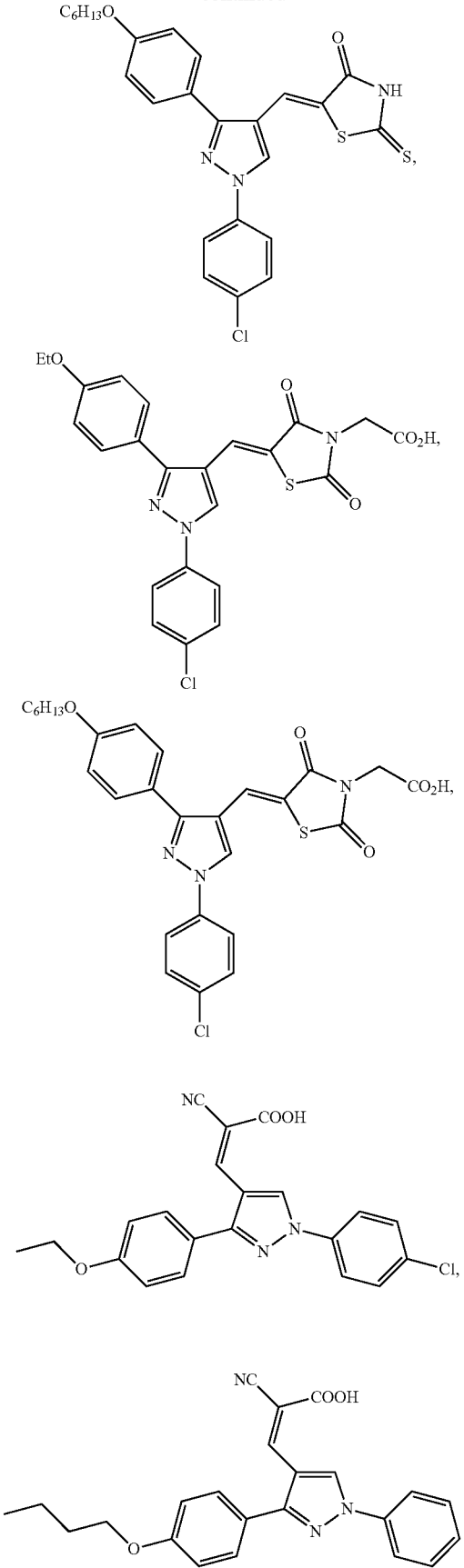

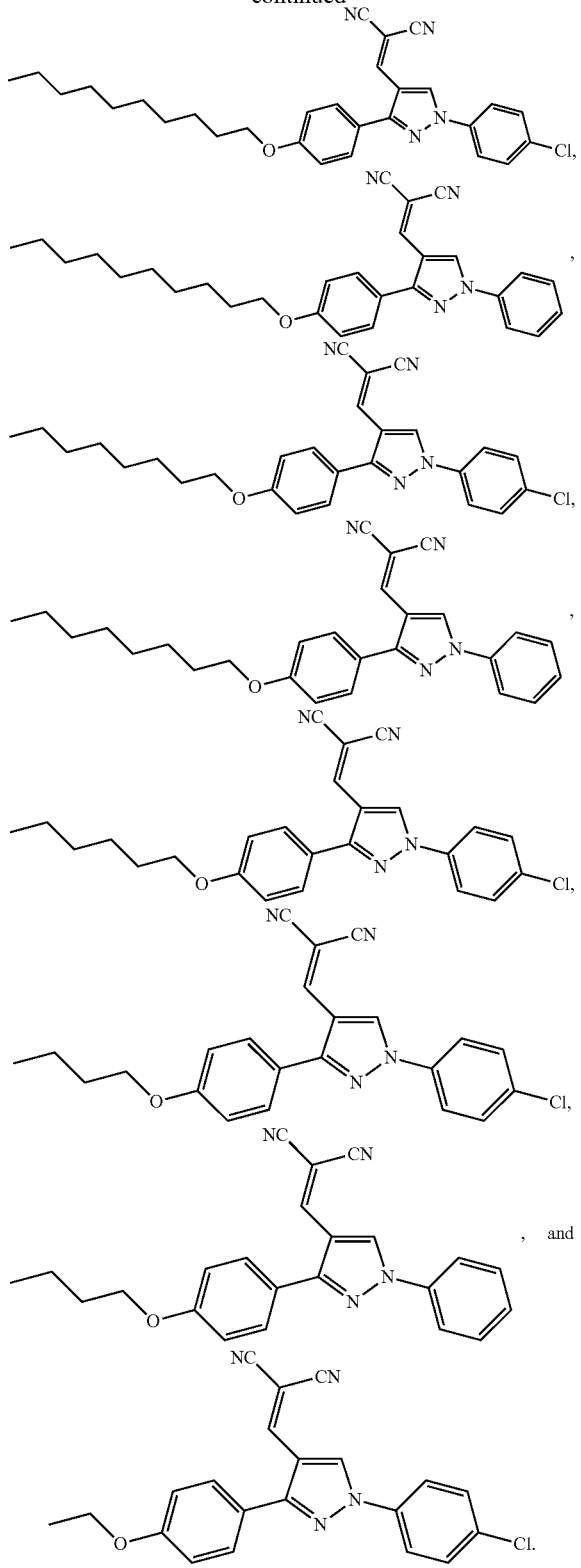

, and

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

The term "alkyl" refers to alkyl groups with the general formula $C_nH_{2n+1}$, where n=about 1 to about 18 or more. The groups can be straight-chained or branched. Alkyl, when used herein, also comprise "lower alkyls," which refer to alkyl groups with the general formula $C_nH_{2n+1}$, where n=1 to about 6. In some embodiments, n=1 to about 3. Examples include methyl, ethyl, propyl, isopropyl, n-butyl, sec-butyl, t-butyl, isobutyl, n-pentyl, isopentyl, neopentyl, n-hexyl, and the like. The alkyl group can be substituted or unsubstituted. For example, the alkyl group can be substituted with one or more groups including, but not limited to, optionally substituted alkyl, cycloalkyl, alkoxy, amino, ether, halide, hydroxy, nitro, silyl, sulfo-oxo, or thiol, as described herein.

In this regard, the term alkyl is inclusive of "cycloalkyl," which refers to a non-aromatic carbon-based rings composed of at least three carbon atoms, such as cyclopropyl, cyclohexyl, and the like. Like other alkyls, cycloalkyls can be substituted or unsubstituted. The substituted moieties can be specifically identified herein; for example, a particular substituted cycloalkyl can be referred to as an "alkylcycloalkyl." Again, the practice of using a general term, such as "cycloalkyl," and a specific term, such as "alkylcycloalkyl," is not meant to imply that the general term does not also include the specific term.

The term "fluorocarbon" refers to compounds that comprise carbon and fluoride bonded together. Fluorocarbons can comprise any type of bond and may be fluoroalkyl, fluoroalkene, or the like. Examples of fluorocarbons include $CF_4$, $C_2F_6$, $C_2F_4$, and the like.

The term "aryl," refers to an aromatic group containing ring carbon atoms and having about 5 to about 14 ring carbon atoms and up to a total of about 18 ring or pendant carbon atoms. Examples include, but are not limited to, phenyl, biphenyl, naphthalene, α-naphthyl, β-naphthyl, tolyl, xylyl, benzene, phenoxybenzene, and the like. The term "aryl" also includes "heteroaryl," which is defined as a group that contains an aromatic group that has at least one heteroatom incorporated within the ring of the aromatic group. Likewise, the term "non-heteroaryl," which is also included in the term "aryl," defines a group that contains an aromatic group that does not contain a heteroatom. The aryl group can be substituted or unsubstituted. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

As described above, each of the groups mentioned herein, including the groups defined above, could be substituted or unsubstituted. For example, "alkyl" can include substituted alkyl, substituted with hydroxyl, heteroatoms, or lower alkyl groups. As a further example, "aryl" can include substituted aryl, substituted with alkyl, cycloalkyl, amino, nitro, thiol, or the like.

Compounds described herein can potentially give rise to cis/trans (E/Z) isomers, as well as other conformational isomers. Unless stated to the contrary, the presently-disclosed subject matter includes all such possible isomers, as well as mixtures of such isomers. Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present compounds all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

The presently-disclosed subject matter further includes pharmaceutical compositions of the compounds as disclosed herein, and further includes a pharmaceutically-acceptable carrier. In this regard, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose.

Suitable formulations include aqueous and non-aqueous sterile injection solutions that can contain antioxidants, buffers, bacteriostats, bactericidal antibiotics and solutes that render the formulation isotonic with the bodily fluids of the intended recipient; and aqueous and non-aqueous sterile suspensions, which can include suspending agents and thickening agents.

The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

The formulations can be presented in unit-dose or multi-dose containers, for example sealed ampoules and vials, and can be stored in a frozen or freeze-dried (lyophilized) condition requiring only the addition of sterile liquid carrier immediately prior to use.

For oral administration, the compositions can take the form of, for example, tablets or capsules prepared by a conventional technique with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycollate); or wetting agents (e.g., sodium lauryl sulphate). The tablets can be coated by methods known in the art.

Liquid preparations for oral administration can take the form of, for example, solutions, syrups or suspensions, or they can be presented as a dry product for constitution with water or other suitable vehicle before use. Such liquid preparations can be prepared by conventional techniques with pharmaceutically acceptable additives such as suspending agents (e.g., sorbitol syrup, cellulose derivatives or hydrogenated edible fats); emulsifying agents (e.g. lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate. Preparations for oral administration can be suitably formulated to give controlled release of the active compound. For buccal administration the compositions can take the form of tablets or lozenges formulated in conventional manner.

The compounds can also be formulated as a preparation for implantation or injection. Thus, for example, the compounds can be formulated with suitable polymeric or hydrophobic materials (e.g., as an emulsion in an acceptable oil) or ion exchange resins, or as sparingly soluble derivatives (e.g., as a sparingly soluble salt).

The compounds can also be formulated in rectal compositions (e.g., suppositories or retention enemas containing conventional suppository bases such as cocoa butter or other glycerides), creams or lotions, or transdermal patches.

The compounds disclosed herein have utility as PGES inhibitors, and in particular, mPGES-1. In this regard, the compounds and pharmaceutical compositions of the presently disclosed subject matter have anti-inflammatory utilities. In this regard, in some embodiments, the pharmaceutical compositions of the presently-disclosed subject matter further include a second compound having PGES inhibition activity, having anti-inflammatory activity, being useful for treatment of an inflammation disorder, and/or being useful for treatment of symptoms associated inflammation and/or an inflammation disorder.

The presently-disclosed subject matter further includes kits. In some embodiments, a kit can include a compound or pharmaceutical composition as described herein, packaged together with a second compound, composition, or treatment device having PGES inhibition activity, having anti-inflammatory activity, being useful for treatment of an inflammation disorder, and/or being useful for treatment of symptoms associated inflammation and/or an inflammation disorder. By way of providing non-limiting examples of treatment devices that could be included in a kit of the presently-disclosed subject matter, inflammation can be treated in some cases with application of a device that changes temperature at a site of interest, e.g., a cooling pack or a heating pack.

In some embodiments, a kit can include a compound or pharmaceutical composition as described herein, packaged together with a device useful for administration of the compound or composition. As will be recognized by those or ordinary skill in the art, the appropriate administration aiding device will depend on the formulation of the compound or composition that is selected and/or the desired administration site. For example, if the formulation of the compound or composition is appropriate for injection in a subject, the device could be a syringe. For another example, if the desired administration site is cell culture media, the device could be a sterile pipette.

The presently-disclosed subject matter further includes methods of inhibiting mPGES. In some embodiments, the method can include contacting any of the compounds or compositions described herein with mPGES-1, thereby forming a complex with the compound and mPGES-1. In some embodiments, the method can include administering an effective amount of a compound or pharmaceutical composition, as described herein, including but not limited to the compounds set forth herein, and compositions thereof.

As will be recognized by one of ordinary skill in the art, the term "inhibiting" or "inhibition" does not refer to the ability to completely inactivate all target biological activity in all cases. Rather, the skilled artisan will understand that the term "inhibiting" refers to decreasing biological activity of a target, such as a prostaglandin E synthase, such as can occur with a ligand binding site of the target is blocked, or when a non-native complex with the target is formed. Such decrease in biological activity can be determined relative to a control, wherein an inhibitor is not administered and/or placed in contact with the target. For example, in some embodiments, a decrease in activity relative to a control can be about a 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% decrease. The term "inhibitor" refers to a compound of composition that inactivates or decreases the biological activity of a target, such as a prostaglandin E synthase.

Without being bound by theory or mechanism, in some embodiments the compounds disclosed herein inhibit mPGES-1 by blocking its interaction with the $PGH_2$, COX-2, or other substrates. Thus, the presently-disclosed subject matter also includes methods that find utility from the blocking mPGES-1 interaction with $PGH_2$, COX-2, or other substrates. In this regard, the presently-disclosed subject matter includes methods of reducing and/or inhibiting inflammation, and methods of treating an inflammation disorder, and/or symptoms associated inflammation and/or an inflammation disorder. Such methods can include administering an effective amount of a compound of pharmaceutical composition as described herein to a subject. Non-limiting examples of inflammation disorders include inflammation, arthritis, fever, pain, cancer, stroke, and bone disorders In some embodiments of a method of treating an inflammation disorder or symptoms thereof in a subject in need thereof, the method includes administering to the subject an effective amount of a compound, including any of the compounds described above. In some embodiments the compound inhibits prostaglandin E synthase (PGES), and in particular, some embodiments inhibit microsomal PGES-1 (mPGES-1). Thus, some embodiments include a method for inhibiting mPGES-1, comprising administering to a subject an effect amount of a compound, including any of the compounds described above.

The terms "treatment" or "treating" refer to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The terms "subject" or "subject in need thereof" refer to a target of administration, which optionally displays symptoms related to a particular disease, pathological condition, disorder, or the like. The subject of the herein disclosed methods can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. A patient refers to a subject afflicted with a disease or disorder. The term "patient" includes human and veterinary subjects.

In some embodiments, compounds disclosed herein that are mPGES-1 inhibitors are potent against both human and mouse mPGES-1 enzymes.

The term "administering" refers to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition.

In further various aspects, a preparation can be administered prophylactically; that is, administered for prevention of a disease or condition.

The term "effective amount" refers to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side affects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

The presently-disclosed subject matter further includes methods for selecting and synthesizing embodiments of the present invention can utilize structure-based virtual screening to identify small-molecule inhibitors from a large drug-like database. In some embodiments a large database of lead compounds can be virtually screened to retrieve putative mPGES-1 inhibitors. From that screening, essential amino acids involved in antagonist recognition can be identified and a primary topographical interaction model can be made to guide subsequent virtual screening processes. Without being bound by theory or mechanism, an inhibitor's binding pocket of the mPGES-1 protein can overlap with both the binding site of the $PGH_2$ substrate and GSH cofactor in mPGES-1 protein.

The presently-disclosed subject matter is further illustrated by the following specific but non-limiting examples. Some examples are prophetic. Some of the following examples may include compilations of data that are representative of data gathered at various times during the course of development and experimentation related to the presently-disclosed subject matter.

EXAMPLES

Example 1 Synthetic Protocol Compounds of Formula I

Figure 2:
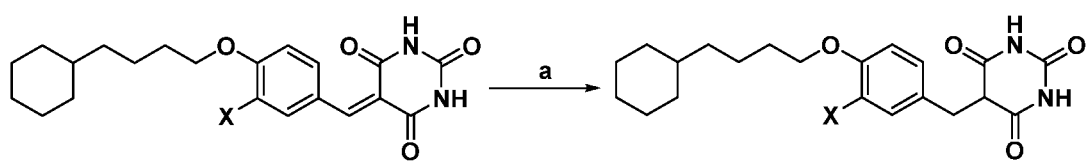
FIG. 2 shows a schematic view of the synthesis of a specific compound having the structure of formula I, according to an embodiment of the disclosure. Reagents and conditions: (a) 1) $NaBH_4$ (1.25 equiv.), MeOH, 0° C.~rt, 2) 1 M HCl solution, rt.

The synthesis of BAR series (compounds of Formula I) can be generally described by the schemes illustrated in FIG. 1 and FIG. 2 of this Example. (for BAR042~044).

The substituted hydroxybenzaldehyde or hydroxy naphthaldehyde was treated with alcohol tosylate or alkyl bromide in the presence of potassium carbonate as acid capturer.[25,26] The forming aldehyde intermediate was usually pure enough after aqueous work-up and removal of solvents which could be used for the subsequent step without further purification. However, analytical samples could be obtained by flash chromatography using a mixture of hexanes and ethyl acetate as eluent. The final product, substituted benzylidenebarbituric acid derivatives were obtained by the condensation of the aldehyde intermediate and barbituric acid (or 1,3-dimethylbarbituric acid, 2-thiobarbituric acid) in reflux ethanol/water (4:1, v/v).[27,28] The precipitate formed was washed with hot water and ethanol, and dried under vacuum to form the analytical pure sample.

I-42~I-44 were synthesized by the reduction of benzylidene double bond of I-02, I-03, and I-08, using sodium borohydride in methanol as reducing agent solution.[29]

Example 2 Synthetic Protocol of the Compounds of Formula II

Figure 3:
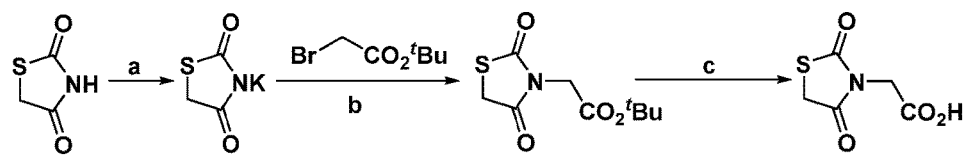
FIG. 3 shows a schematic view of the general synthesis of compounds having the structure of formula II, according to an embodiment of the disclosure. Reagents and conditions: (a) Triphenylphosphine (1.20 equiv.), DIAD (1.20 equiv.), THF, 0° C.~rt; (b) actone, reflux; (c) TFA/DCM (1:1, v/v), rt; (d) $K_2CO_3$ (2.0 equiv.), DMF, 80° C.; (e) Pd(dppf)$Cl_2$ $CH_2Cl_2$ (0.03 equiv.), $NaHCO_3$ (2.50 equiv.), DME/$H_2O$, reflux, $N_2$ atmosphere; (f) ammonium acetate (2.00 equiv.), glacial acetic acid, reflux.
Figure 3:
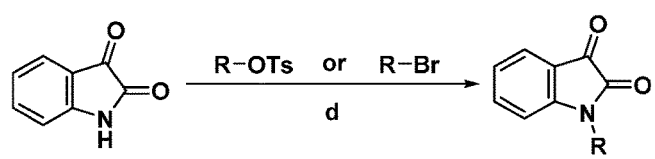
Figure 3:
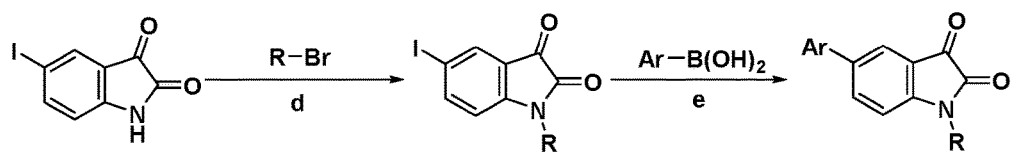
Figure 3:
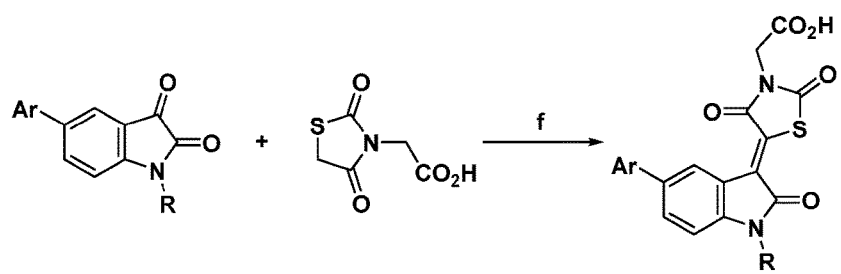

Commercially available isatin (or 5-iodoisatin) and 2,4-thiazolidinedione were used as starting materials to construct the building blocks of substituted isatin and 2,4-thiazolidinedione N-acetic acid, respectively. After treatment with potassium hydroxide in hot ethanol, the potassium salt of 2,4-thiazolidinedione was precipitated out for the N-substitution by tert-butyl bromoacetate. The removal of tert-butyl ester in TFA/DCM (1:1, v v) at room temperature led to the formation of important building block 2,4-thiazolidinedione N-acetic acid.[32] N-substituted isation was prepared by potassium carbonate promoted reaction between isatin and alkyl bromide (or alcohol tosylate if the bromide was not commercially available).[33] While for 1,5-disubstituted isatin, N-substitution on 5-iodoisatin by 4-chlorobenzyl bromide in the presence of potassium carbonate was followed by the Suzuki cross-coupling reaction with aryl boronic acid ($ArB(OH)_2$) using [1,1'-Bis(diphenylphosphino)ferrocene]dichloropalladium(II) complex with dichloromethane (0) as catalyst and sodium bicarbonate as base activator in refluxing dimethoxyethane (DME) and distilled water ($DME/H_2O$ 4:1) under the protection of nitrogen gas.[34,35] The final product was obtained as red to brown powders by the Knovenagal-type condensation of the isatin-based building block with 2,4-thiazolidinedione N-acetic acid in the presence of ammonium acetate in refluxing glacial acetic acid, as described in FIG. 3.

Figure 4:
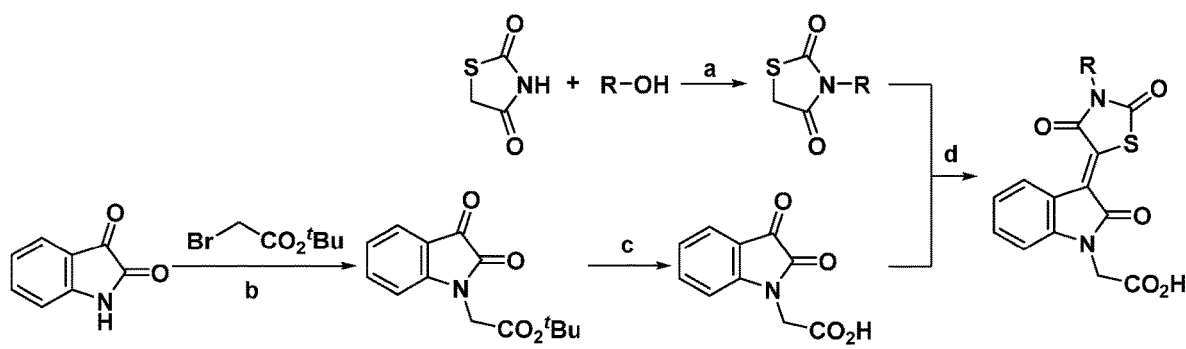
FIG. 4 shows a schematic view of the synthesis of a specific compound having the structure of formula II, according to an embodiment of the disclosure. Reagents and conditions: (a) Triphenylphosphine (1.20 equiv.), DIAD (1.20 equiv.), THF, 0° C.~rt; (b) $K_2CO_3$ (2.0 equiv.), DMF, 80° C.; (c) TFA/DCM (1:1, v v), rt; (d) $NH_4OAc$ (2.00 equiv.), glacial AcOH, reflux.

Some of the compounds in this series were designed by switching the positions of hydrophilic and hydrophobic groups, as Cy4TZISA, whose acetic acid group occupied N-position of isatin and aliphatic group linked to 2,4-thiazolidinedione moiety. These compounds were readily synthesized following similar protocol as described previously, as shown in FIG. 4.

Example 3 Synthetic Protocol of Compounds of Formulae III and IV (Maleimide Derivatives and Substituted Dinitrobenzene Derivatives)

Figure 5:
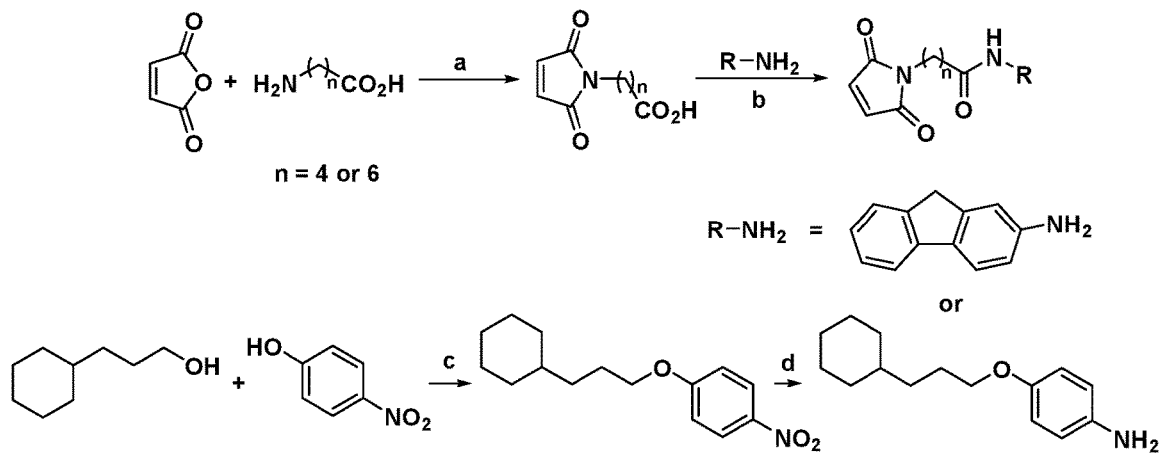
FIG. 5 shows a schematic view of the general synthesis of compounds having the structure of formula III, according to an embodiment of the disclosure. Reagents and conditions: (a) Glacial AcOH, reflux; (b) HBTU (1.10 equiv.), DIPEA (3.30 equiv.), DMF, 0° C.~rt; (c) Triphenylphosphine (1.20 equiv.), DIAD (1.20 equiv.), THF, 0° C.~rt; (d) $H_2$, Pd/C (10% w/w), THF/MeOH (4:1 v v), rt.

Maleimide derivatives were synthesized via the condensation of 4-maleimidobutyric acid or 6-maleimidohexanoic acid[36] with aryl amines,[37] as shown in FIG. 5.

Figure 6:
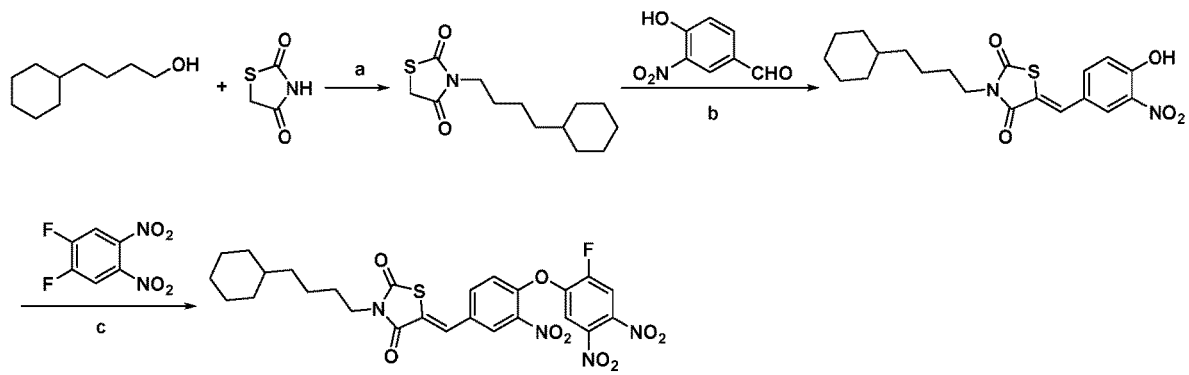
FIG. 6 shows a schematic view of the general synthesis of compounds having the structure of formula IV, according to an embodiment of the disclosure. Reagents and conditions: (a) Triphenylphosphine (1.20 equiv.), DIAD (1.20 equiv.), THF, 0° C.~rt; (b) NH$_4$OAc (2.00 equiv.), glacial AcOH, reflux; (c) K$_2$CO$_3$ (2.0 equiv.), DMF, 80° C.

In the synthesis of dinitrobenzene derivatized potent inhibitors, the oxygen on phenyl derivative nucleophilically substituted one of the fluorine atom on 1,2-difluoro-4,5-dinitrobenzene using potassium carbonate as acid capturer, as shown in FIG. 6.[38]

Example 4 Synthetic Protocol of Compounds of Formula V

Figure 7:
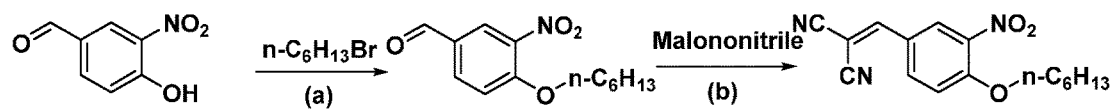
FIG. 7 shows a schematic view of the general synthesis of compounds having the structure of formula V, according to an embodiment of the disclosure. Reagents and conditions: (a) K$_2$CO$_3$ (2.00 equiv.), DMF, 80° C.; (b) Malononitrile, NH$_4$OAc (2.00 equiv.), AcOH, reflux.

The compounds of Formula V were prepared following a two-step protocol.[39-42] O-Substitution of substituted 4-hydroxybenzaldehyde afforded the aldehyde intermediate and the latter was coupled with malononitrile, 2-cyanoacetic acid or 2-cyanoacetamide. An example of the synthesis of V-04 is illustrated in FIG. 7.

Example 5 Synthetic Protocol of Compounds of Formulae VI and VII

Figure 8:
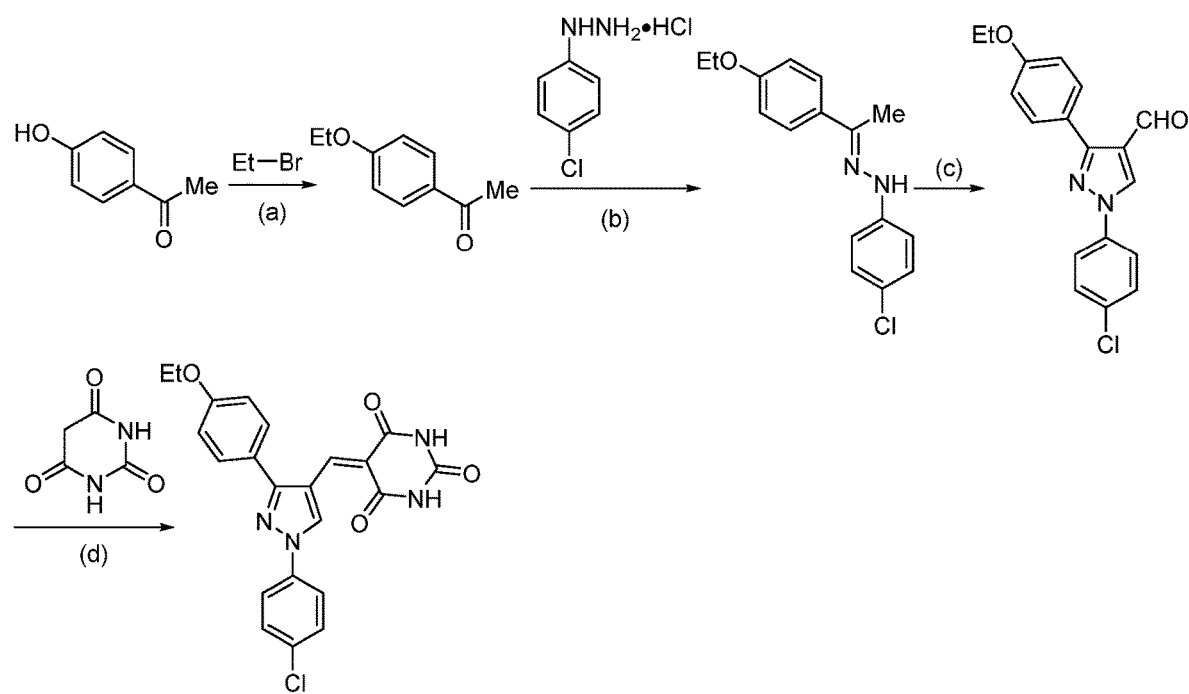
FIG. 8 shows a schematic view of the general synthesis of compounds having the structure of formula VI, according to an embodiment of the disclosure. Reagents and conditions: (a) K$_2$CO$_3$ (2.00 equiv.), DMF, 80° C.; (b) 5% glacial AcOH in EtOH, reflux; (c) POCl$_3$ (4.00 equiv.), DMF, 0° C.~60° C.; (d) EtOH/H$_2$O (4:1, v/v), reflux.

The compounds of Formula VI were synthesized according to a multi-step protocol. 4-Alkyloxyacetophenone, obtained from the reaction of 4-hydroxyacetophenone and alkyl bromide, or acetophenone was condensed with 4-chlorophenylhydrazine in reflux ethanol containing 5% glacial acetic acid. The ethylidene hydrazine was formed as precipitate at room temperature and filtered off. The next step was Vilsmeier-Haack-Arnold ring closing formylation, by treating with $POCl_3$/DMF. The produced 1H-pyrazole-4-carbaldehyde intermediate was coupled with barbituric acid or 2-thiobarbituric acid in refluxing EtOH/$H_2O$ (4:1) to afford the final product. The synthetic protocol for compounds with Formula VII followed similar strategy as those with formula VI, except the final step which was the coupling with 2,4-thiazolidinedione derivatives. An example of the synthesis of VI-01 is depicted in FIG. 8.

Example 6 Characterization of Inhibition In Vitro

Studies were conducted to characterize the inhibitory activity against recombinant mPGES-1 of the compounds synthesized in accordance with Examples 1-4, and disclosed herein.

Briefly, FreeStyle 293-F cells were cultured following manufacturer's manual in FreeStyle 293 expression medium on orbit rotate shaker in 8% $CO_2$ incubator at 37° C. Cells were transfected with 1.5 μg/mL of mPGES-1/pcDNA3 construct using FreeStyle Max reagent at a cell density of $1 \times 10^6$ for 2 days. Transfected cells were collected, washed, and sonicated in TSES buffer (15 mM Tris-HCl, pH 8.0 plus 0.25 M sucrose, 0.1 mM EDTA and 1 mM DTT) on ice. The broken cells were first centrifuged at 12,500×g for 10 min. The supernatant was further centrifuged at 105,000×g for 1 hr at 4° C. The pellet was washed and homogenized in PBS buffer. The crude microsomal mPGES-1 preparation was aliquoted and stored at −80° C. The crude protein concentration was 8 mg/mL.

The enzyme activity assays were performed on ice in 1.5 ml microfuge tubes by using the expressed mPGES-1. The reaction mixture contained: 0.2 M $Na_2HPO_4$/$NaH_2PO_4$, pH 7.2, 10 μL; 0.1 M GSH, 2.5 μL; diluted microsomal enzyme (80 μg/mL), 1 μL; $PGH_2$ (0.31 mM in DMF), 5 μL; 1 μL inhibitor; and $H_2O$ in a final reaction volume of 100 μL. $PGH_2$ was stored in dry ice and used to initiate the reaction.

Compounds were incubated with the enzyme for 15 min at room temperature before the addition of cold $PGH_2$ (1 μM final) to initiate the enzyme reaction. After 30 s, 10 μL of $SnCl_2$ (40 mg/mL) in ethanol was added to stop the reaction. The nonenzymatic conversion of $PGH_2$ to $PGE_2$ was performed in the same buffer devoid of enzyme. The reaction mixture was placed on ice until $PGE_2$ production was determined by the $PGE_2$ enzyme immunoassay as described earlier. $IC_{50}$ values of the inhibitors were calculated by using the GraphPad Prism 4.0 program. The results are set forth in the tables provided in Examples 7-10.

Example 7 Characterization of Inhibition of Compounds of Formula I

TABLE 1

| Compound | Structure | $IC_{50}^a$ against mPGES-1 (nM) | |
|---|---|---|---|
| | | Human enzyme | Mouse enzyme |
| I-01 | 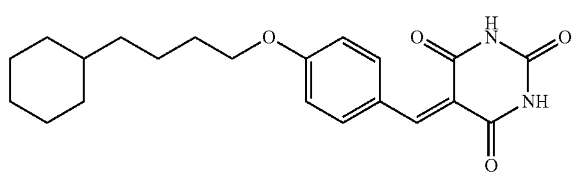 [SMILES: O=C1NC(=O)C(=Cc2ccc(OCCCCC3CCCCC3)cc2)C(=O)N1] | 622 ± 121 | 7079 ± 627 |
| I-02 | 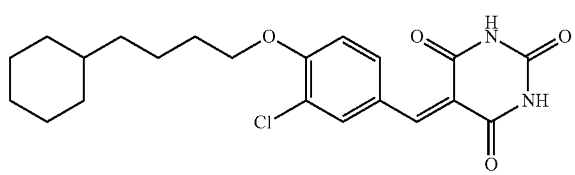 [SMILES: O=C1NC(=O)C(=Cc2ccc(OCCCCC3CCCCC3)c(Cl)c2)C(=O)N1] | 33 ± 3 | 157 ± 31 |
| I-03 | 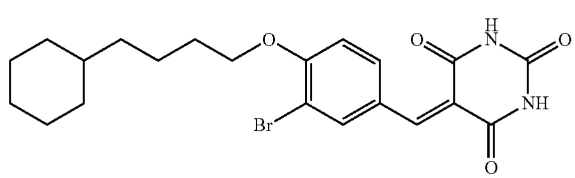 [SMILES: O=C1NC(=O)C(=Cc2ccc(OCCCCC3CCCCC3)c(Br)c2)C(=O)N1] | 45 ± 8 | 917 ± 321 |

TABLE 1-continued
| Compound | Structure | IC$_{50}$[a] against mPGES-1 (nM) | |
| --- | --- | --- | --- |
| | | Human enzyme | Mouse enzyme |
| I-04 | 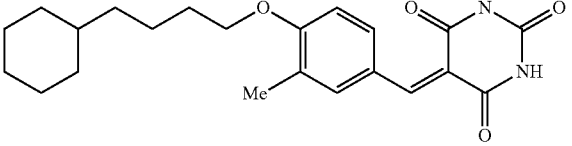 | 82 ± 10 | n.d.[b] (25)[c] |
| I-05 | 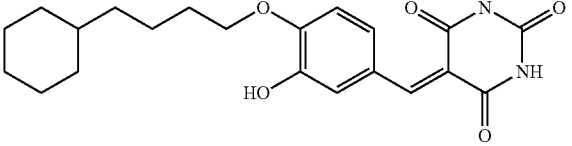 | 116 ± 17 | 2900 ± 293 |
| I-06 | 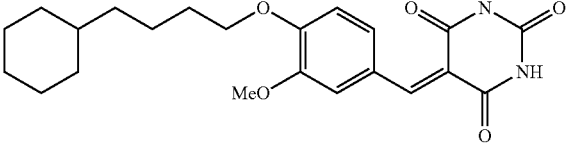 | 121 ± 20 | 1458 ± 209 |
| I-07 | 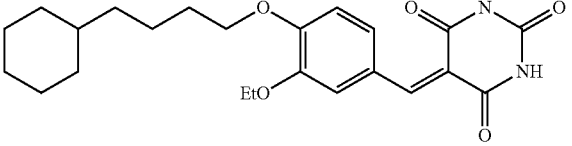 | 186 ± 26 | 2409 ± 339 |
| I-08 | 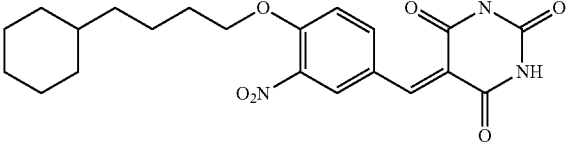 | 67 ± 20 | 698 ± 97 |
| I-09 | 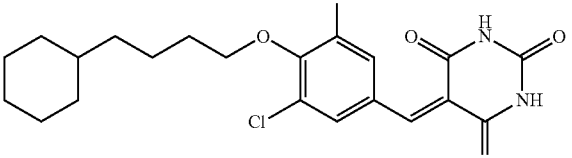 | 22 ± 7 | 360 ± 56 |
| I-10 | 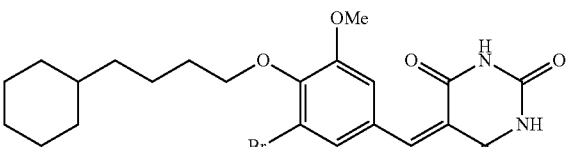 | 69 ± 16 | 292 ± 47 |
| I-11 | 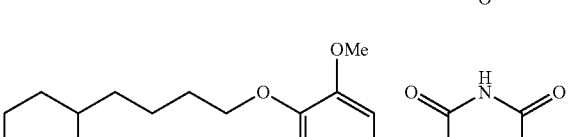 | 54 ± 12 | 359 ± 50 |

TABLE 1-continued
| Compound | Structure | IC$_{50}$$^a$ against mPGES-1 (nM) | |
| --- | --- | --- | --- |
| | | Human enzyme | Mouse enzyme |
| I-12 | 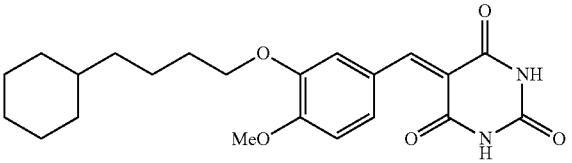 [SMILES: COc1ccc(C=C2C(=O)NC(=O)NC2=O)cc1OCCCCC1CCCCC1] | 152 ± 53 | 727 ± 109 |
| I-13 | 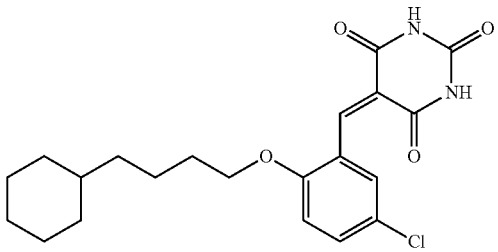 | 87 ± 27 | n.d. (28) |
| I-14 | 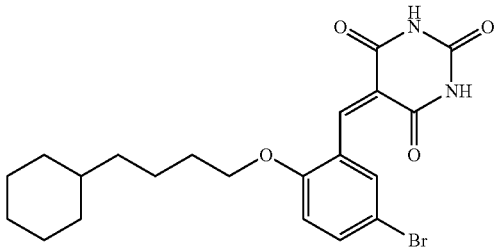 [SMILES: O=C1NC(=O)C(=Cc2cc(Cl)ccc2OCCCCC2CCCCC2)C(=O)N1] | 96 ± 14 | n.d. (38) |
| I-15 | 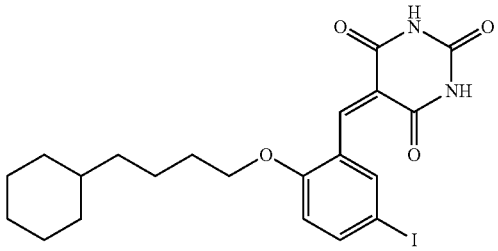 [SMILES: O=C1NC(=O)C(=Cc2cc(I)ccc2OCCCCC2CCCCC2)C(=O)N1] | 135 ± 18 | 12078 ± 1963 |
| I-16 | 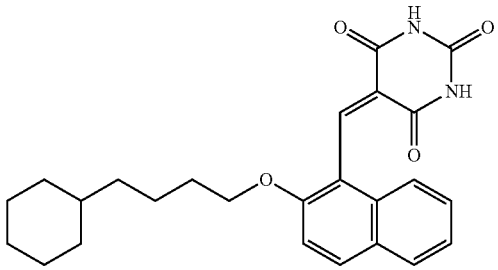 [SMILES: O=C1NC(=O)C(=Cc2c(OCCCCC3CCCCC3)ccc3ccccc23)C(=O)N1] | 154 ± 18 | 7039 ± 1853 |
| I-17 | 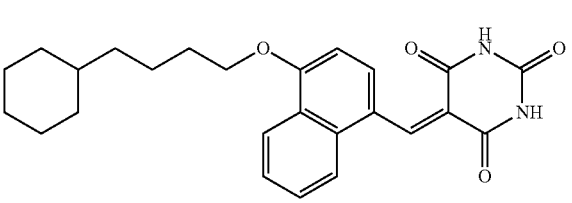 [SMILES: O=C1NC(=O)C(=Cc2ccc(OCCCCC3CCCCC3)c3ccccc23)C(=O)N1] | 171 ± 34 | 3699 ± 562 |

TABLE 1-continued

| Compound | Structure | IC$_{50}$$^a$ against mPGES-1 (nM) | |
| --- | --- | --- | --- |
| | | Human enzyme | Mouse enzyme |
| I-18 | 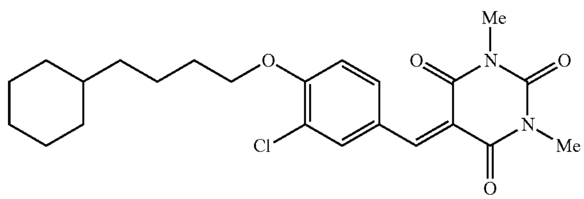 [SMILES: CN1C(=O)C(=Cc2ccc(OCCCCC3CCCCC3)c(Cl)c2)C(=O)N(C)C1=O] | 272 ± 30 | n.d. (8) |
| I-19 | 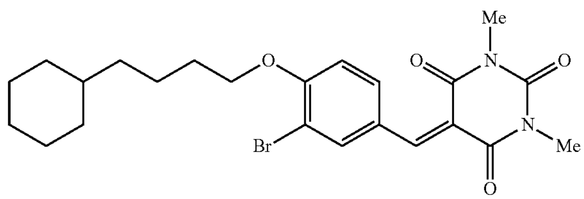 [SMILES: CN1C(=O)C(=Cc2ccc(OCCCCC3CCCCC3)c(Br)c2)C(=O)N(C)C1=O] | 427 ± 55 | n.d. (24) |
| I-20 | 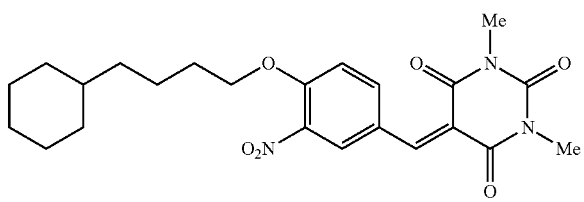 [SMILES: CN1C(=O)C(=Cc2ccc(OCCCCC3CCCCC3)c([N+](=O)[O-])c2)C(=O)N(C)C1=O] | 561 ± 55 | n.d. (15) |
| I-21 | 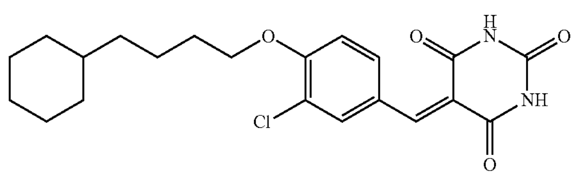 [SMILES: O=C1NC(=O)C(=Cc2ccc(OCCCCC3CCCCC3)c(Cl)c2)C(=O)N1] | 28 ± 3 | 415 ± 120 |
| I-22 | 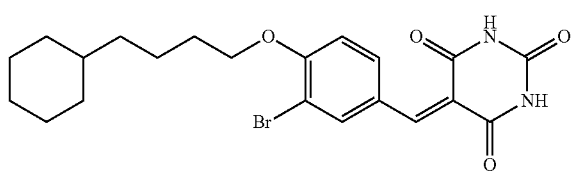 [SMILES: O=C1NC(=O)C(=Cc2ccc(OCCCCC3CCCCC3)c(Br)c2)C(=O)N1] | 20 ± 4 | 239 ± 72 |
| I-23 | 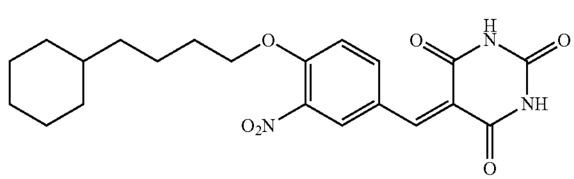 [SMILES: O=C1NC(=O)C(=Cc2ccc(OCCCCC3CCCCC3)c([N+](=O)[O-])c2)C(=O)N1] | 53 ± 14 | 9013 ± 1044 |
| I-24 | 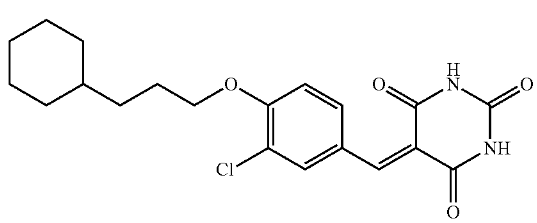 [SMILES: O=C1NC(=O)C(=Cc2ccc(OCCCC3CCCCC3)c(Cl)c2)C(=O)N1] | 110 ± 21 | 979 ± 84 |

TABLE 1-continued
| Compound | Structure | IC$_{50}$[a] against mPGES-1 (nM) | |
|---|---|---|---|
| | | Human enzyme | Mouse enzyme |
| I-25 | 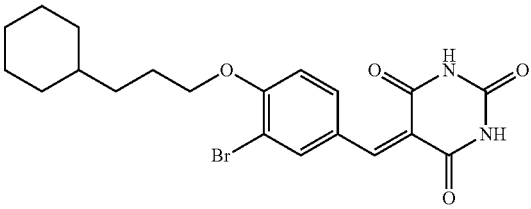 | 104 ± 25 | 336 ± 43 |
| I-26 | 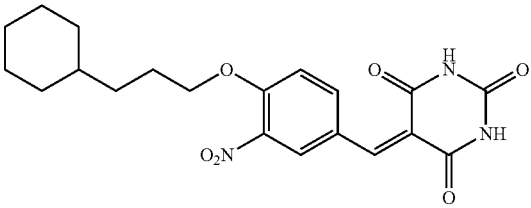 [SMILES: O=C1NC(=O)C(=Cc2ccc(OCCCC3CCCCC3)c([N+](=O)[O-])c2)C(=O)N1] | 156 ± 30 | 373 ± 51 |
| I-27 | 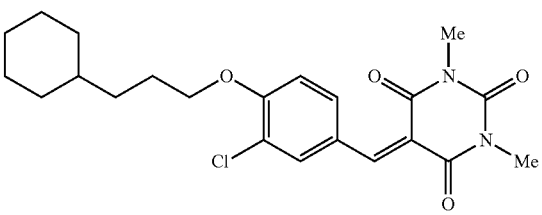 [SMILES: CN1C(=O)C(=Cc2ccc(OCCCC3CCCCC3)c(Cl)c2)C(=O)N(C)C1=O] | 240 ± 20 | n.d. (29) |
| I-28 | 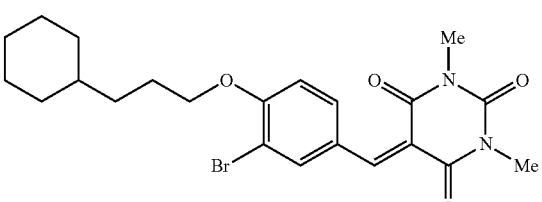 | 127 ± 14 | n.d. (30) |
| I-29 | 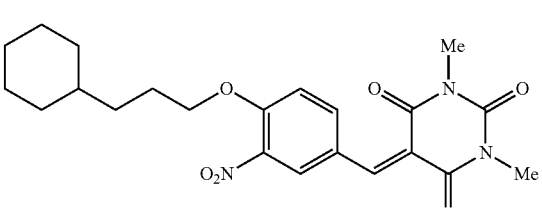 | 188 ± 21 | n.d. (41) |
| I-30 | 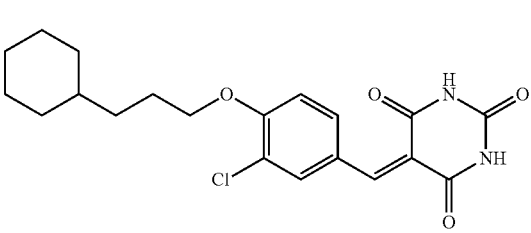 [SMILES: O=C1NC(=O)C(=Cc2ccc(OCCCC3CCCCC3)c(Cl)c2)C(=O)N1] | 78 ± 13 | 3231 ± 460 |
| I-31 | 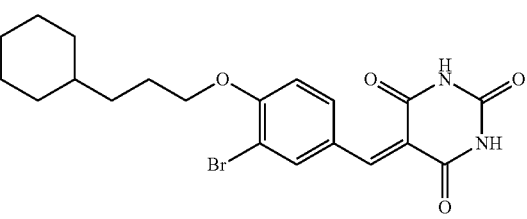 | 112 ± 13 | 1444 ± 222 |

TABLE 1-continued

| Compound | Structure | IC$_{50}$$^a$ against mPGES-1 (nM) | |
| --- | --- | --- | --- |
| | | Human enzyme | Mouse enzyme |
| I-32 | 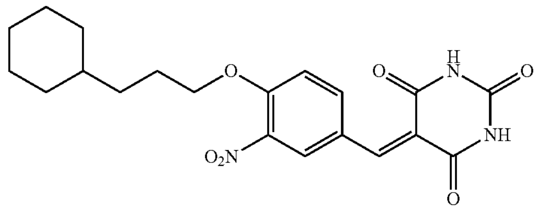 [SMILES: O=C1NC(=O)C(=Cc2ccc(OCCCC3CCCCC3)c([N+](=O)[O-])c2)C(=O)N1] | 73 ± 12 | 428 ± 58 |
| I-33 | 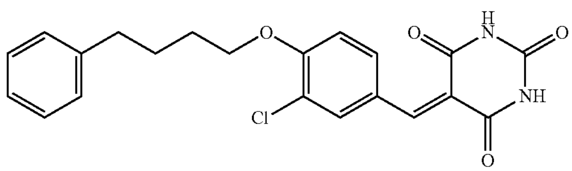 [SMILES: O=C1NC(=O)C(=Cc2ccc(OCCCCc3ccccc3)c(Cl)c2)C(=O)N1] | 73 ± 10 | 2788 ± 525 |
| I-34 | 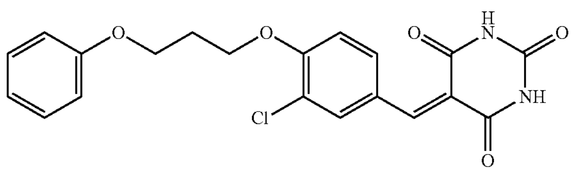 [SMILES: O=C1NC(=O)C(=Cc2ccc(OCCCOc3ccccc3)c(Cl)c2)C(=O)N1] | 349 ± 40 | 8126 ± 1012 |
| I-35 | 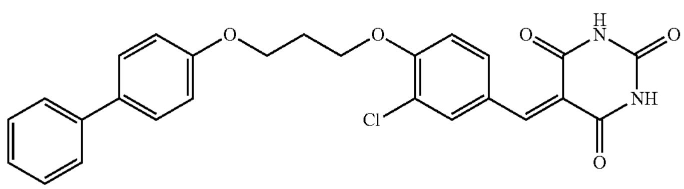 [SMILES: O=C1NC(=O)C(=Cc2ccc(OCCCOc3ccc(-c4ccccc4)cc3)c(Cl)c2)C(=O)N1] | 337 ± 34 | n.d. (17) |
| I-36 | 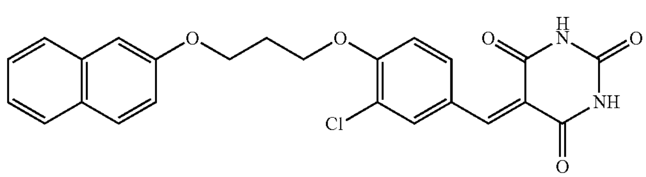 [SMILES: O=C1NC(=O)C(=Cc2ccc(OCCCOc3ccc4ccccc4c3)c(Cl)c2)C(=O)N1] | 365 ± 59 | n.d. (19) |
| I-37 | 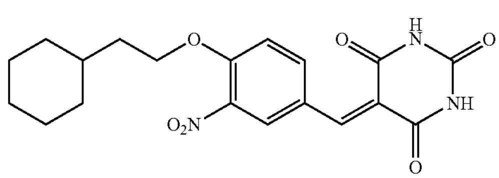 [SMILES: O=C1NC(=O)C(=Cc2ccc(OCCC3CCCCC3)c([N+](=O)[O-])c2)C(=O)N1] | 517 ± 68 | 2395 ± 425 |
| I-38 | 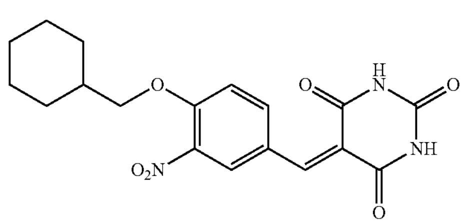 [SMILES: O=C1NC(=O)C(=Cc2ccc(OCC3CCCCC3)c([N+](=O)[O-])c2)C(=O)N1] | 1114 ± 104 | n.d. (42) |
| I-39 | 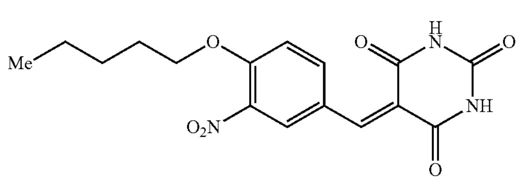 [SMILES: CCCCCOc1ccc(C=C2C(=O)NC(=O)NC2=O)cc1[N+](=O)[O-]] | 460 ± 64 | 6306 ± 1136 |

TABLE 1-continued

| Compound | Structure | IC$_{50}$[a] against mPGES-1 (nM) | |
|---|---|---|---|
| | | Human enzyme | Mouse enzyme |
| I-40 | [structure] | 232 ± 54 | 734 ± 119 |
| I-41 | [structure] | 188 ± 43 | 1303 ± 163 |
| I-42 | [structure] | 133 ± 20 | 1333 ± 151 |
| I-43 | [structure] | 97 ± 13 | 1092 ± 211 |
| I-44 | [structure] | 136 ± 23 | 3354 ± 560 |

[a]Data are expressed as means ± SD of single determinations obtained in triplicate.
[b]n.d. = not detected.
[c]The % inhibition of the compound at a concentration of 10 μM against mPGES-1 (IC$_{50}$ values were determined if the compounds resulted in 50% or higher inhibition).

Example 8 Characterization of Inhibition of Compounds of Formula II

TABLE 2

| Compound | Structure | IC$_{50}$[a] against mPGES-1 (nM) | |
|---|---|---|---|
| | | Human enzyme | Mouse enzyme |
| II-01 | [structure] | 817 ± 79 | n.d.[b] (10)[c] |

TABLE 2-continued

| Compound | Structure | IC$_{50}$$^a$ against mPGES-1 (nM) | |
|---|---|---|---|
| | | Human enzyme | Mouse enzyme |
| II-02 | 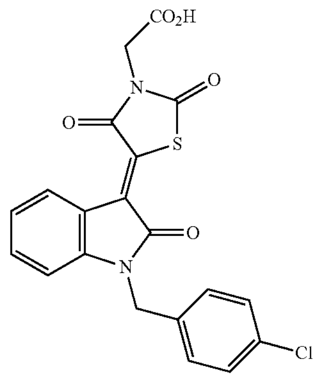 [SMILES: O=C(O)CN1C(=O)S/C(=C2\C(=O)N(Cc3ccc(Cl)cc3)c3ccccc32)C1=O] | 614 ± 63 | n.d. (45) |
| II-03 | 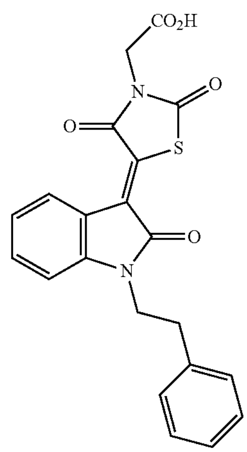 [SMILES: O=C(O)CN1C(=O)S/C(=C2\C(=O)N(CCc3ccccc3)c3ccccc32)C1=O] | 348 ± 44 | n.d. (62) |
| II-04 | 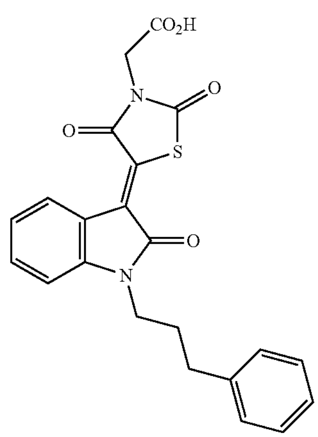 [SMILES: O=C(O)CN1C(=O)S/C(=C2\C(=O)N(CCCc3ccccc3)c3ccccc32)C1=O] | 2403 ± 132 | 747 ± 163 |

TABLE 2-continued

| Compound | Structure | IC$_{50}$$^a$ against mPGES-1 (nM) | |
| --- | --- | --- | --- |
| | | Human enzyme | Mouse enzyme |
| II-05 | [structure: thiazolidinedione-oxindole with N-(4-phenylbutyl) substituent and N-CH$_2$CO$_2$H] | 963 ± 87 | n.d. (61) |
| II-06 | [structure: thiazolidinedione-oxindole with N-(cyclohexylmethyl) substituent and N-CH$_2$CO$_2$H] | 1269 ± 104 | 2728 ± 422 |
| II-07 | [structure: thiazolidinedione-oxindole with N-(2-cyclohexylethyl) substituent and N-CH$_2$CO$_2$H] | 494 ± 32 | n.d. (39) |

TABLE 2-continued
| Compound | Structure | IC$_{50}$$^a$ against mPGES-1 (nM) | |
| --- | --- | --- | --- |
| | | Human enzyme | Mouse enzyme |
| II-08 | 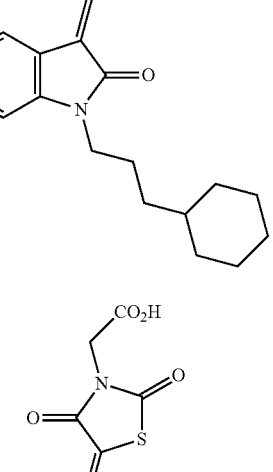 | 253 ± 30 | 1518 ± 317 |
| II-09 | 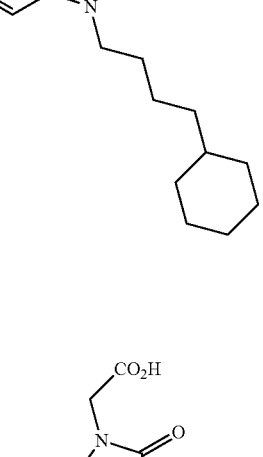 | 499 ± 108 | 947 ± 183 |
| II-10 | 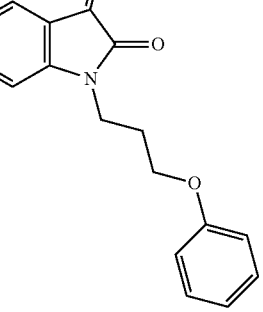 | 805 ± 100 | n.d. (41) |

TABLE 2-continued
| Compound | Structure | IC$_{50}$$^a$ against mPGES-1 (nM) | |
|---|---|---|---|
| | | Human enzyme | Mouse enzyme |
| II-11 | 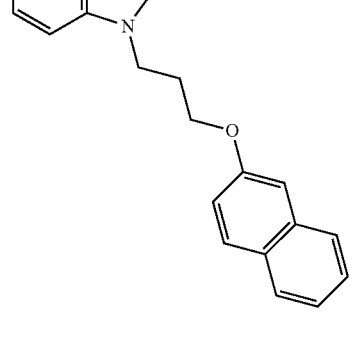 | 1681 ± 168 | 1023 ± 131 |
| II-12 | 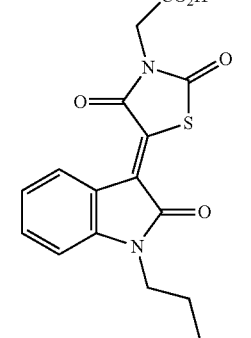 | 1661 ± 168 | n.d. (35) |
| II-13 | 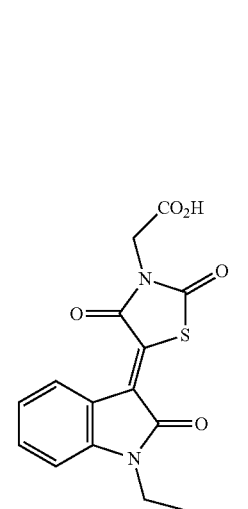 | 1073 ± 116 | n.d. (57) |

TABLE 2-continued
| Compound | Structure | IC$_{50}$$^a$ against mPGES-1 (nM) | |
| --- | --- | --- | --- |
| | | Human enzyme | Mouse enzyme |
| II-14 | 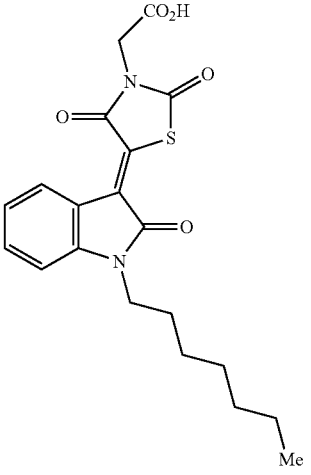 [SMILES: CCCCCCCN1C(=O)/C(=C2\SC(=O)N(CC(=O)O)C2=O)c2ccccc21] | 324 ± 44 | n.d. (67) |
| II-15 | 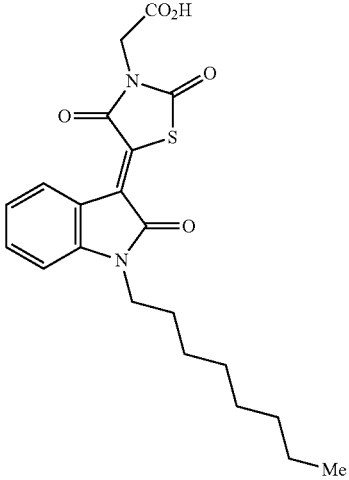 [SMILES: CCCCCCCCN1C(=O)/C(=C2\SC(=O)N(CC(=O)O)C2=O)c2ccccc21] | 314 ± 44 | 2676 ± 302 |
| II-16 | 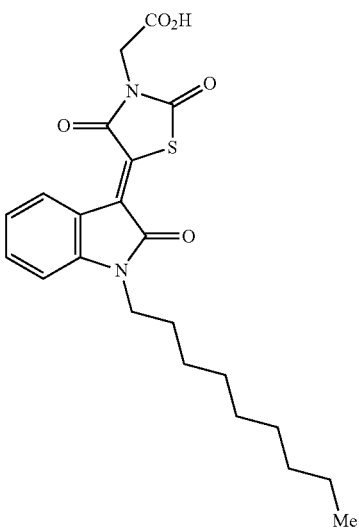 [SMILES: CCCCCCCCCN1C(=O)/C(=C2\SC(=O)N(CC(=O)O)C2=O)c2ccccc21] | 199 ± 32 | 1398 ± 217 |

TABLE 2-continued

| Compound | Structure | IC$_{50}{}^a$ against mPGES-1 (nM) | |
| --- | --- | --- | --- |
| | | Human enzyme | Mouse enzyme |
| II-17 | 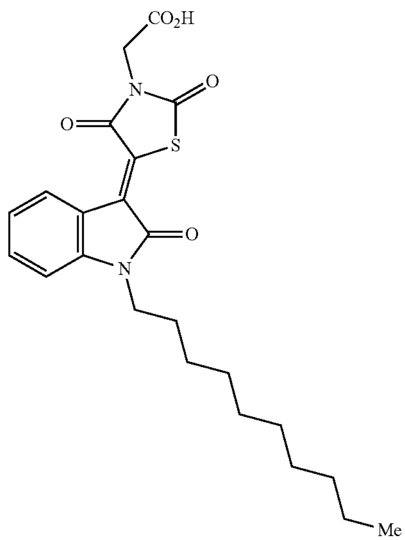 [SMILES: CCCCCCCCCCN1C(=O)/C(=C2\SC(=O)N(CC(=O)O)C2=O)c2ccccc21] | 217 ± 30 | 935 ± 135 |
| II-18 | 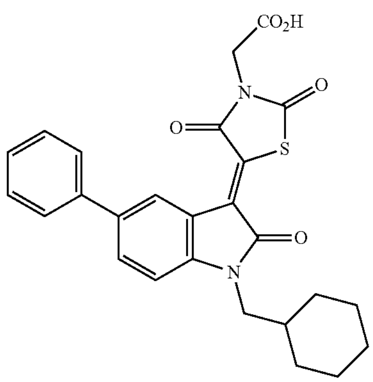 [SMILES: O=C(O)CN1C(=O)S/C(=C2\C(=O)N(CC3CCCCC3)c3ccc(-c4ccccc4)cc32)C1=O] | 221 ± 47 | 394 ± 58 |
| II-19 | 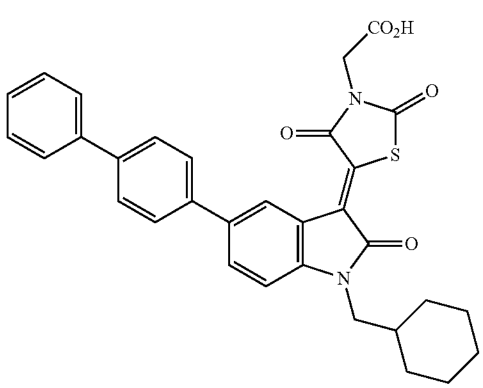 [SMILES: O=C(O)CN1C(=O)S/C(=C2\C(=O)N(CC3CCCCC3)c3ccc(-c4ccc(-c5ccccc5)cc4)cc32)C1=O] | 154 ± 20 | 1020 ± 162 |

TABLE 2-continued
| Compound | Structure | IC$_{50}$$^a$ against mPGES-1 (nM) | |
| --- | --- | --- | --- |
| | | Human enzyme | Mouse enzyme |
| II-20 | 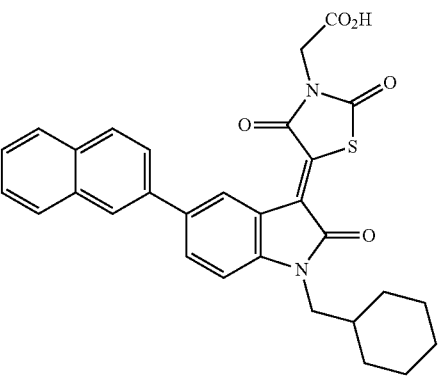 [SMILES: O=C(O)CN1C(=O)S/C(=C2\C(=O)N(CC3CCCCC3)c3ccc(-c4ccc5ccccc5c4)cc32)C1=O] | 531 ± 90 | 244 ± 31 |
| II-21 | 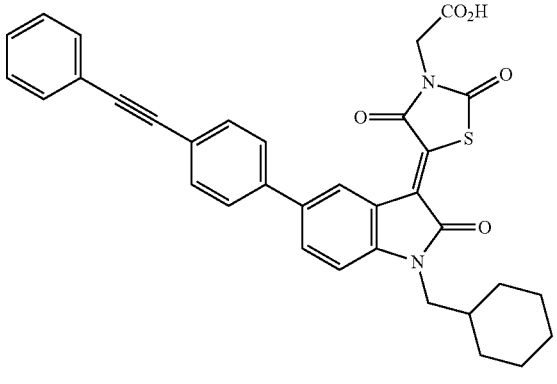 [SMILES: O=C(O)CN1C(=O)S/C(=C2\C(=O)N(CC3CCCCC3)c3ccc(-c4ccc(C#Cc5ccccc5)cc4)cc32)C1=O] | 91 ± 23 | 1960 ± 348 |
| II-22 | 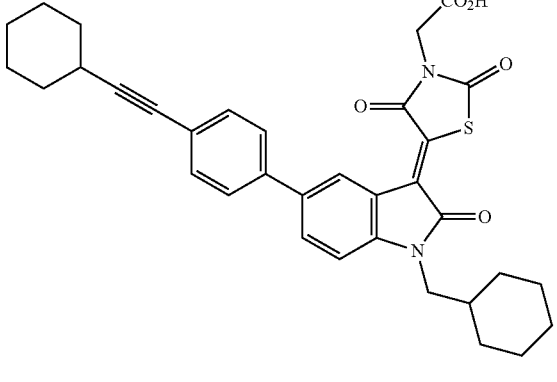 | 25 ± 5 | 685 ± 406 |
| II-23 | 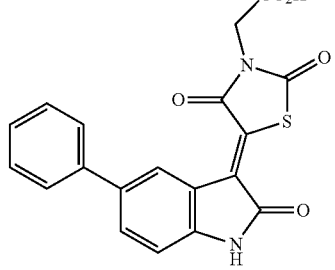 | 8023 ± 1050 | n.d. (63) |

TABLE 2-continued

| Compound | Structure | IC$_{50}$$^a$ against mPGES-1 (nM) | |
| --- | --- | --- | --- |
| | | Human enzyme | Mouse enzyme |
| II-24 | 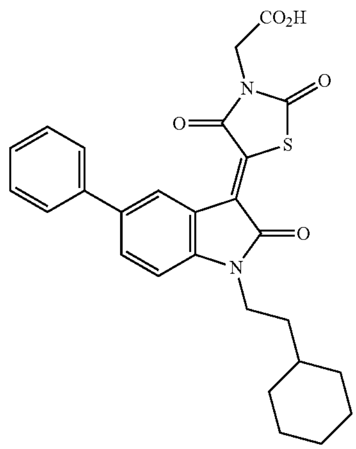 [SMILES: O=C(O)CN1C(=O)S/C(=C2\C(=O)N(CCC3CCCCC3)c3ccc(-c4ccccc4)cc32)C1=O] | 32 ± 6 | 777 ± 364 |
| II-25 | 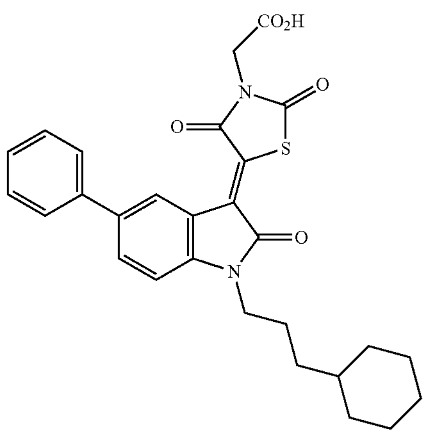 [SMILES: O=C(O)CN1C(=O)S/C(=C2\C(=O)N(CCCC3CCCCC3)c3ccc(-c4ccccc4)cc32)C1=O] | 16 ± 4 | 1222 ± 430 |
| II-26 | 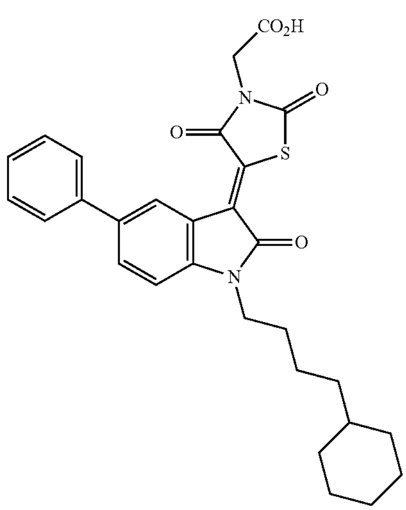 [SMILES: O=C(O)CN1C(=O)S/C(=C2\C(=O)N(CCCCC3CCCCC3)c3ccc(-c4ccccc4)cc32)C1=O] | 13 ± 3 | 1130 ± 244 |

TABLE 2-continued

| Compound | Structure | IC$_{50}$$^a$ against mPGES-1 (nM) | |
|---|---|---|---|
| | | Human enzyme | Mouse enzyme |
| II-27 | 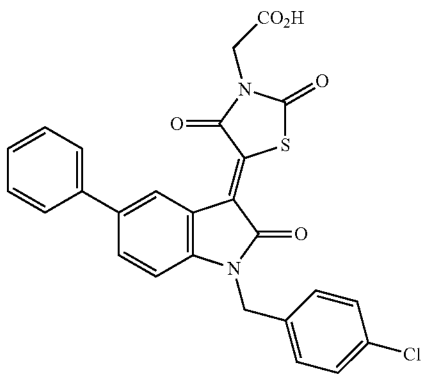 [SMILES: O=C(O)CN1C(=O)S/C(=C2\C(=O)N(Cc3ccc(Cl)cc3)c3ccc(-c4ccccc4)cc32)C1=O] | 54 ± 14 | 13236 ± 5081 |
| II-28 | 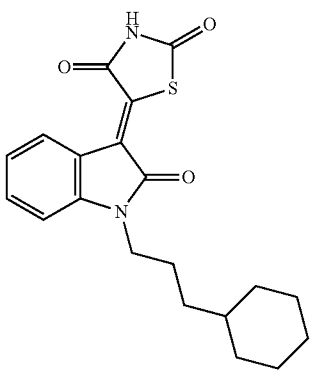 | 1393 ± 273 | n.d. (0) |
| II-29 | 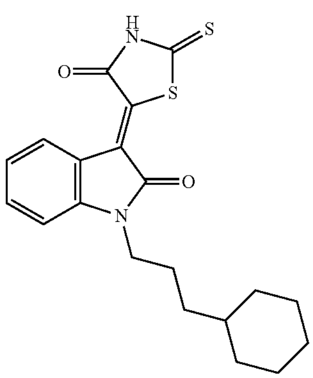 [SMILES: O=C1NC(=S)S/C1=C1\C(=O)N(CCCC2CCCCC2)c2ccccc21] | 1263 ± 335 | n.d. (29) |
| II-30 | 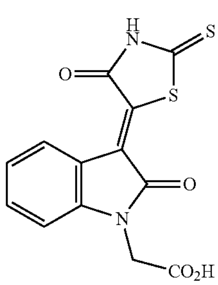 [SMILES: O=C(O)CN1C(=O)/C(=C2\SC(=S)NC2=O)c2ccccc21] | 211 ± 67 | n.d. (6.1) |

TABLE 2-continued

| Compound | Structure | IC$_{50}$[a] against mPGES-1 (nM) | |
|---|---|---|---|
| | | Human enzyme | Mouse enzyme |
| II-31 | 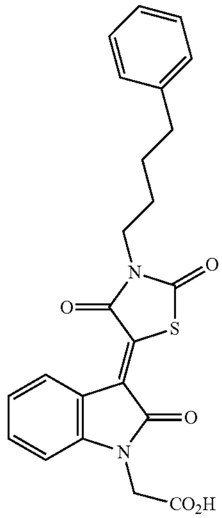 [SMILES: O=C(O)CN1C(=O)/C(=C2\SC(=O)N(CCCCc3ccccc3)C2=O)c2ccccc21] | 962 ± 159 | n.d. (64) |
| II-32 | 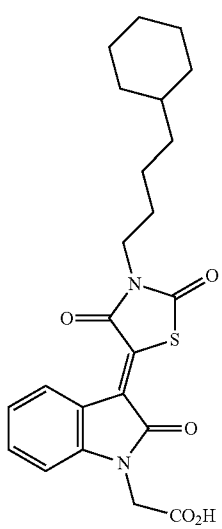 [SMILES: O=C(O)CN1C(=O)/C(=C2\SC(=O)N(CCCCC3CCCCC3)C2=O)c2ccccc21] | 2560 ± 442 | n.d. (44) |

[a]Data are expressed as means ± SD of single determinations obtained in triplicate.

[b]n.d. = not detected.

[c]The % inhibition of the compound at a concentration of 10 μM against mPGES-1 (IC$_{50}$ values were determined if the compounds resulted in 70% or higher inhibition).

Example 9 Characterization of Inhibition of Compounds of Formulae III and IV

TABLE 3

| Compound | Structure | IC$_{50}^a$ against mPGES-1 (nM) | |
| --- | --- | --- | --- |
| | | Human enzyme | Mouse enzyme |
| III-01 | 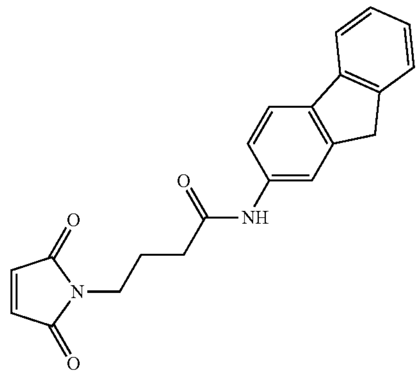 [SMILES: O=C(CCCN1C(=O)C=CC1=O)Nc1ccc2c(c1)Cc1ccccc1-2] | 1920 ± 300 | n.d. (48) |
| III-02 | 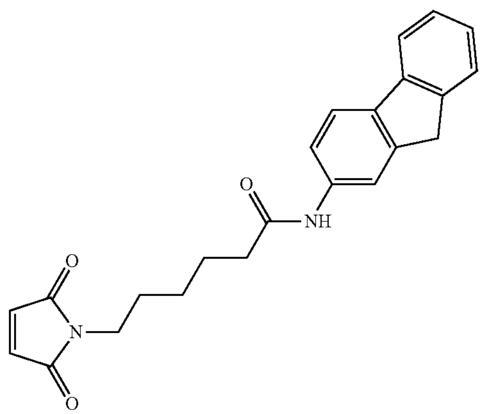 [SMILES: O=C(CCCCCN1C(=O)C=CC1=O)Nc1ccc2c(c1)Cc1ccccc1-2] | 613 ± 103 | 2880 ± 496 |
| III-03 | 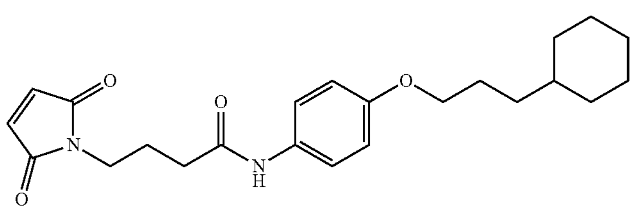 [SMILES: O=C(CCCN1C(=O)C=CC1=O)Nc1ccc(OCCCC2CCCCC2)cc1] | n.d.$^b$ (63)$^c$ | n.d. (55) |
| IV-01 | 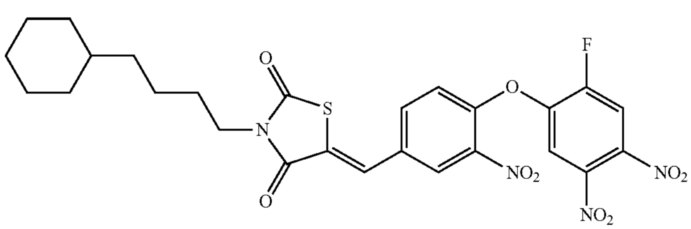 [SMILES: O=C1S/C(=C\c2ccc(Oc3cc([N+](=O)[O-])c([N+](=O)[O-])cc3F)c([N+](=O)[O-])c2)C(=O)N1CCCCC1CCCCC1] | 296 ± 48 | n.d. (91) |

$^a$Data are expressed as means ± SD of single determinations obtained in triplicate.

$^b$n.d. = not detected.

$^c$The % inhibition of the compound at a concentration of 10 μM against mPGES-1 (IC$_{50}$ values were determined if the compounds resulted in 70% or higher inhibition).

Example 10 Characterization of Inhibition of Compounds of Formula V
TABLE 4
| ID. | Structure | IC$_{50}$[a] against mPGES-1 (nM) | |
| --- | --- | --- | --- |
| | | Human enzyme | Mouse enzyme |
| V-01 | 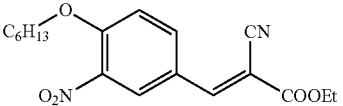 | 8739 ± 1169 | n.d.[b] |
| V-02 | 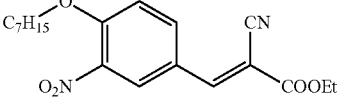 | 4817 ± 511 | n.d. |
| V-03 | 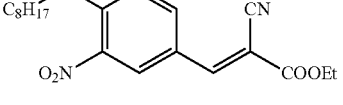 | 4749 ± 489 | n.d. |
| V-04 | 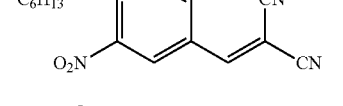 | 285 ± 40 | 754 ± 73 |
| V-05 | 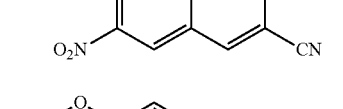 | 135 ± 16 | 776 ± 217 |
| V-06 | 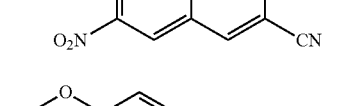 | 89 ± 12 | 716 ± 120 |
| V-07 | 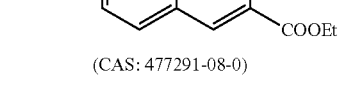<br>(CAS: 477291-08-0) | 6225 ± 502 | n.d. |
| V-08 | 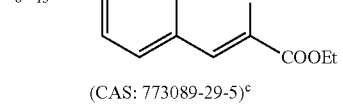<br>(CAS: 773089-29-5)[c] | 5241 ± 429 | n.d. |
| V-09 | 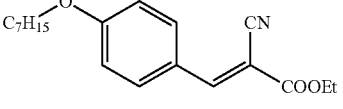<br>(CAS: 773089-30-8) | 3518 ± 471 | n.d. |
| V-10 | 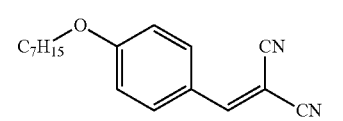<br>(CAS: 340217-23-4) | 136 ± 13 | 1390 ± 255 |

TABLE 4-continued

| ID. | Structure | IC$_{50}$$^a$ against mPGES-1 (nM) | |
|---|---|---|---|
| | | Human enzyme | Mouse enzyme |
| V-11 | C$_7$H$_{15}$O-C$_6$H$_4$-CH=C(CN)CONH$_2$ | 376 ± 31 | n.d. |
| V-12 | 3-Br-4-OC$_6$H$_{13}$-5-OMe-C$_6$H$_2$-CH=C(CN)COOEt | 998 ± 196 | n.d. |
| V-13 | 3-Br-4-OC$_6$H$_{13}$-5-OMe-C$_6$H$_2$-CH=C(CN)$_2$ | 181 ± 33 | 1632 ± 250 |
| V-14 | 3-Br-4-OC$_7$H$_{15}$-5-OMe-C$_6$H$_2$-CH=C(CN)COOEt | 1008 ± 262 | n.d. |
| V-15 | 3-Br-4-OC$_7$H$_{15}$-5-OMe-C$_6$H$_2$-CH=C(CN)$_2$ | 83 ± 14 | 357 ± 52 |
| V-16 | 3-Br-4-OC$_7$H$_{15}$-5-OMe-C$_6$H$_2$-CH=C(CN)CONH$_2$ | 1297 ± 232 | n.d. |
| V-17 | 3-Br-4-OC$_8$H$_{17}$-5-OMe-C$_6$H$_2$-CH=C(CN)COOEt | 1865 ± 350 | n.d. |
| V-18 | 3-Br-4-OC$_8$H$_{17}$-5-OMe-C$_6$H$_2$-CH=C(CN)$_2$ | 74 ± 8 | 572 ± 83 |
| V-19 | 3-OMe-4-OC$_{18}$H$_{37}$-5-Br-C$_6$H$_2$-CH=C(CN)COOEt | 2270 ± 350 | n.d. |

TABLE 4-continued

| ID. | Structure | IC$_{50}$$^a$ against mPGES-1 (nM) | |
|---|---|---|---|
| | | Human enzyme | Mouse enzyme |
| V-20 | (structure with C$_{18}$H$_{37}$O, OMe, Br, CH=C(CN)$_2$) | 50 ± 9 | 270 ± 64 |
| V-21 | (structure with C$_4$H$_9$O, OMe, CH=C(CN)COOEt) (CAS: 894215-85-1) | 5633 ± 987 | n.d. |
| V-22 | (structure with C$_4$H$_9$O, OMe, CH=C(CN)$_2$) (CAS: 891049-55-1) | 348 ± 100 | 1771 ± 241 |
| V-23 | (structure with C$_6$H$_{13}$O, OMe, CH=C(CN)COOEt) (CAS: 303119-03-1) | 1448 ± 192 | n.d. |
| V-24 | (structure with C$_6$H$_{13}$O, OMe, CH=C(CN)$_2$) (CAS: 939554-26-4) | 294 ± 60 | n.d. |
| V-25 | (structure with C$_6$H$_{13}$O, OMe, CH=C(CN)COOH) | 242 ± 30 | n.d. |
| V-26 | (structure with C$_{10}$H$_{21}$O, OMe, CH=C(CN)COOEt) | 905 ± 177 | n.d. |
| V-27 | (structure with C$_{10}$H$_{21}$O, OMe, CH=C(CN)COOH) | 51 ± 10 | 390 ± 84 |

TABLE 4-continued
| ID. | Structure | IC$_{50}$[a] against mPGES-1 (nM) | |
| --- | --- | --- | --- |
| | | Human enzyme | Mouse enzyme |
| V-28 | 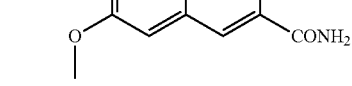 | 4374 ± 915 | n.d. |
| V-29 | 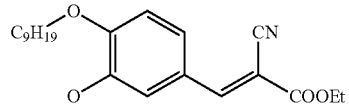 | 2880 ± 687 | n.d. |
| V-30 | 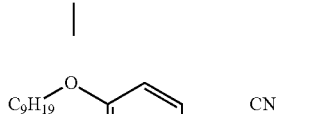 | 1095 ± 212 | n.d. |
| V-31 | 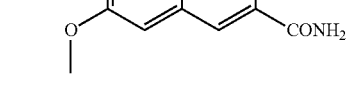 | 356 ± 123 | n.d. |
| V-32 | 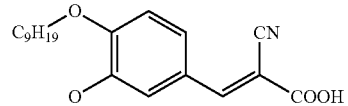 | 4283 ± 1404 | n.d. |
| V-33 | 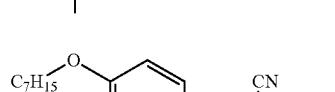 | 2210 ± 450 | n.d. |
| V-34 | 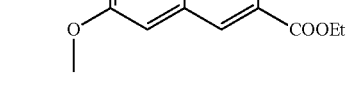 | 531 ± 116 | n.d. |
| V-35 | 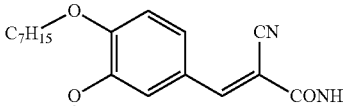 | 256 ± 33 | 7291 ± 2546 |
| V-36 | 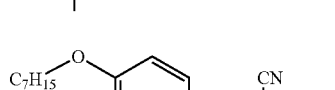<br>(CAS: 938114-32-0) | 541 ± 82 | n.d. |

TABLE 4-continued

| ID. | Structure | IC$_{50}$$^a$ against mPGES-1 (nM) | |
|---|---|---|---|
| | | Human enzyme | Mouse enzyme |
| V-37 | (CAS: 463974-33-6) | 5414 ± 818 | n.d. |
| V-38 | 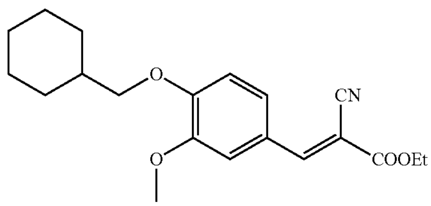 [SMILES: CCOC(=O)/C(C#N)=C/c1ccc(OCC2CCCCC2)c(OC)c1] | 10811 ± 1038 | n.d. |
| V-39 | 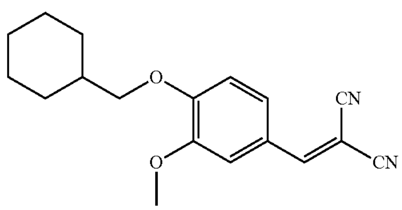 [SMILES: COc1cc(C=C(C#N)C#N)ccc1OCC1CCCCC1] | 1451 ± 152 | n.d. |
| V-40 | (CAS: 152086-78-7) | 1455 ± 119 | n.d. |
| V-41 | (CAS: 891085-65-7) | 4140 ± 858 | n.d. |
| V-42 | (CAS: 891047-19-1) | 439 ± 104 | n.d. |
| V-43 | 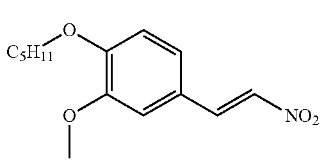 | 2772 ± 577 | n.d. |

TABLE 4-continued

| ID. | Structure | IC$_{50}^{a}$ against mPGES-1 (nM) | |
|---|---|---|---|
| | | Human enzyme | Mouse enzyme |
| V-44 | 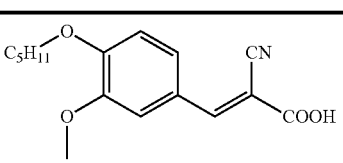 (CAS: 938340-36-4) | 456 ± 42 | n.d. |

[a]Data are expressed as means ± SD of single determinations obtained in triplicate.
[b]n.d. = not detected.
[c]Known compounds were labeled with CAS Example 11 Characterization of Inhibition of Compounds of Formulae VI and VII

TABLE 5

| Name | Structure | IC$_{50}^{a}$ against mPGES-1 (nM) | |
|---|---|---|---|
| | | Human | Mouse |
| VI-01 | 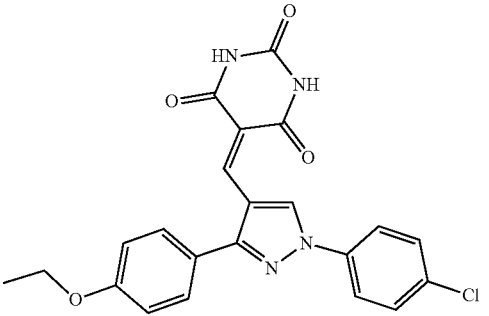 | 265 ± 96 | n.d.[b] (28)[c] |
| VI-02 | 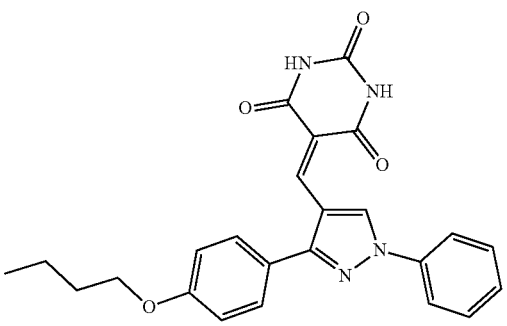 | 212 ± 34 | 2573 ± 628 |
| VI-03 | 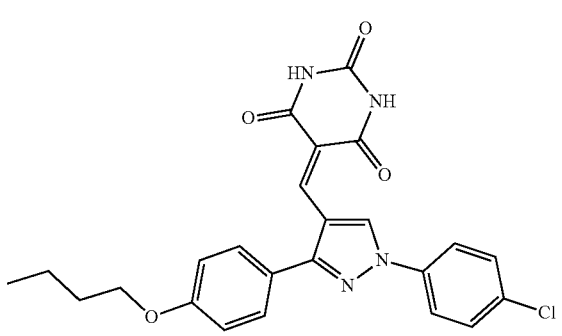 [SMILES: CCCCOc1ccc(-c2nn(-c3ccc(Cl)cc3)cc2C=C2C(=O)NC(=O)NC2=O)cc1] | 169 ± 41 | 357 ± 75 |

TABLE 5-continued

| Name | Structure | IC$_{50}$$^a$ against mPGES-1 (nM) | |
| --- | --- | --- | --- |
| | | Human | Mouse |
| VI-04 | 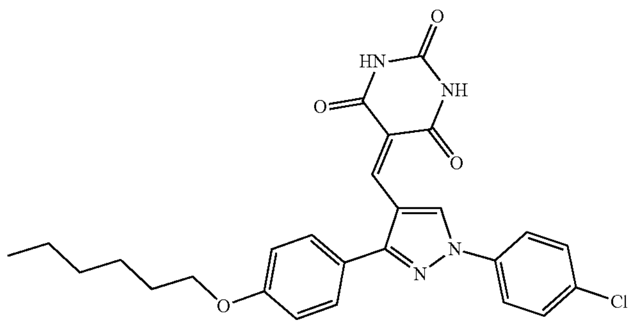 [SMILES: CCCCCCOc1ccc(-c2nn(-c3ccc(Cl)cc3)cc2C=C2C(=O)NC(=O)NC2=O)cc1] | 285 ± 65 | n.d. (46) |
| VI-05 | 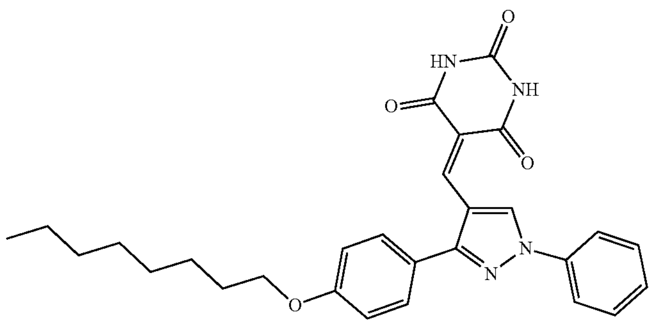 | 323 ± 52 | 2157 ± 188 |
| VI-06 | 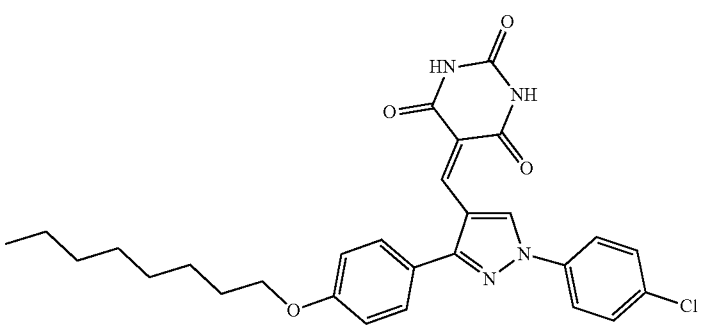 [SMILES: CCCCCCCCOc1ccc(-c2nn(-c3ccc(Cl)cc3)cc2C=C2C(=O)NC(=O)NC2=O)cc1] | 361 ± 51 | 740 ± 108 |
| VI-07 | 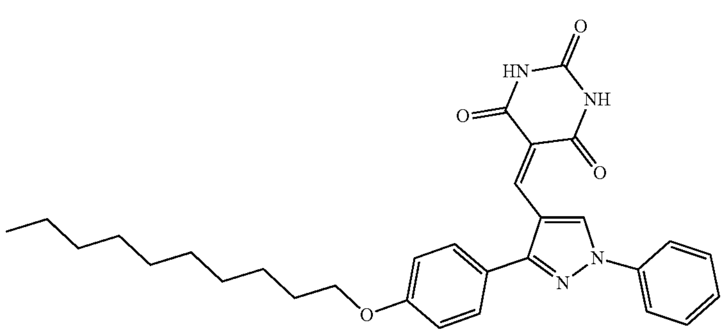 [SMILES: CCCCCCCCCCOc1ccc(-c2nn(-c3ccccc3)cc2C=C2C(=O)NC(=O)NC2=O)cc1] | 375 ± 127 | n.d. (21) |

TABLE 5-continued
| | | IC$_{50}{}^a$ against mPGES-1 (nM) | |
|---|---|---|---|
| Name | Structure | Human | Mouse |
| VI-08 | 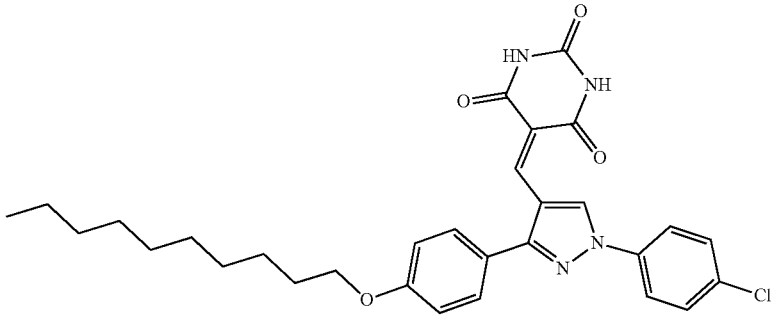 [SMILES: CCCCCCCCCCOc1ccc(-c2nn(-c3ccc(Cl)cc3)cc2C=C2C(=O)NC(=O)NC2=O)cc1] | 294 ± 83 | n.d. (24) |
| VI-09 | 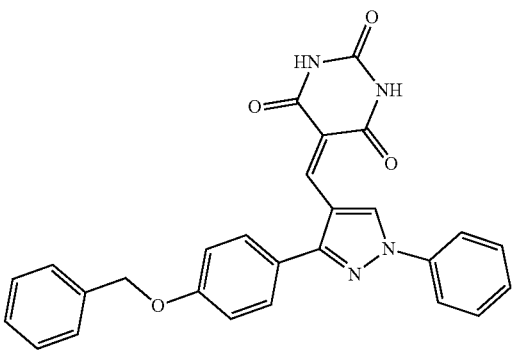 [SMILES: O=C1NC(=O)C(=Cc2cn(-c3ccccc3)nc2-c2ccc(OCc3ccccc3)cc2)C(=O)N1] | 598 ± 142 | n.d. (0) |
| VI-10 | 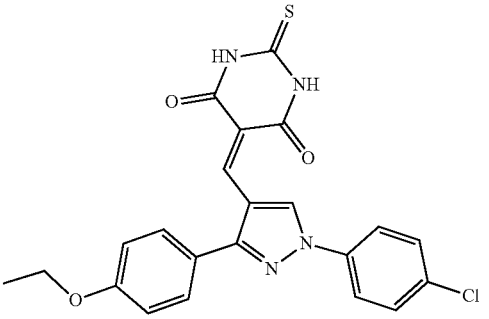 [SMILES: CCOc1ccc(-c2nn(-c3ccc(Cl)cc3)cc2C=C2C(=O)NC(=S)NC2=O)cc1] | 95 ± 16 | n.d. (46) |
| VI-11 | 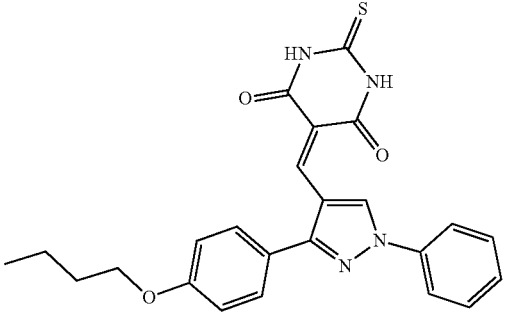 [SMILES: CCCCOc1ccc(-c2nn(-c3ccccc3)cc2C=C2C(=O)NC(=S)NC2=O)cc1] | 92 ± 20 | 1264 ± 138 |

TABLE 5-continued
| Name | Structure | IC$_{50}^{a}$ against mPGES-1 (nM) | |
|---|---|---|---|
| | | Human | Mouse |
| VI-12 | 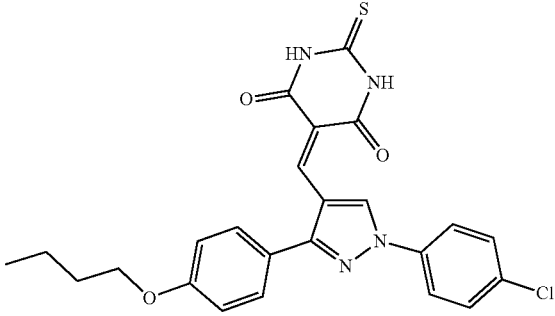 [SMILES: CCCCOc1ccc(-c2nn(-c3ccc(Cl)cc3)cc2C=C2C(=O)NC(=S)NC2=O)cc1] | 56 ± 10 | 445 ± 83 |
| VI-13 | 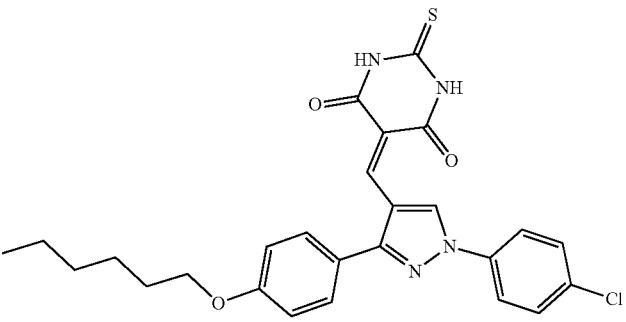 [SMILES: CCCCCCOc1ccc(-c2nn(-c3ccc(Cl)cc3)cc2C=C2C(=O)NC(=S)NC2=O)cc1] | 52 ± 15 | 1769 ± 1158 |
| VI-14 | 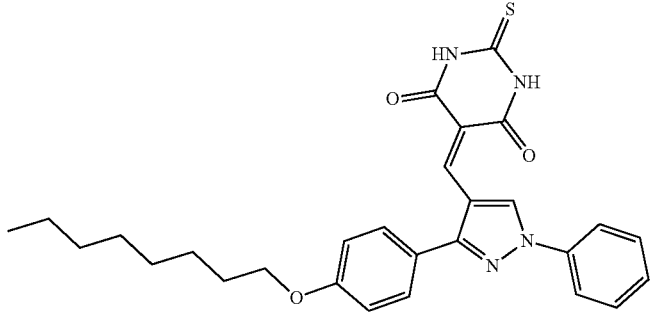 | 113 ± 23 | 1126 ± 131 |
| VI-15 | 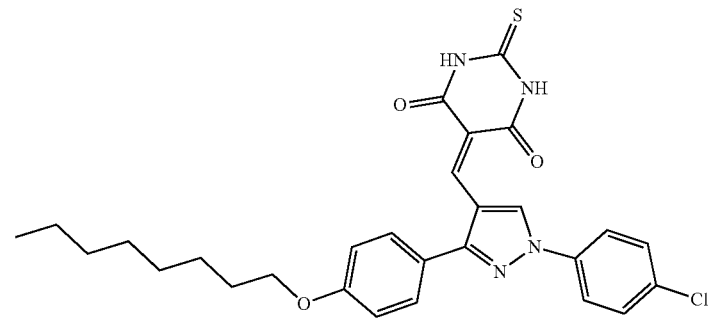 | 92 ± 19 | 316 ± 30 |

TABLE 5-continued

| Name | Structure | IC$_{50}$$^a$ against mPGES-1 (nM) | |
| --- | --- | --- | --- |
| | | Human | Mouse |
| VI-16 | 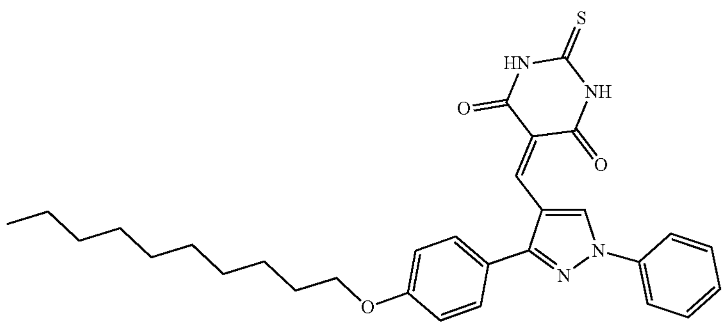 [SMILES: CCCCCCCCCCOc1ccc(-c2nn(-c3ccccc3)cc2C=C2C(=O)NC(=S)NC2=O)cc1] | 188 ± 31 | n.d. (50) |
| VI-17 | 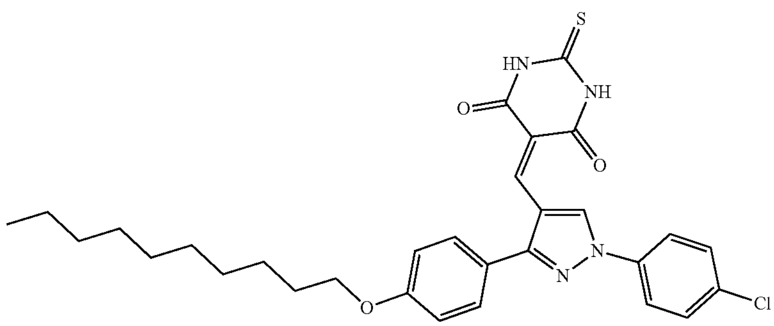 | 93 ± 14 | n.d. (56) |
| VI-18 | 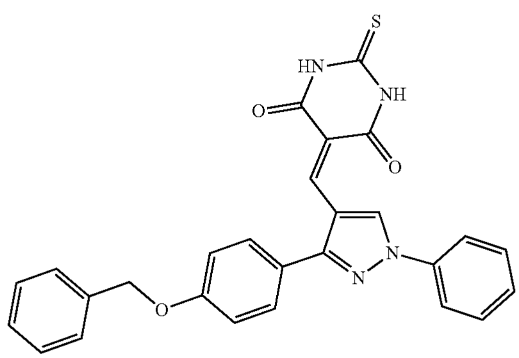 [SMILES: O=C1NC(=S)NC(=O)C1=Cc1cn(-c2ccccc2)nc1-c1ccc(OCc2ccccc2)cc1] | 797 ± 160 | n.d. (25) |
| VI-19 | 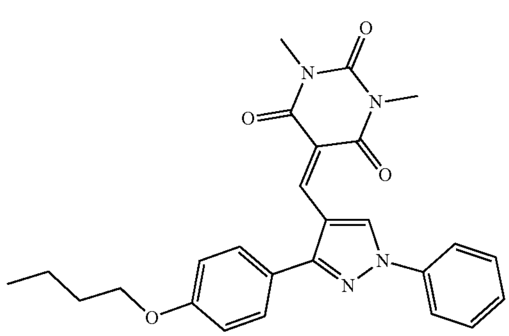 [SMILES: CCCCOc1ccc(-c2nn(-c3ccccc3)cc2C=C2C(=O)N(C)C(=O)N(C)C2=O)cc1] | n.d. (30) | n.d. |

TABLE 5-continued
| Name | Structure | IC$_{50}$$^a$ against mPGES-1 (nM) | |
| --- | --- | --- | --- |
| | | Human | Mouse |
| VI-20 | 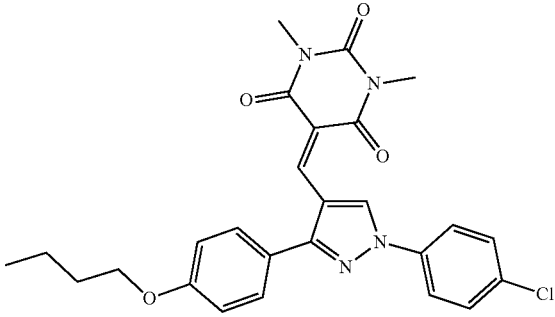 [SMILES: CCCCOc1ccc(-c2nn(-c3ccc(Cl)cc3)cc2C=C2C(=O)N(C)C(=O)N(C)C2=O)cc1] | n.d. (29) | n.d. |
| VI-21 | 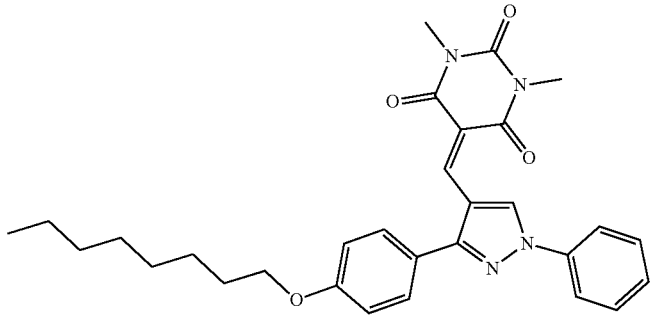 [SMILES: CCCCCCCCOc1ccc(-c2nn(-c3ccccc3)cc2C=C2C(=O)N(C)C(=O)N(C)C2=O)cc1] | n.d. (16) | n.d. |
| VI-22 | 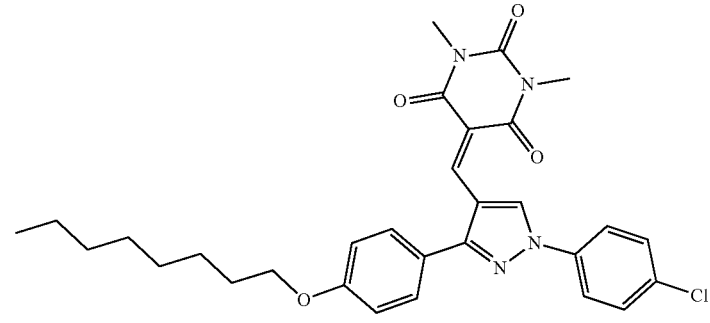 [SMILES: CCCCCCCCOc1ccc(-c2nn(-c3ccc(Cl)cc3)cc2C=C2C(=O)N(C)C(=O)N(C)C2=O)cc1] | n.d. (6.8) | n.d. |
| VI-23 | 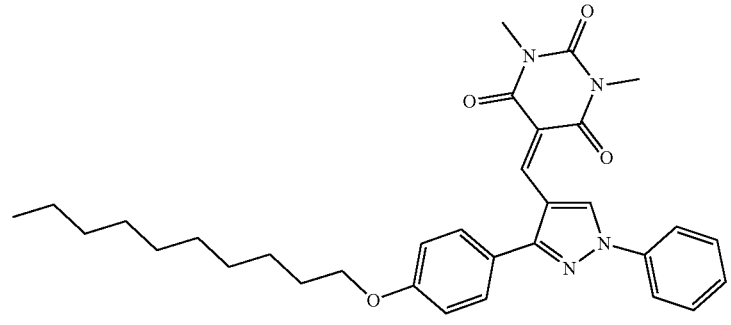 [SMILES: CCCCCCCCCCOc1ccc(-c2nn(-c3ccccc3)cc2C=C2C(=O)N(C)C(=O)N(C)C2=O)cc1] | n.d. (0) | n.d. |

TABLE 5-continued
| Name | Structure | IC$_{50}$$^a$ against mPGES-1 (nM) | |
|---|---|---|---|
| | | Human | Mouse |
| VI-24 | 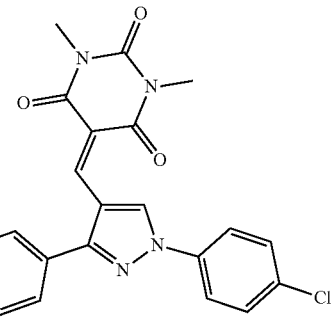 | n.d. (0) | n.d. |
| VII-01 | 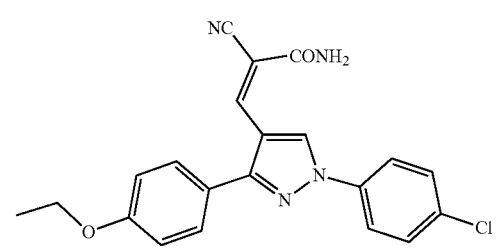 [SMILES: CCOc1ccc(-c2nn(-c3ccc(Cl)cc3)cc2/C=C(/C#N)C(N)=O)cc1] | n.d. (32) | n.d. |
| VII-02 | 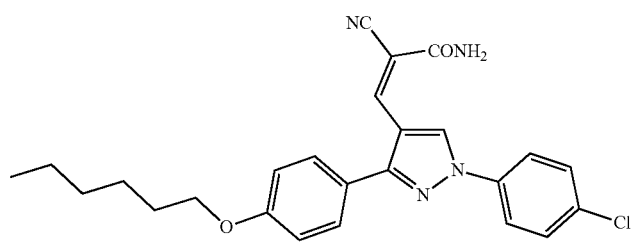 [SMILES: CCCCCCOc1ccc(-c2nn(-c3ccc(Cl)cc3)cc2/C=C(/C#N)C(N)=O)cc1] | n.d. (14) | n.d. |
| VII-03 | 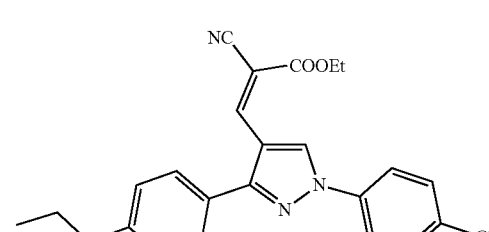 | n.d. (24) | n.d. |
| VII-04 | 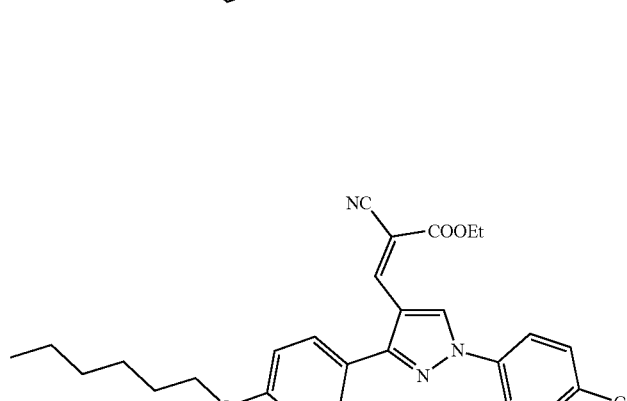 | n.d. (37) | n.d. |

TABLE 5-continued

| Name | Structure | IC$_{50}$$^a$ against mPGES-1 (nM) | |
| --- | --- | --- | --- |
| | | Human | Mouse |
| VII-05 | 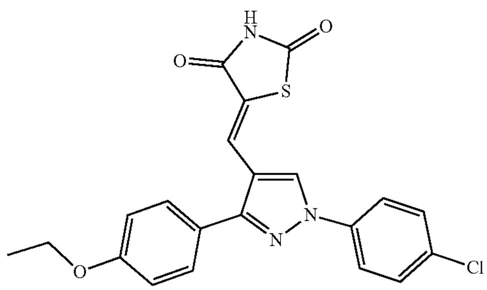 [SMILES: CCOc1ccc(-c2nn(-c3ccc(Cl)cc3)cc2/C=C2\SC(=O)NC2=O)cc1] | 1593 ± 557 | n.d. |
| VII-06 | 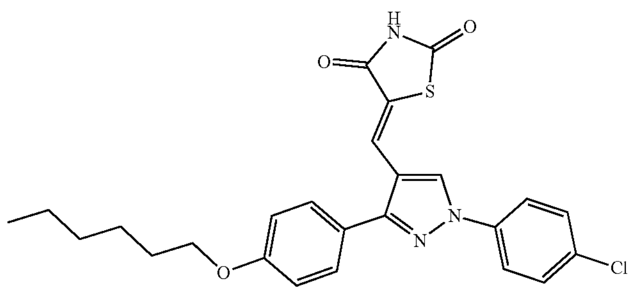 | 1394 ± 303 | n.d. |
| VII-07 | 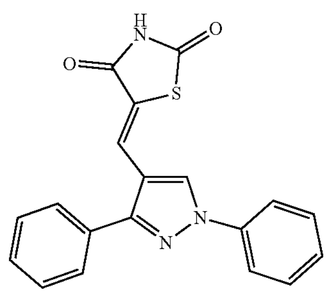 [SMILES: O=C1NC(=O)/C(=C/c2cn(-c3ccccc3)nc2-c2ccccc2)S1] | 4932 ± 1161 | n.d. |
| VII-08 | 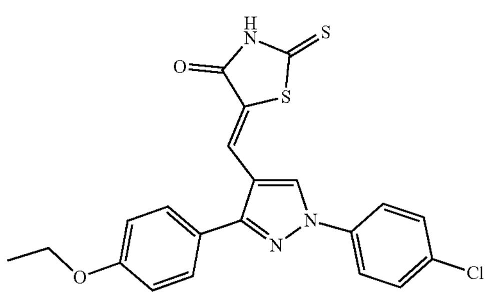 | 1036 ± 293 | n.d. |
| VII-09 | 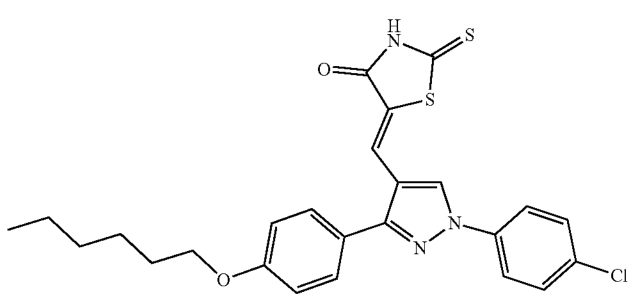 [SMILES: CCCCCCOc1ccc(-c2nn(-c3ccc(Cl)cc3)cc2/C=C2\SC(=S)NC2=O)cc1] | 1729 ± 666 | n.d. |

TABLE 5-continued
| Name | Structure | IC$_{50}{}^a$ against mPGES-1 (nM) Human | Mouse |
|---|---|---|---|
| VII-10 | 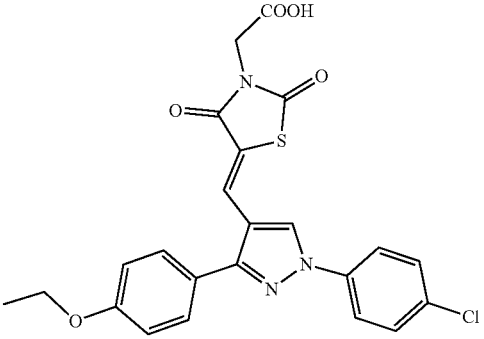 [SMILES: CCOc1ccc(-c2nn(-c3ccc(Cl)cc3)cc2/C=C2\SC(=O)N(CC(=O)O)C2=O)cc1] | 41 ± 5 | n.d. (35) |
| VII-11 | 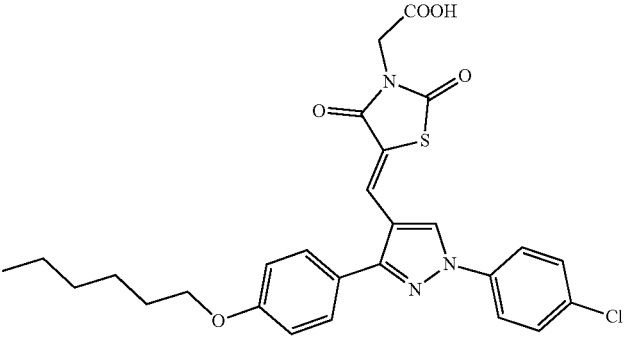 [SMILES: CCCCCCOc1ccc(-c2nn(-c3ccc(Cl)cc3)cc2/C=C2\SC(=O)N(CC(=O)O)C2=O)cc1] | 36 ± 11 | n.d. (37) |
| VII-12 | 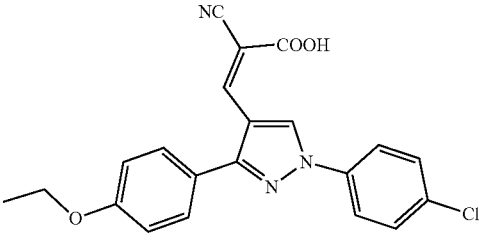 [SMILES: CCOc1ccc(-c2nn(-c3ccc(Cl)cc3)cc2/C=C(/C#N)C(=O)O)cc1] | 282 ± 83 | n.d. (12) |
| VII-13 | 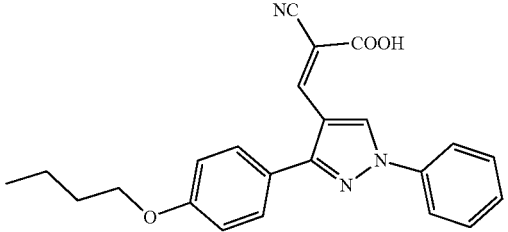 [SMILES: CCCCOc1ccc(-c2nn(-c3ccccc3)cc2/C=C(/C#N)C(=O)O)cc1] | 296 ± 68 | n.d. (21) |
| VII-14 | 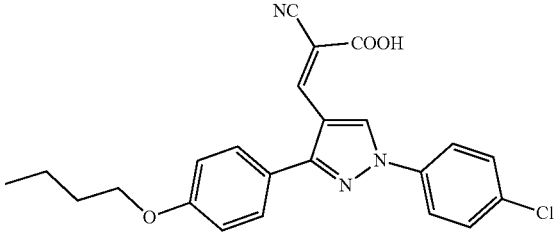 | 190 ± 68 | n.d. (30) |

TABLE 5-continued

| Name | Structure | IC$_{50}$$^a$ against mPGES-1 (nM) | |
|---|---|---|---|
| | | Human | Mouse |
| VII-15 | 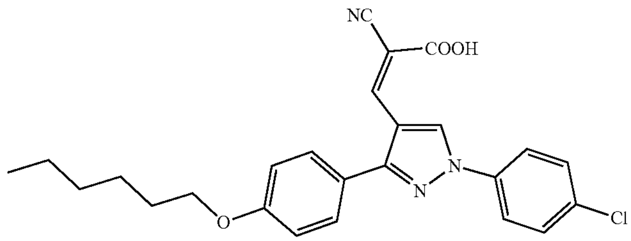 [SMILES: CCCCCCOc1ccc(-c2nn(-c3ccc(Cl)cc3)cc2/C=C(/C#N)C(=O)O)cc1] | 83 ± 30 | n.d. (48) |
| VII-16 | 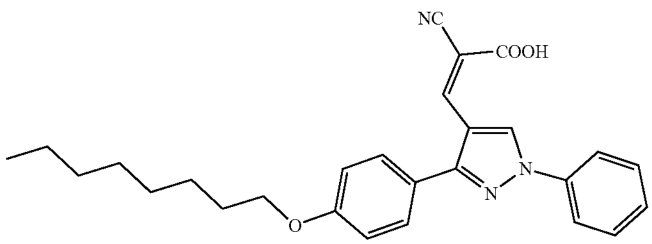 [SMILES: CCCCCCCCOc1ccc(-c2nn(-c3ccccc3)cc2/C=C(/C#N)C(=O)O)cc1] | 209 ± 42 | n.d. (46) |
| VII-17 | 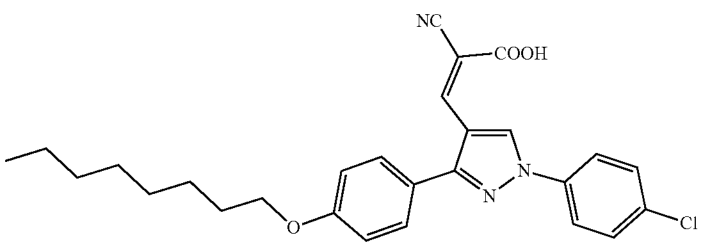 [SMILES: CCCCCCCCOc1ccc(-c2nn(-c3ccc(Cl)cc3)cc2/C=C(/C#N)C(=O)O)cc1] | 90 ± 15 | n.d. (29) |
| VII-18 | 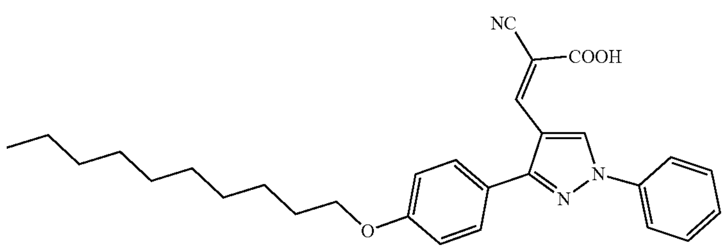 [SMILES: CCCCCCCCCCOc1ccc(-c2nn(-c3ccccc3)cc2/C=C(/C#N)C(=O)O)cc1] | 197 ± 32 | n.d. (4.3) |
| VII-19 | 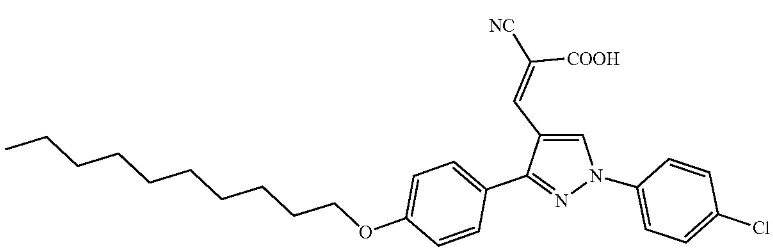 [SMILES: CCCCCCCCCCOc1ccc(-c2nn(-c3ccc(Cl)cc3)cc2/C=C(/C#N)C(=O)O)cc1] | 97 ± 15 | n.d. (4.6) |
| VII-20 | 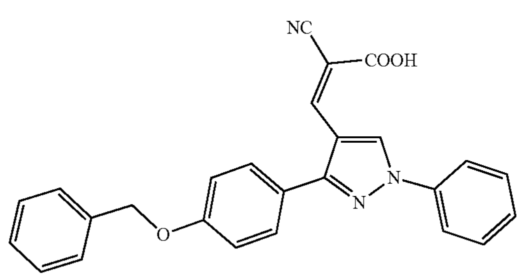 [SMILES: N#C/C(=C/c1cn(-c2ccccc2)nc1-c1ccc(OCc2ccccc2)cc1)C(=O)O] | 806 ± 162 | n.d. (16) |

TABLE 5-continued

| Name | Structure | IC$_{50}$$^a$ against mPGES-1 (nM) | |
|---|---|---|---|
| | | Human | Mouse |
| VII-21 | 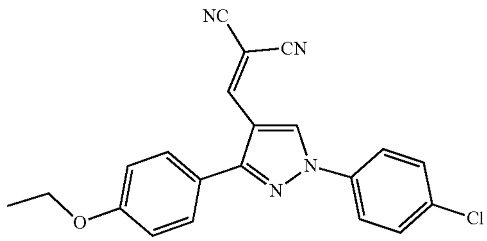 [SMILES: CCOc1ccc(-c2nn(-c3ccc(Cl)cc3)cc2C=C(C#N)C#N)cc1] | n.d. (51) | n.d. |
| VII-22 | 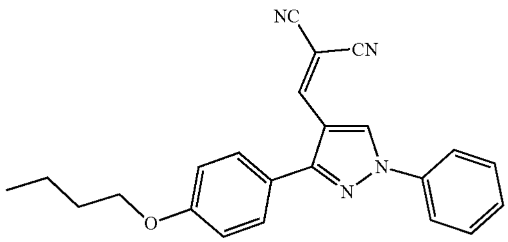 [SMILES: CCCCOc1ccc(-c2nn(-c3ccccc3)cc2C=C(C#N)C#N)cc1] | n.d. (54) | n.d. |
| VII-23 | 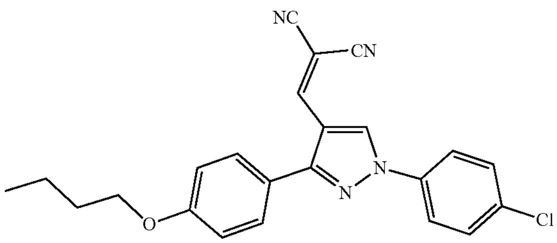 [SMILES: CCCCOc1ccc(-c2nn(-c3ccc(Cl)cc3)cc2C=C(C#N)C#N)cc1] | n.d. (77) | n.d. |
| VII-24 | 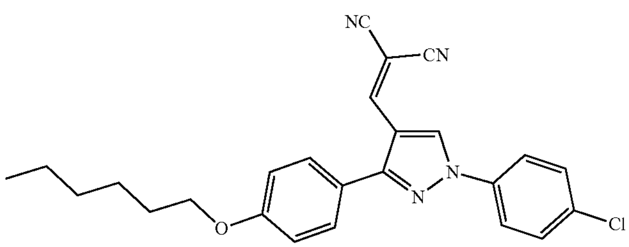 [SMILES: CCCCCCOc1ccc(-c2nn(-c3ccc(Cl)cc3)cc2C=C(C#N)C#N)cc1] | n.d. (64) | n.d. |
| VII-25 | 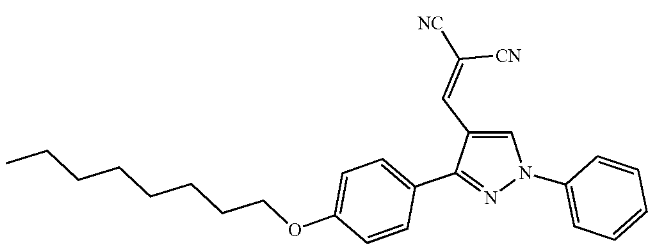 [SMILES: CCCCCCCCOc1ccc(-c2nn(-c3ccccc3)cc2C=C(C#N)C#N)cc1] | n.d. (55) | n.d. |
| VII-26 | 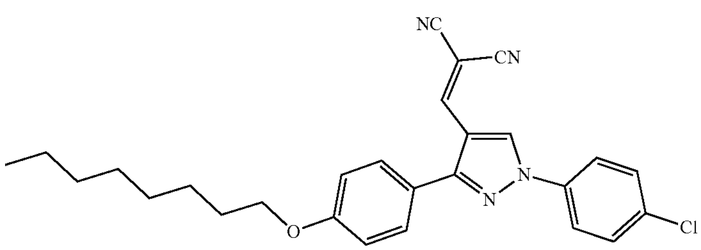 [SMILES: CCCCCCCCOc1ccc(-c2nn(-c3ccc(Cl)cc3)cc2C=C(C#N)C#N)cc1] | n.d. (52) | n.d. |

TABLE 5-continued

| Name | Structure | IC$_{50}^{a}$ against mPGES-1 (nM) | |
|---|---|---|---|
| | | Human | Mouse |
| VII-27 | 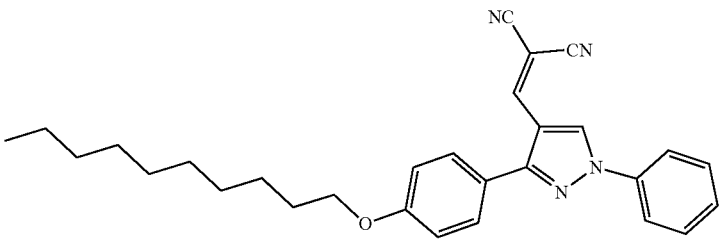 [SMILES: CCCCCCCCCCOc1ccc(-c2nn(-c3ccccc3)cc2C=C(C#N)C#N)cc1] | n.d. (49) | n.d. |
| VII-28 | 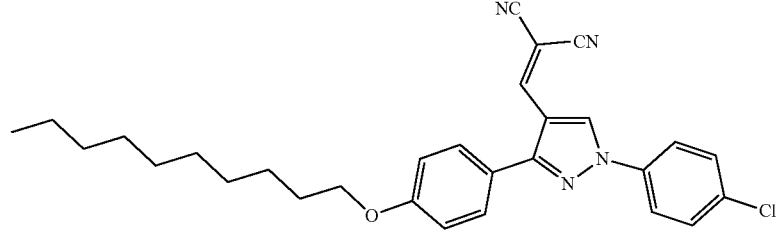 [SMILES: CCCCCCCCCCOc1ccc(-c2nn(-c3ccc(Cl)cc3)cc2C=C(C#N)C#N)cc1] | n.d. (47) | n.d. |

$^{a}$Data are expressed as means ± SD of single determinations obtained in triplicate.
$^{b}$n.d. = not detected.
$^{c}$The % inhibition of the compound at a concentration of 10 μM against mPGES-1.

While the terms used herein are believed to be well understood by one of ordinary skill in the art, the definitions set forth herein are provided to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "an inhibitor" includes a plurality of such inhibitors, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±50%, in some embodiments ±40%, in some embodiments ±30%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

Throughout this document, various references are mentioned. All such references, including those listed below, are incorporated herein by reference.

REFERENCES

1. Serhan, C. N.; Levy, B. *Proc. Natl. Acad. Sci. U.S.A* 2003, 100, 8609.
2. Kudo, I.; Murakami, M. *J Biochem. Mol. Biol.* 2005, 38, 633.
3. Fahmi, H. *Current Opinion in Rheumatology* 2004, 16, 623.
4. Park, J. Y; Pillinger, M. H.; Abramson, S. B. *Clinical Immunology* 2006, 119, 229.
5. Murakami, M.; Nakatani, Y; Tanioka, T.; Kudo, I. *Prostaglandins Other Lipid Mediators* 2002, 68-9, 383.
6. Murakami, M.; Naraba, H.; Tanioka, T.; Semmyo, N.; Nakatani, Y; Kojima, F.; Ikeda, T.; Fueki, M.; Ueno, A.; Oh-ishi, S.; Kudo, I. *J. Biol. Chem.* 2000, 275, 32783.
7. Uematsu, S.; Matsumoto, M.; Takeda, K.; Akira, S. *Journal of Immunology* 2002, 168, 5811.
8. Kamei, D.; Murakami, M.; Nakatani, Y; Ishikawa, Y; Ishii, T.; Kudo, I. *Journal of Biological Chemistry* 2003, 278, 19396.
9. Kamei, D.; Yamakawa, K.; Takegoshi, Y; Mikami-Nakanishi, M.; Nakatani, Y; Oh-ishi, S.; Yasui, H.; Azuma, Y; Hirasawa, N.; Ohuchi, K.; Kawaguchi, H.; Ishikawa, Y; Ishii, T.; Uematsu, S.; Akira, S.; Murakami, M.; Kudo, I *Journal of Biological Chemistry* 2004, 279, 33684.

10. Ikeda-Matsuo, Y; Ota, A.; Fukada, T.; Uematsu, S.; Akira, S.; Sasaki, Y *Proceedings of the National Academy of Sciences of the United States of America* 2006, 103, 11790.
11. Murakami, M.; Kudo, I. *Progress in Lipid Research* 2004, 43, 3.
12. Claveau, D.; Sirinyan, M.; Guay, J.; Gordon, R.; Chan, C. C.; Bureau, Y; Riendeau, D.; Mancini, J. A. *Journal of Immunology* 2003, 170, 4738.
13. Oshima, H.; Oshima, M.; Inaba, K.; Taketo, M. M. *EMBO Journal* 2004, 23, 1669.
14. Friesen, R. W.; Mancini, J. A. *Journal of Medicinal Chemistry* 2008, 51, 4059.
15. Samuelsson, B.; Morgenstern, R.; Jakobsson, P. *J. Pharmacological Reviews* 2007, 59, 207.
16. Scholich, K.; Geisslinger, G. *Trends in Pharmacological Sciences* 2006, 27, 399.
17. Cheng, Y; Wang, M.; Yu, Y; Lawson, J.; Funk, C. D.; FitzGerald, G. A. *Journal of Clinical Investigation* 2006, 116, 1391.
18. Engblom, D.; Saha, S.; Engstrom, L.; Westman, M.; Audoly, L. P.; Jakobsson, P. J.; Blomqvist, A. *Nature Neuroscience* 2003, 6, 1137.
19. Trebino, C. E.; Stock, J. L.; Gibbons, C. P.; Naiman, B. M.; Wachtmann, T. S.; Umland, J. P.; Pandher, K.; Lapointe, J. M.; Saha, S.; Roach, M. L.; Carter, D.; Thomas, N. A.; Durtschi, B. A.; McNeish, J. D.; Hambor, J. E.; Jakobsson, P. J.; Carty, T. J.; Perez, J. R.; Audoly, L. P. *Proceedings of the National Academy of Sciences of the United States of America* 2003, 100, 9044.
20. Thoren, S.; Jakobsson, P. *J. Eur. J. Biochem.* 2000, 267, 6428.
21. Mancini, J. A.; Blood, K.; Guay, J.; Gordon, R.; Claveau, D.; Chan, C. C.; Riendeau, D. *J. Biol. Chem.* 2001, 276, 4469.
22. Riendeau, D.; Aspiotis, R.; Ethier, D.; Gareau, Y; Grimm, E. L.; Guay, J.; Guiral, S.; Juteau, H.; Mancini, J. A.; Methot, N.; Rubin, J.; Friesen, R. W. *Bioorg. Med Chem. Lett.* 2005, 15, 3352.
23. De Simone, R.; Chini, M. G.; Bruno, I.; Riccio, R.; Mueller, D.; Werz, O.; Bifulco, G. *Journal of Medicinal Chemistry* 2011, 54, 1565.
24. Quraishi, O.; Mancini, J. A.; Riendeau, D. *Biochem. Pharmacol.* 2002, 63, 1183.
25. Lu, J.; Wu, L.; Jiang, J.; Zhang, X., Helical Nanostructures of an Optically Active Metal-Free Porphyrin with Four Optically Active Binaphthyl Moieties: Effect of Metal-Ligand Coordination on the Morphology. *European Journal of Inorganic Chemistry* 2010, 2010 (25), 4000-4008.
26. Saari, W. S.; Schwering, J. E.; Lyle, P. A.; Smith, S. J.; Engelhardt, E. L., Cyclization-activated prodrugs. Basic carbamates of 4-hydroxyanisole. *Journal of medicinal chemistry* 1990, 33 (1), 97-101.
27. Baron, R.; Huang, C. H.; Bassani, D. M.; Onopriyenko, A.; Zayats, M.; Willner, I., Hydrogen-bonded CdS nanoparticle assemblies on electrodes for photoelectrochemical applications. *Angewandte Chemie* 2005, 44 (26), 4010-5.
28. Hidalgo-Figueroa, S.; Ramirez-Espinosa, J. J.; Estrada-Soto, S.; Almanza-Perez, J. C.; Roman-Ramos, R.; Alarcon-Aguilar, F. J.; Hernandez-Rosado, J. V.; Moreno-Diaz, H.; Diaz-Coutino, D.; Navarrete-Vazquez, G., Discovery of thiazolidine-2,4-dione/biphenylcarbonitrile hybrid as dual PPAR alpha/gamma modulator with antidiabetic effect: in vitro, in silico and in vivo approaches. *Chemical biology & drug design* 2013, 81 (4), 474-83.
29. Yan, Q.; Cao, R.; Yi, W.; Chen, Z.; Wen, H.; Ma, L.; Song, H., Inhibitory effects of 5-benzylidene barbiturate derivatives on mushroom tyrosinase and their antibacterial activities. *European journal of medicinal chemistry* 2009, 44 (10), 4235-43.
30. Komiya, M.; Asano, S.; Koike, N.; Koga, E.; Igarashi, J.; Nakatani, S.; Isobe, Y., Structure and activity relationship of 2-(substituted benzoyl)-hydroxyindoles as novel CaM-KII inhibitors. *Bioorganic & medicinal chemistry letters* 2011, 21 (5), 1456-8.
31. Chen, H.; Tsalkova, T.; Chepurny, O. G.; Mei, F. C.; Holz, G. G.; Cheng, X.; Zhou, J., Identification and characterization of small molecules as potent and specific EPAC2 antagonists. *Journal of medicinal chemistry* 2013, 56 (3), 952-62.
32. Murugan, R.; Anbazhagan, S.; Lingeshwaran; Sriman Narayanan, S., Synthesis and in vivo antidiabetic activity of novel dispiropyrrolidines through [3+2] cycloaddition reactions with thiazolidinedione and rhodanine derivatives. *European journal of medicinal chemistry* 2009, 44 (8), 3272-9.
33. Shibinskaya, M. O.; Lyakhov, S. A.; Mazepa, A. V.; Andronati, S. A.; Turov, A. V.; Zholobak, N. M.; Spivak, N. Y., Synthesis, cytotoxicity, antiviral activity and interferon inducing ability of 6-(2-aminoethyl)-6H-indolo[2,3-b]quinoxalines. *European journal of medicinal chemistry* 2010, 45 (3), 1237-43.
34. Yamamoto, Y.; Yohda, M.; Shirai, T.; Ito, H.; Miyaura, N., Me-BIPAM for the synthesis of optically active 3-aryl-3-hydroxy-2-oxindoles by ruthenium-catalyzed addition of arylboronic acids to isatins. *Chemistry, an Asian journal* 2012, 7 (10), 2446-9;
35. Kaila, N.; Janz, K.; Huang, A.; Moretto, A.; DeBernardo, S.; Bedard, P. W.; Tam, S.; Clerin, V.; Keith, J. C., Jr.; Tsao, D. H.; Sushkova, N.; Shaw, G. D.; Camphausen, R. T.; Schaub, R. G.; Wang, Q., 2-(4-Chlorobenzyl)-3-hydroxy-7,8,9,10-tetrahydrobenzo[H]quinoline-4-carboxylic acid (PSI-697): identification of a clinical candidate from the quinoline salicylic acid series of P-selectin antagonists. *Journal of medicinal chemistry* 2007, 50 (1), 40-64.
36. Yamazaki, K.; Kaneko, Y.; Suwa, K.; Ebara, S.; Nakazawa, K.; Yasuno, K., Synthesis of potent and selective inhibitors of Candida albicans N-myristoyltransferase based on the benzothiazole structure. *Bioorganic & medicinal chemistry* 2005, 13 (7), 2509-22.
37. Xie, J.; Seto, C. T., A two stage click-based library of protein tyrosine phosphatase inhibitors. *Bioorganic & medicinal chemistry* 2007, 15 (1), 458-73.
38. Cumpstey, I.; Carlsson, S.; Leffler, H.; Nilsson, U. J., Synthesis of a phenyl thio-beta-D-galactopyranoside library from 1,5-difluoro-2,4-dinitrobenzene: discovery of efficient and selective monosaccharide inhibitors of galectin-7. *Organic & biomolecular chemistry* 2005, 3 (10), 1922-32.
39. Shete, D. K., et al., *Comparative efficiency of metal phosphates as a protomer in multi-component condensation reaction.* Pharm. Lett., 2010. 2(3): p. 59-65.
40. de Vasconcelos, A., et al., *Antioxidant capacity and environmentally friendly synthesis of dihydro-(2H)-pyrimidinones promoted by naturally occurring organic acids.* J. Biochem. Mol. Toxicol., 2012. 26(4): p. 155-161.
41. Rathelot, P., et al., *1,3-Diphenylpyrazoles: synthesis and antiparasitic activities of azomethine derivatives.* European Journal of Medicinal Chemistry, 2002. 37(8): p. 671-679.

42. Stella, A., et al., *Synthesis of a 2,4,6-trisubstituted 5-cyano-pyrimidine library and evaluation of its immunosuppressive activity in a Mixed Lymphocyte Reaction assay.* Bioorg. Med. Chem., 2013. 21(5): p. 1209-1218.

What is claimed is:

1. A compound of the formula:

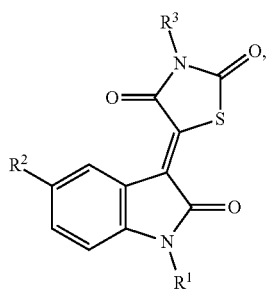

or pharmaceutically acceptable salts thereof,
wherein $R^1$ is selected from the group consisting of H, an alkyl, an alkyl halide, an ether, and a carboxylic acid;
wherein $R^2$ is selected from the group consisting of an alkyne and an aromatic; and
wherein $R^3$ is selected from the group consisting of H, a carboxyl, a carboxylic acid, and an alkyl.

2. The compound of claim 1, wherein $R^1$ is selected from the group consisting of: H,

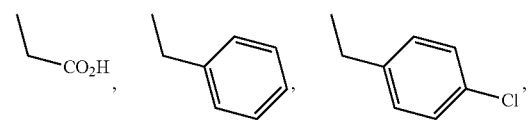

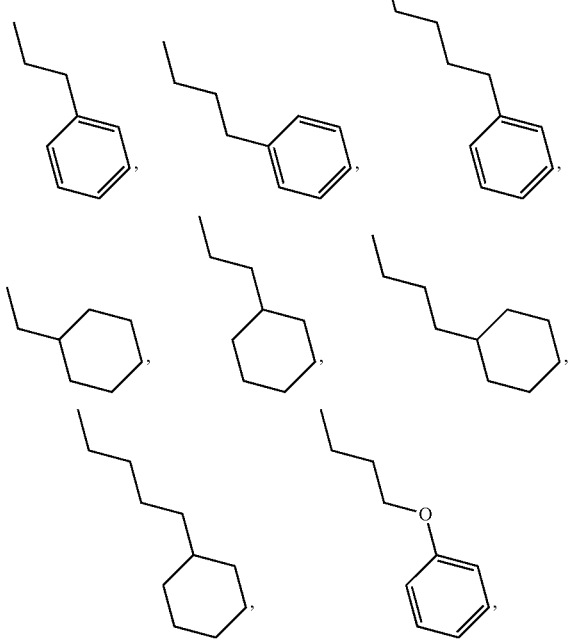

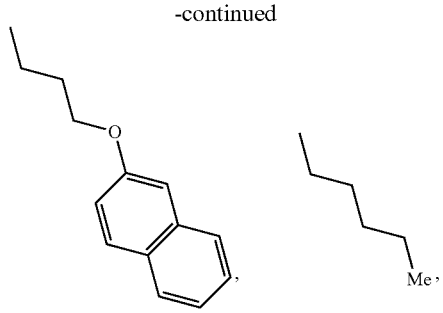

3. The compound of claim 1, wherein $R^2$ is selected from the group consisting of:

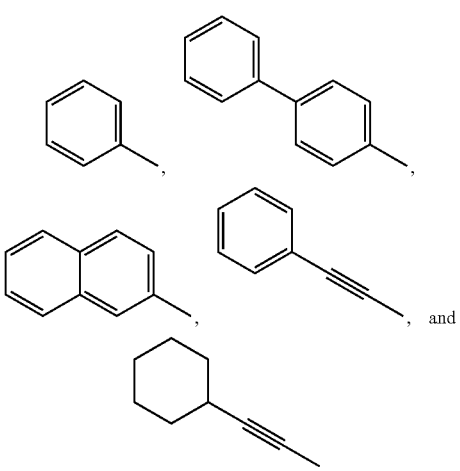

4. The compound of claim 1, wherein R³ is selected from the group consisting of:
H,
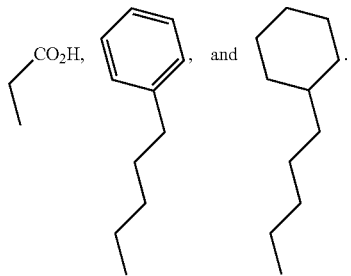
5. A compound having the formula selected from the group consisting of:
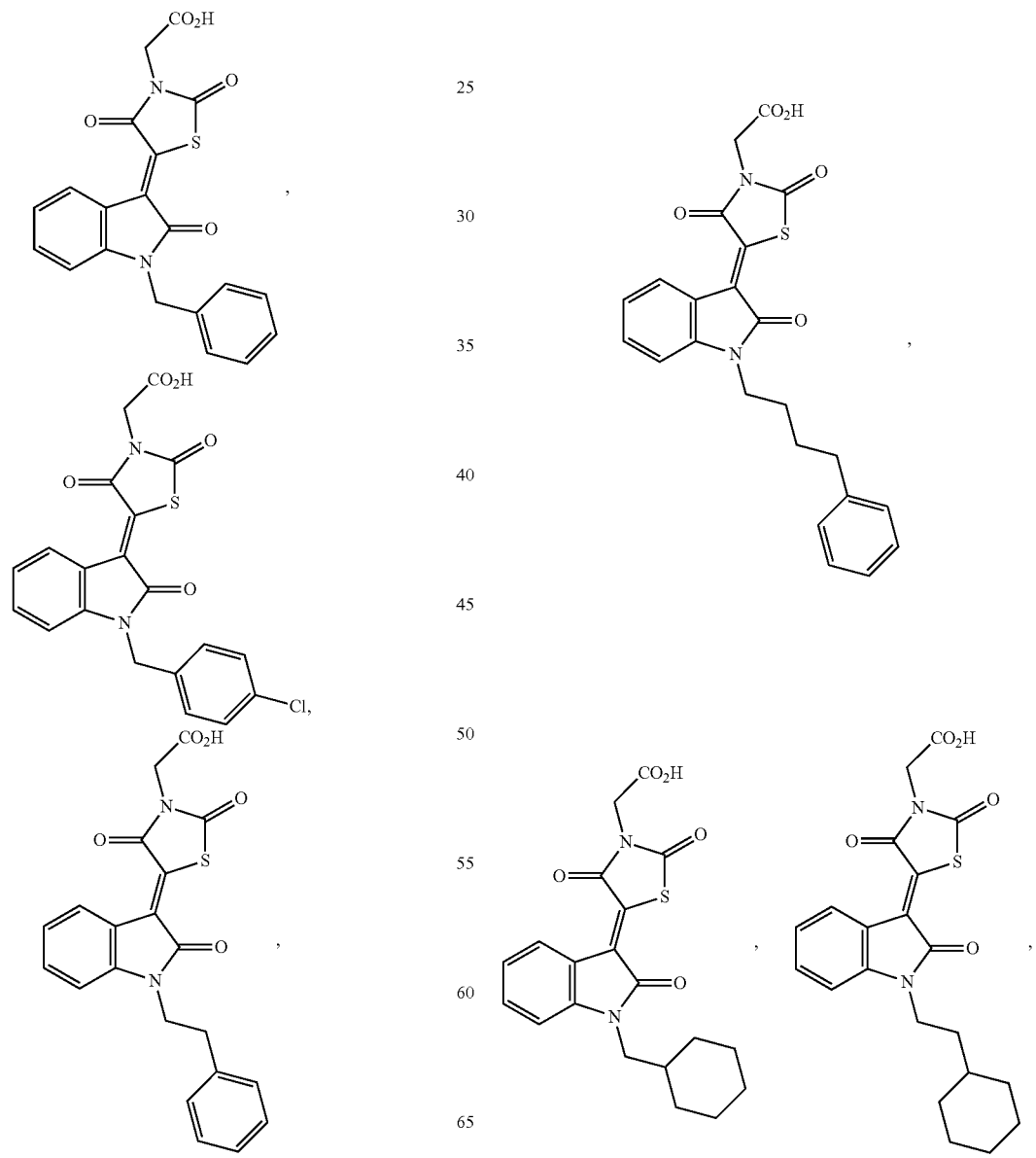
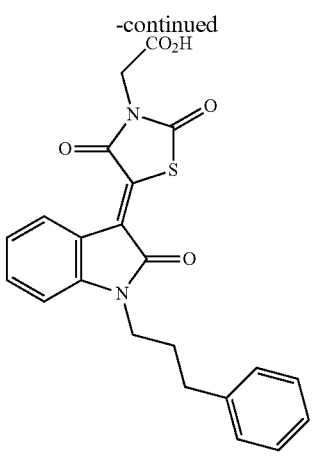

153
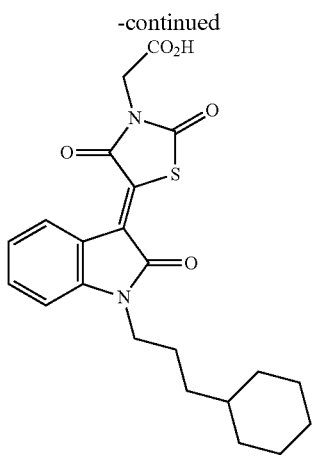
,
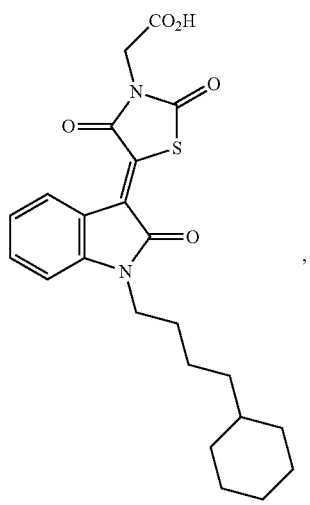
,
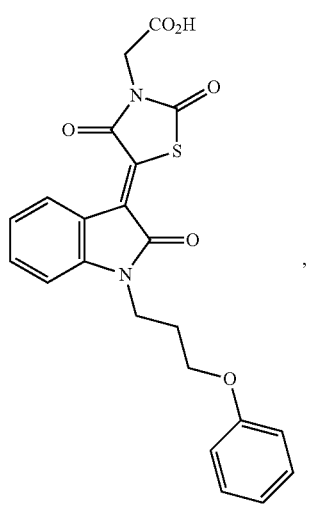
,
154
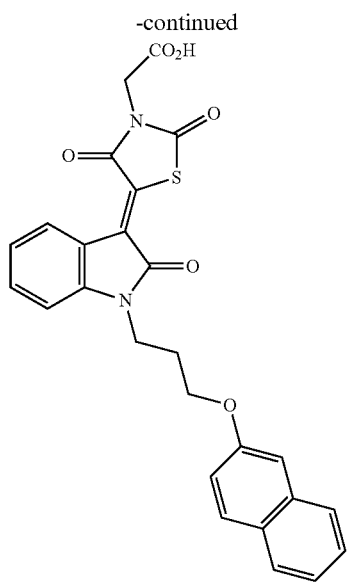
,
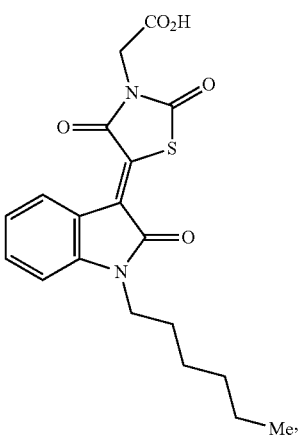
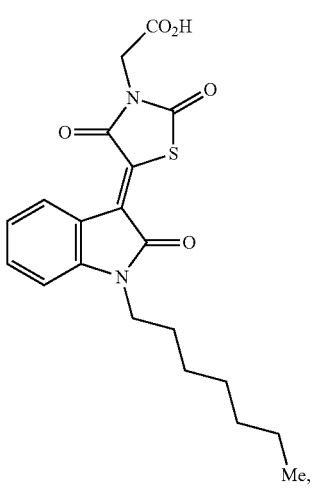
, 155
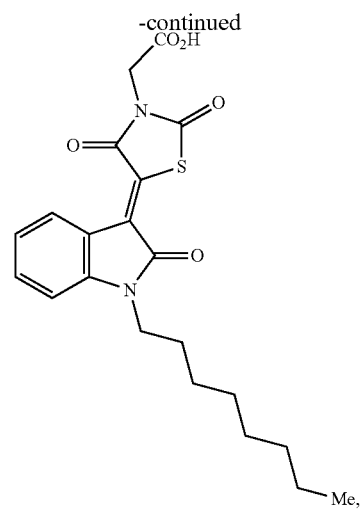
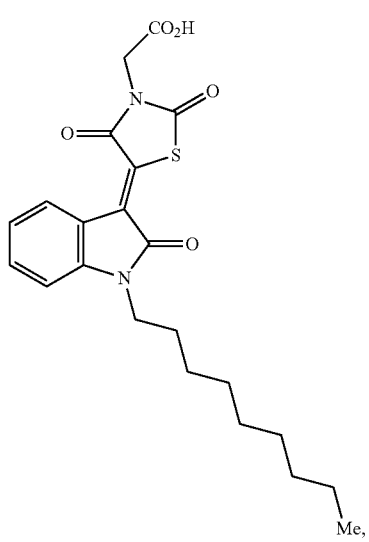
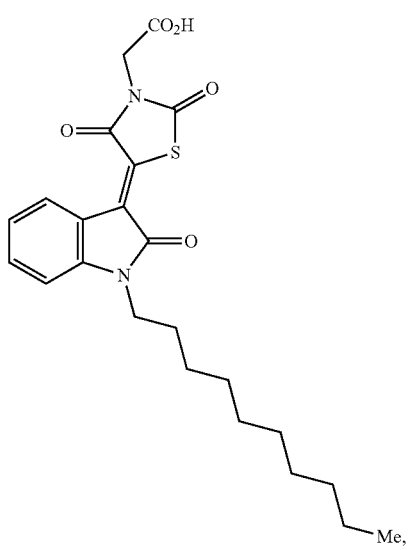
156
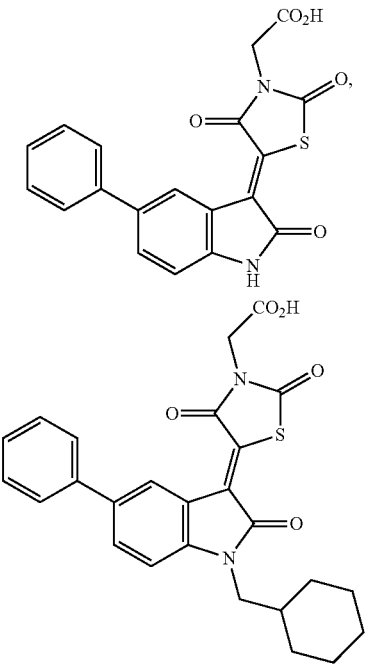
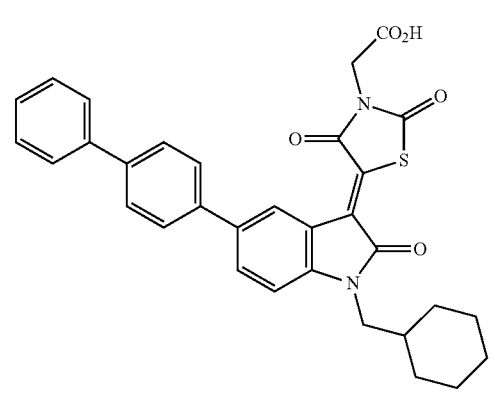
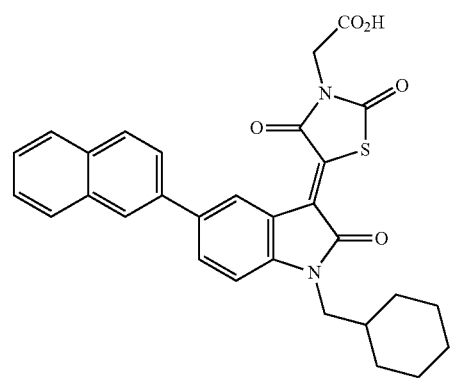

157
-continued
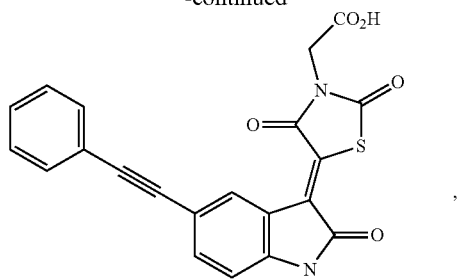
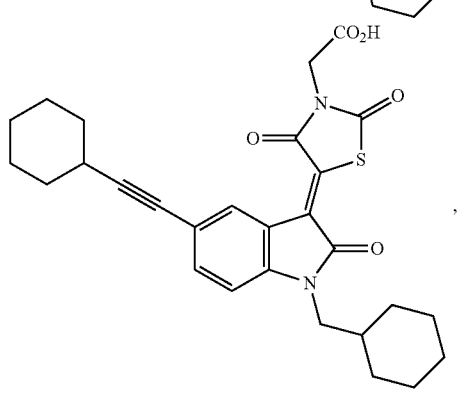
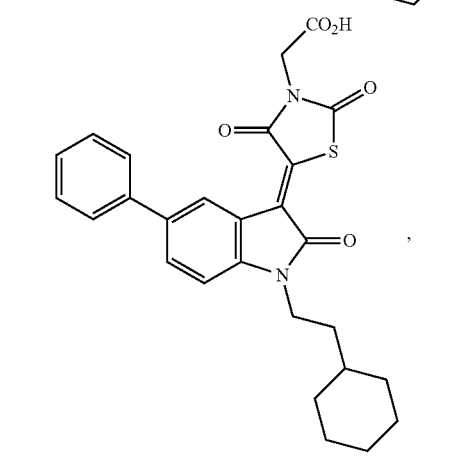
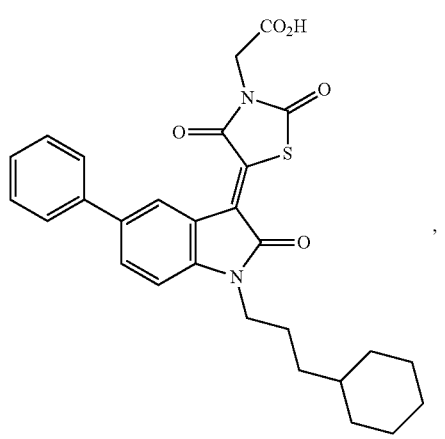
158
-continued
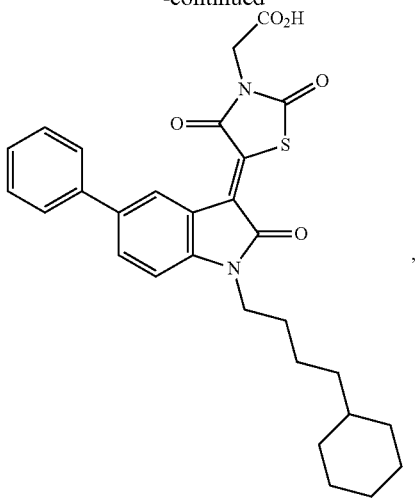
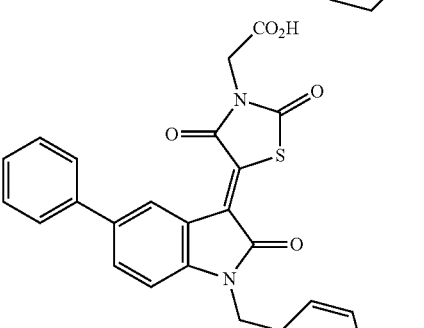
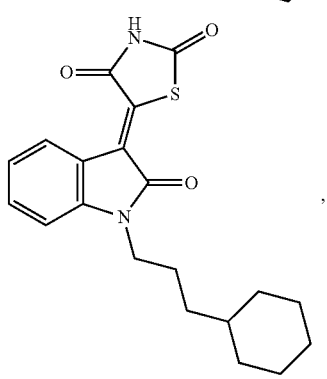
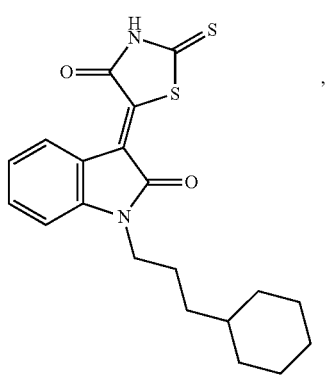

-continued

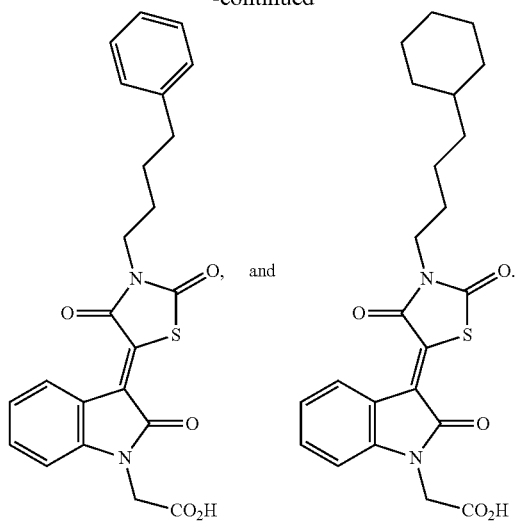

6. A pharmaceutical composition, comprising:
a first compound of the formula

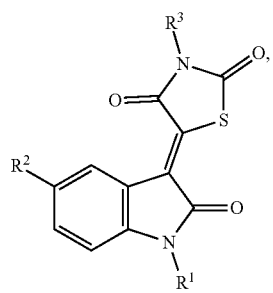

or pharmaceutically acceptable salts thereof,
wherein $R^1$ is selected from the group consisting of H, an alkyl, an alkyl halide, an ether, and a carboxylic acid,
wherein $R^2$ is selected from the group consisting of H, a halide, an alkyne, and an aromatic, and
wherein $R^3$ is selected from the group consisting of H, a carboxyl, a carboxylic acid, and an alkyl;
a pharmaceutically-acceptable carrier; and
a second compound or composition having mPGES-1 inhibition activity, having anti-inflammatory activity, being useful for treatment of an inflammation disorder, being useful for treatment of symptoms associated with inflammation and/or an inflammation disorder, or combinations thereof.

7. The pharmaceutical composition of claim 6, wherein $R^1$ of the first compound is selected from the group consisting of: H -continued

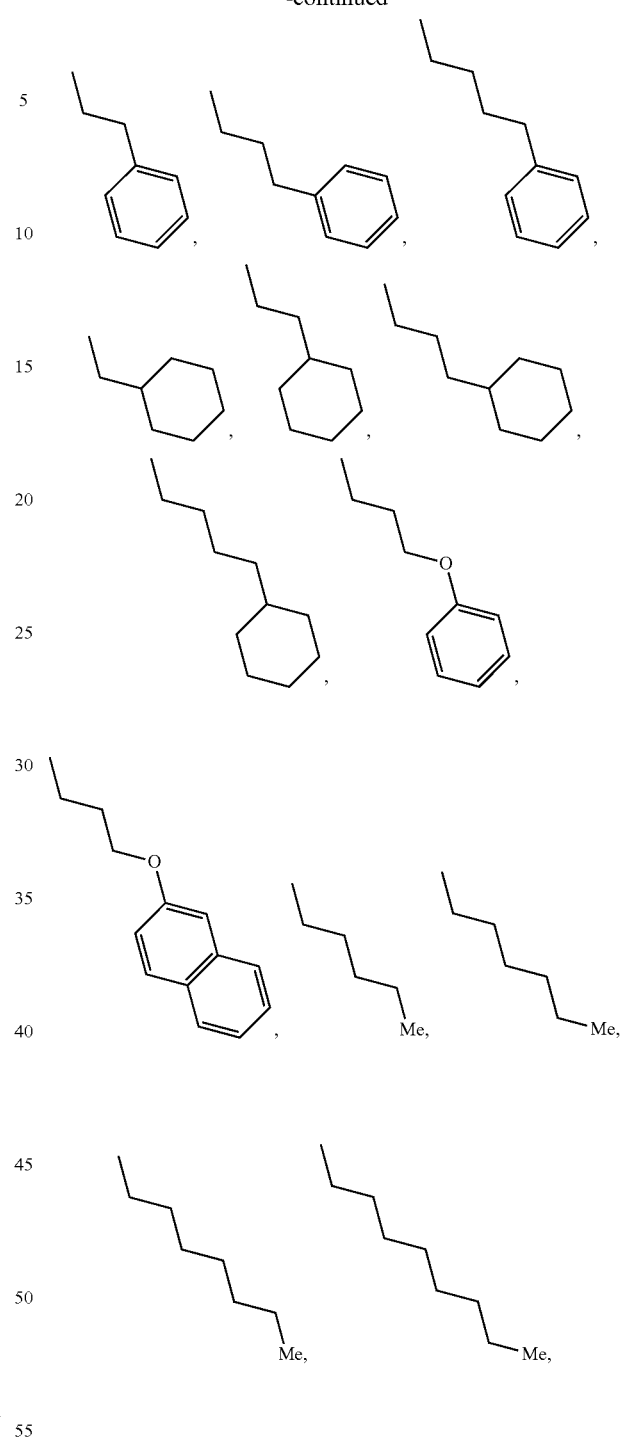

-continued

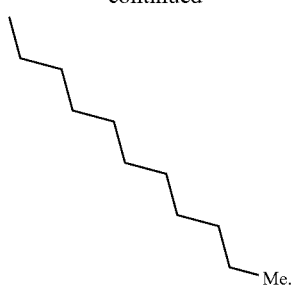

8. The pharmaceutical composition of claim 6, wherein R² of the first compound is selected from the group consisting of: H,

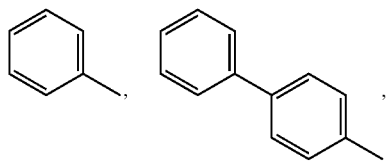

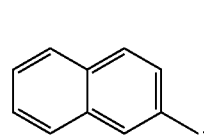

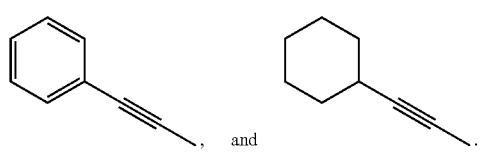, and

9. The pharmaceutical composition of claim 6, wherein R³ of the first compound is selected from the group consisting of: H,

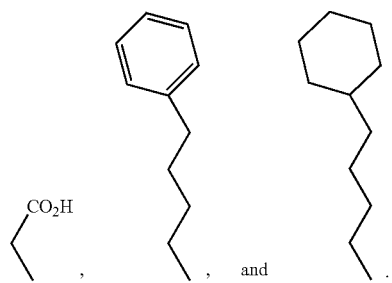

10. The pharmaceutical composition of claim 6, wherein the formula of the first compound is selected from the group consisting of:

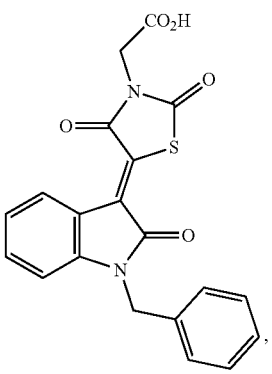

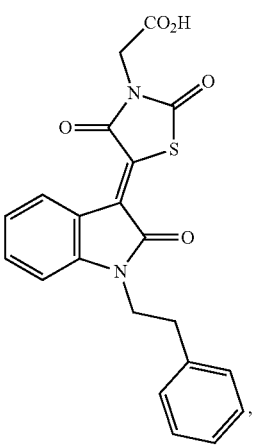

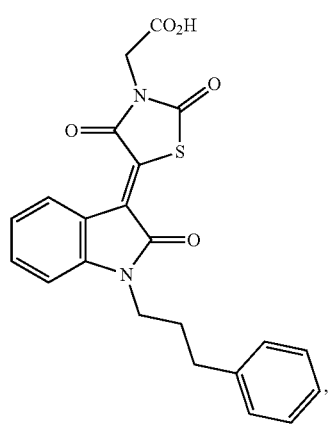

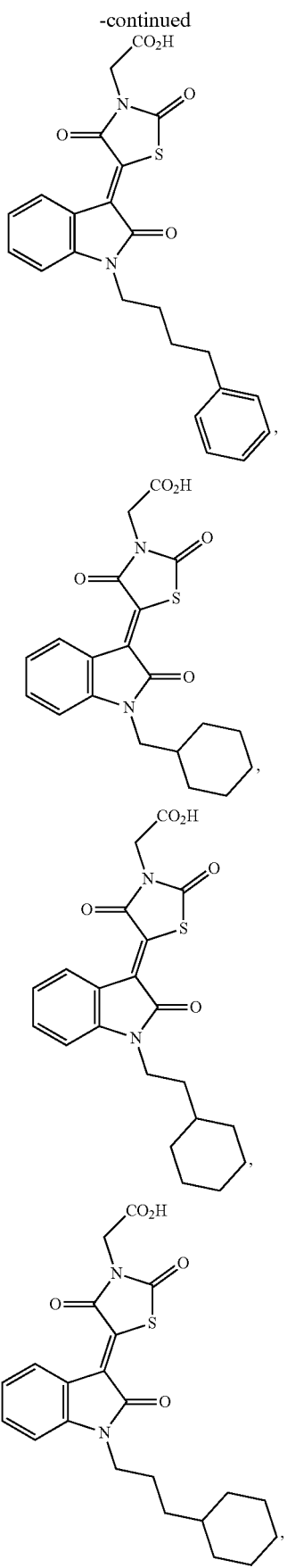
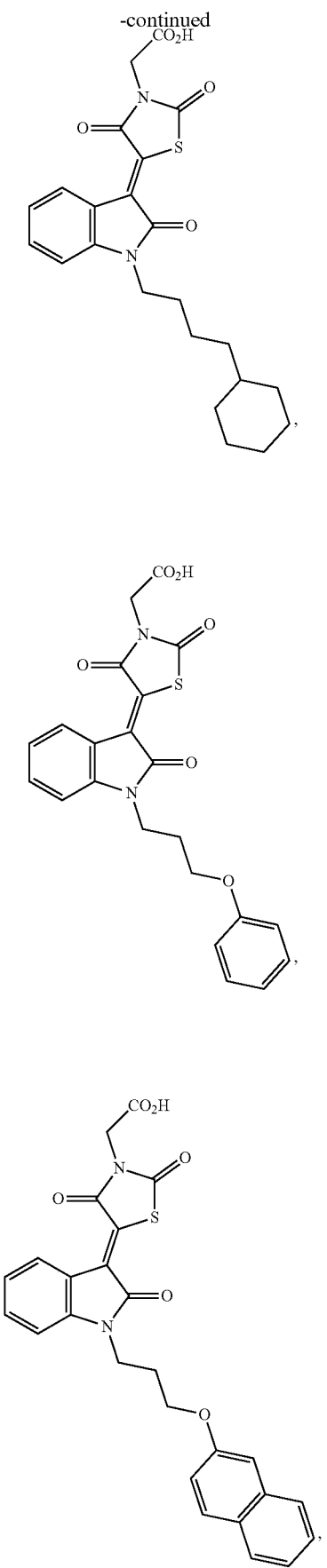

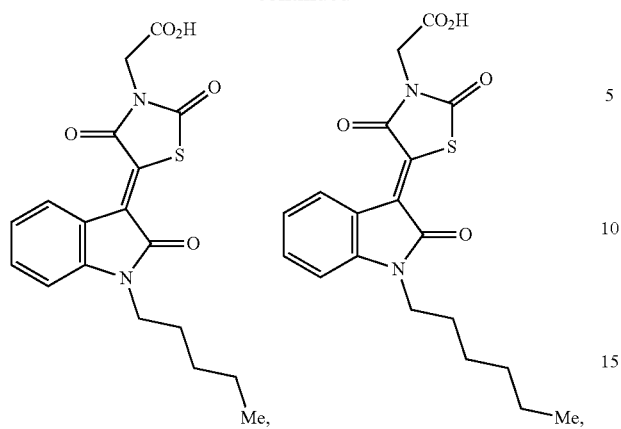
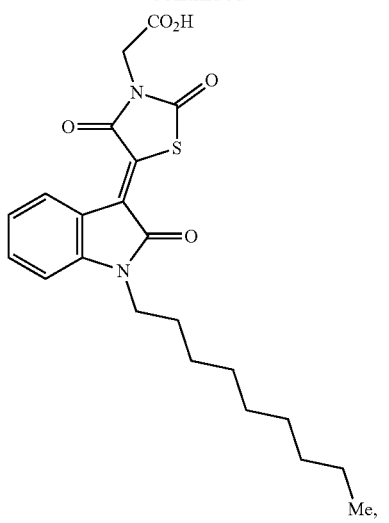
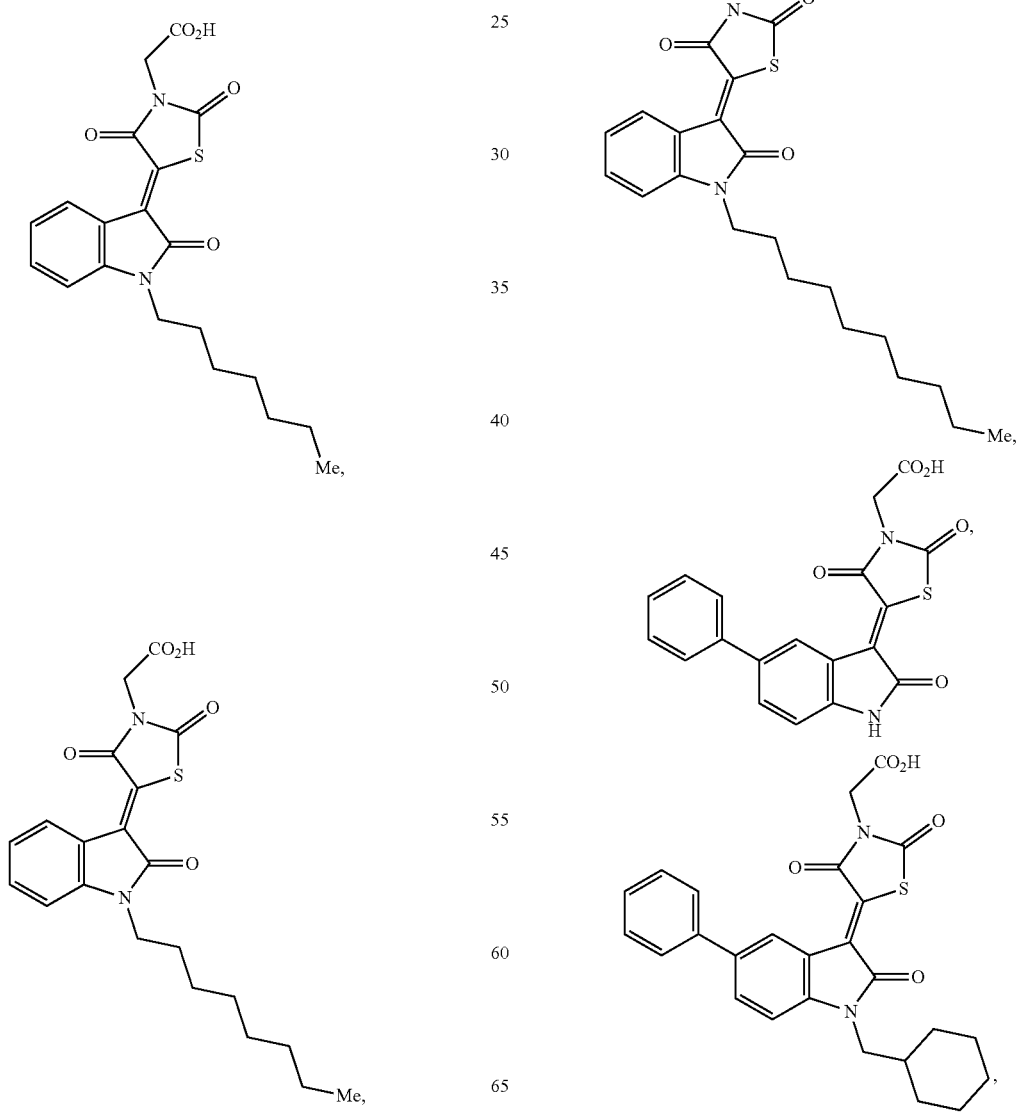
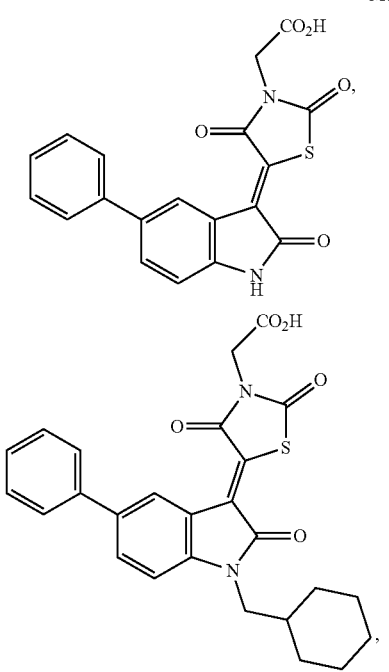

-continued
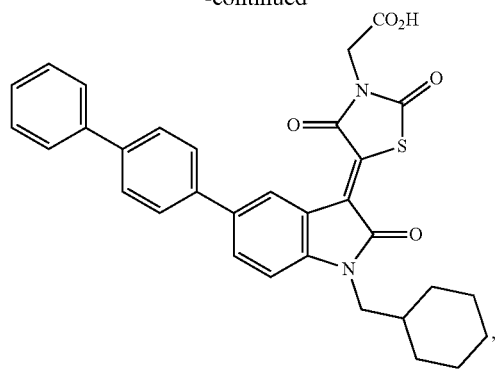
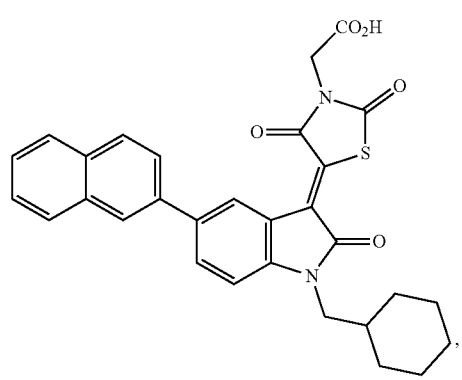
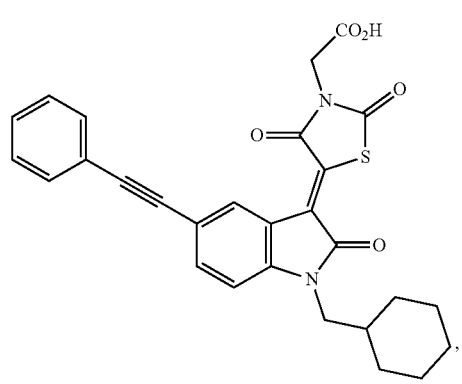
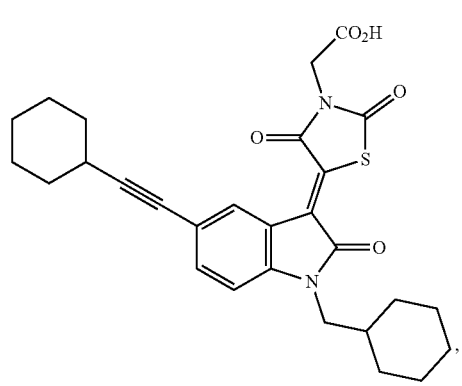
-continued
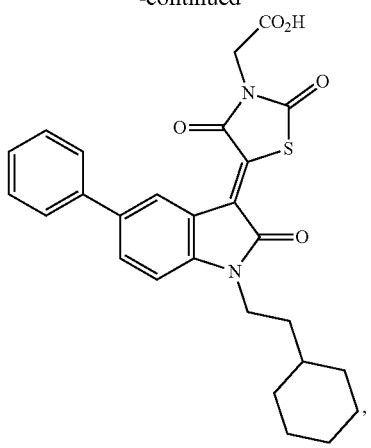
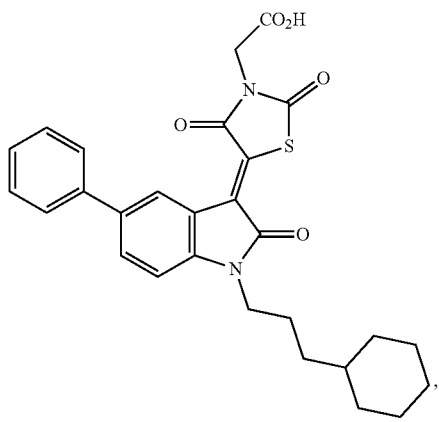
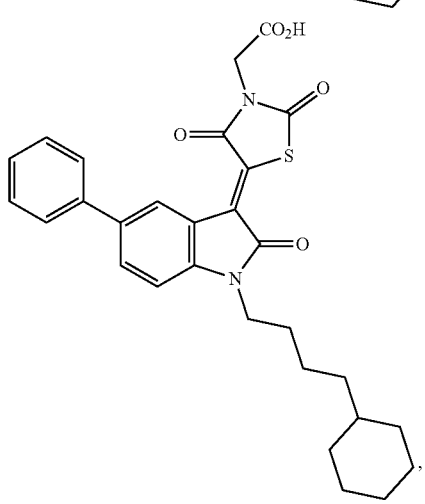
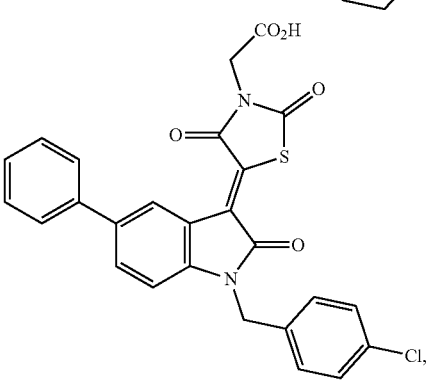

169
-continued
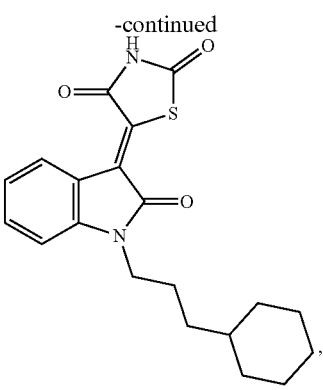
170
-continued
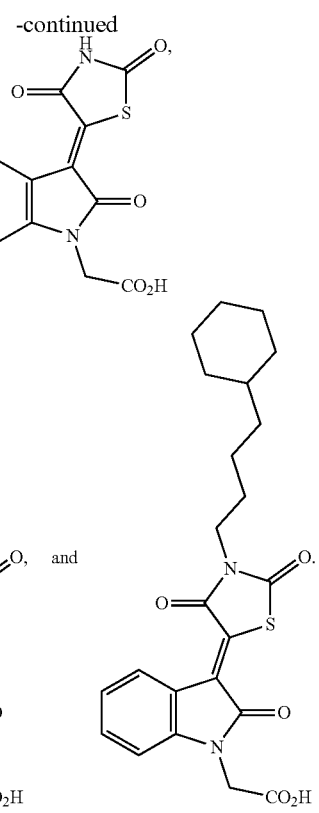
* * * * *